US011655296B2

(12) United States Patent
Liu et al.

(10) Patent No.: US 11,655,296 B2
(45) Date of Patent: May 23, 2023

(54) ANTI-CD47 ANTIBODY AND USE THEREOF

(71) Applicant: INNOVENT BIOLOGICS (SUZHOU) CO., LTD., Jiangsu (CN)

(72) Inventors: Dandan Liu, Jiangsu (CN); Weifeng Huang, Jiangsu (CN); Bingliang Chen, Jiangsu (CN); Junjian Liu, Jiangsu (CN)

(73) Assignee: INNOVENT BIOLOGICS (SUZHOU) CO., LTD., Jiangsu (CN)

( * ) Notice: Subject to any disclaimer, the term of this patent is extended or adjusted under 35 U.S.C. 154(b) by 309 days.

(21) Appl. No.: 16/966,081

(22) PCT Filed: Mar. 26, 2019

(86) PCT No.: PCT/CN2019/079687
§ 371 (c)(1),
(2) Date: Jul. 30, 2020

(87) PCT Pub. No.: WO2019/184912
PCT Pub. Date: Oct. 3, 2019

(65) Prior Publication Data
US 2020/0377593 A1 Dec. 3, 2020

(30) Foreign Application Priority Data

Mar. 27, 2018 (CN) .......................... 201810259545.2

(51) Int. Cl.
C07K 16/28 (2006.01)
A61P 35/00 (2006.01)
G01N 33/574 (2006.01)

(52) U.S. Cl.
CPC .......... *C07K 16/2803* (2013.01); *A61P 35/00* (2018.01); *G01N 33/57492* (2013.01); *C07K 2317/24* (2013.01); *C07K 2317/76* (2013.01); *C07K 2317/92* (2013.01)

(58) Field of Classification Search
CPC ............ C07K 16/2803; C07K 2317/24; C07K 2317/76; G01N 33/57492
See application file for complete search history.

(56) References Cited

U.S. PATENT DOCUMENTS

| | | | |
|---|---|---|---|
| 8,101,719 B2 | 1/2012 | Kikuchi et al. |
| 8,236,313 B2 | 8/2012 | Isenberg et al. |
| 8,562,997 B2 | 10/2013 | Jaiswal et al. |
| 8,758,750 B2 | 6/2014 | Weissman et al. |
| 8,759,025 B2 | 6/2014 | Kikuchi et al. |
| 8,951,527 B2 | 2/2015 | Isenberg et al. |
| 9,017,675 B2 | 4/2015 | Liu et al. |
| 9,045,541 B2 | 6/2015 | Eckelman et al. |
| 9,221,908 B2 | 12/2015 | Frazier et al. |
| 9,352,037 B2 | 5/2016 | van den Berg |
| 9,382,320 B2 | 7/2016 | Liu et al. |
| 9,399,682 B2 | 7/2016 | Jaiswal et al. |
| 9,518,116 B2 | 12/2016 | Frazier et al. |
| 9,518,117 B2 | 12/2016 | Frazier et al. |
| 9,605,076 B2 | 3/2017 | Jaiswal et al. |
| 9,611,329 B2 | 4/2017 | Jaiswal et al. |
| 2015/0183874 A1 | 7/2015 | Liu et al. |
| 2015/0238604 A1 | 8/2015 | Eckelman et al. |
| 2016/0304609 A1 | 10/2016 | Liu et al. |

FOREIGN PATENT DOCUMENTS

| | | |
|---|---|---|
| CN | 104271757 A | 1/2015 |
| CN | 105101997 A | 11/2015 |
| CN | 105102479 A | 11/2015 |
| CN | 105121467 A | 12/2015 |
| CN | 103665165 B | 2/2016 |
| CN | 106084052 A | 11/2016 |
| CN | 106117354 A | 11/2016 |
| EP | 1693385 A1 | 8/2006 |
| EP | 2282772 B1 | 1/2014 |
| EP | 2242512 B1 | 4/2016 |
| EP | 2569013 B1 | 11/2016 |
| JP | 2013-534409 A | 9/2013 |
| KR | 1020060121150 | 11/2006 |
| WO | 2005/044857 A1 | 5/2005 |
| WO | 2009/091547 A1 | 7/2009 |
| WO | 2014/094122 A1 | 6/2014 |
| WO | 2015/105995 A2 | 7/2015 |
| WO | 2017049251 A2 | 3/2017 |
| WO | 2019/129054 A1 | 7/2019 |

OTHER PUBLICATIONS

Almagro & Fransson, Humanization of antibodies, Frontiers in Bioscience 2008; 13: 1619-33 (Year: 2008).*
Sick et al., Activation of CD47 receptors causes proliferation of human astrocytoma but not normal astrocytes via an Akt-dependent pathway, Glia. 2011, 59(2): 308-19.
Pettersen et al., CD47 signals T cell death, J. Immunol., 1999, 162 (12): 7031-40.
Xu et al., Effect of CD47 on preventing and Treating Tumours, Guangdong Medical Journal., vol. 35, No.(18), 2014, pp. 2945-2947.
Yuan et al., Research Advances in the Relationship Between CD47 and Breast Cancer, Chinese Journal of Histochemistry and Cytochemistry., vol. 25, No. (4), 2016, pp. 371-374.
Uno et al. "Antitumor activity of a monoclonal antibody against CD47 in xenograft models of human leukemia": Oncol Rep 2007; 17: 1189-94.
Kikuchi et al.: "A bivalent single-chain Fv fragment against CD47 induces apoptosis for leukemic cells". Biochem Biophys Res Commun 2004 315: 912-8.

(Continued)

*Primary Examiner* — Peter J Reddig
*Assistant Examiner* — Cheng Lu
(74) *Attorney, Agent, or Firm* — Leason Ellis LLP

(57) ABSTRACT

The present invention relates to novel antibodies and antibody fragments thereof that specifically bind to integrin-associated proteins (IAP, or CD47), and a composition comprising the antibodies or the antibody fragments. The present invention also relates to a nucleic acid encoding the antibodies or the antibody fragments thereof, a host cell comprising the nucleic acid, and related use. Furthermore, the present invention also relates to therapeutic and diagnostic use of the antibodies and the antibody fragments.

19 Claims, 4 Drawing Sheets

Specification includes a Sequence Listing.

(56) References Cited

OTHER PUBLICATIONS

Zeng et al: "A fully human anti-C047 blocking antibody with therapeutic potential for cancer", ONCOTARGET, vol. 7, No. 50, 2016, pp. 83040-83050.
International Search Report and Written Opinion of PCT Application No. PCT/CN2019/079687, dated May 21, 2019.

* cited by examiner

ANTI-CD47 ANTIBODY AND USE THEREOF

SEQUENCE LISTING

The application contains a Sequence Listing which has been submitted electronically in ASCII format and is hereby incorporated by reference in its entirety. Said ASCII copy, created on Jul. 30, 2020, is named 11275-008845-US0_ST25-V2.txt and is 86,774 bytes in size.

The present invention relates to novel antibodies and antibody fragments thereof that specifically bind to integrin-associated proteins (IAP, or CD47), and a composition comprising the antibodies or the antibody fragments. The present invention also relates to a nucleic acid encoding the antibodies or the antibody fragments thereof, a host cell comprising the nucleic acid, and related use. Furthermore, the present invention also relates to therapeutic and diagnostic use of the antibodies and the antibody fragments.

BACKGROUND

Recently cancer immunotherapy has become a highlight in the field of bioscience Immune checkpoint inhibitor therapies (such as CTLA4 antibody, PD-1 antibody and PD-L1 antibody based on T cells) and cell therapies (such as CAR-T and TCR-T) are all immunotherapies that have become very popular in recent years. All these immunotherapies are carried out around how to recover the function of T cells, i.e., mainly around how to enhance the ability of the adaptive immune system. However, it is still full of twists and turns to activate the function of T cells with an immune checkpoint as a target so as to enhance the ability of the adaptive immune system to conquer cancer, and the innate immune system has not played a role in tumor immunotherapy for a long term. As a matter of fact, in an entire tumor-infiltrated region, macrophages account for about 50% of a tumor tissue, and more importantly, the number of the macrophages shows an inverse relation with the prognosis of the tumor, which further proves the important role of the macrophages in the tumor.

The phagocytosis of macrophages requires two signals to function simultaneously: one is the activation of an "eat me" signal on the surface of target cells, and the other is the deactivation of a "don't eat me" signal on the same surface. The absence of any of the signals will lead to the failure of inducing the phagocytosis. More and more evidences indicate that, CD47 is a kind of "don't eat me" signal and inhibits the phagocytosis of macrophages by binding to the signal regulatory protein α (SIRPα) on the surface of the macrophages. Tumor cells can also evade the phagocytosis of macrophages by the expression of CD47 (for example, see EP2242512 and related literatures cited therein).

CD47, also called an integrin-associated protein (IAP), is a member of the immunoglobulin superfamily. CD47 is widely expressed on the surface of cells, and can interact with SIRPα, thrombospondin-1 (TSP1) and integrin to mediate a series of reactions, such as apoptosis, proliferation, and immunization. TSP1 is associated with the proliferation, growth and differentiation of cells, and the binding of CD47 to TSP1 plays an important role in the regulation of cell migration, the proliferation and apoptosis of cells, the promotion of angiogenesis and the inflammatory reaction. In addition, CD47 is an important marker of self on the surface of cells. CD47 can bind to SIRPα on the surface of macrophages to phosphorylate the immunoreceptor tyrosine-based inhibitory motif (ITIM) thereof, and then recruits SHP-1 proteins to generate a series of cascade reactions to inhibit the phagocytosis of the macrophages (for example, see U.S. Pat. No. 9,382,320 and related literatures cited therein).

Different studies show that almost all tumor cells and tissues can highly express CD47. CD47 that is highly expressed on the surface of tumor cells can bind to SIRPα on the surface of macrophages to release the "don't eat me" signal. As a result, the macrophages in a tumor infiltrated area not only coexist in harmony with the tumor cells, but also can inhibit effector T cells from functioning and promote the proliferation and growth of the tumor cells by promoting the proliferation of blood vessels in the tumor.

The role of CD47 in promoting cell proliferation largely depends on cell types, because the activation and loss of CD47 can lead to enhanced proliferation. Using TSP-1 to activate CD47 can enhance the proliferation of human U87 and U373 astrocytoma cells but not normal astrocytes. In addition, CD47-blocking antibodies can inhibit the proliferation of unstimulated astrocytoma cells but not normal astrocytes. Although the exact mechanism is not clear yet, CD47 may promote the proliferation of cancer cells but not normal cells via a PI3K/Akt pathway (Sick E, Boukhari A, Deramaudt T, Rondé P, Bucher B, André P, Gies J P, Takeda K., Activation of CD47 receptors causes proliferation of human astrocytoma but not normal astrocytes via an Akt-dependent pathway, Glia. 2011 February, 59(2): 308-19: 308-19).

CD47 ligation leads to cell death in many normal and tumor cell lines via apoptosis or autophagy. The activation of CD47 induces the rapid apoptosis of T cells. Jurkat cells and peripheral blood monouclear cells (PBMC) that are incubated using a monoclonal antibody Ad22 result in apoptosis within 3 hours. However, after using other anti-CD47 antibodies for culture, no apoptosis is observed. The apoptosis-inducing function of CD47 seemed to depend on the activation of a specific epitope on an extracellular domain (Pettersen R D, Hestdal K, Olafsen M K, Lie S O, Lindberg F P (June 1999), CD47 signals T cell death, J. Immunol. 162(12): 7031-40. PMID 10358145).

So far, multiple anti-CD47 antibodies have been reported. For example, U.S. Patent US2015/0183874 A1 reported a human IgG1 chimeric monoclonal antibody derived from B6H12 and a humanized B6H12 antibody produced by CDR grafting, which have lower immunogenicity than known antibodies. U.S. Patent U.S. Pat. No. 9,045,541 reported an anti-CD47 antibody that does not significantly cause hemagglutination, and moreover, compared with known antibodies, this antibody is significantly effective in a tumor model, such as increasing the capability of macrophages in phagocytizing tumor cells.

While promoting the phagocytizing effect of macrophages, the vast majority of antibodies capable of blocking the binding between CD47 and SIRPα known in the prior art can cause erythrocyte agglutination, and as a result, the therapeutic effect of the corresponding antibodies is greatly reduced.

Therefore, in therapies for various tumors and/or cancers, there is still an urgent need to develop an anti-CD47 antibody with good target specificity, excellent curative effect (such as improving the phagocytosis of macrophages, inhibiting tumor growth and even making tumor completely disappear) and less side effects. The present invention meets the requirements in this aspect.

SUMMARY OF THE INVENTION

The present invention provides anti-CD47 antibodies, a composition related to the anti-CD47 antibodies, a kit, a method, and use.

The inventor of the present invention surprisingly discovered that the antibodies developed by the present invention can significantly promote the phagocytosis of tumor cells by macrophages, and do not have the activity of promoting erythrocyte agglutination.

In some embodiments, the present invention provides anti-CD47 antibodies or antibody fragments (preferably antigen-binding fragments) binding to CD47 or a fragment (preferably human CD47 protein) thereof.

In some embodiments, the antibodies of the present invention comprise one, two or three CDRs (preferably three CDRs) of a VH sequence of any one of the antibodies shown in Table 3, or variants thereof. In other embodiments, the antibodies of the present invention comprise one, two or three CDRs (preferably three CDRs) of a VL sequence of any one of the antibodies shown in Table 3, or variants thereof. In some embodiments, the antibodies of the present invention comprise six CDR sequences of any one of the antibodies shown in Table 3, or variants thereof. In one embodiment, the CDR sequences of the antibodies are the CDR sequences shown in Table 2.

In some embodiments, the anti-CD47 antibodies or the antigen-binding fragments thereof of the present invention comprise one to three heavy chain complementarity determining regions (HCDRs) selected from (i) an HCDR1, comprising an amino acid sequence selected from SEQ ID NOs: 15, 16, 17, 18, 19, 20 and 69 or a sequence containing amino acid substitutions (such as conservative substitutions), deletions or insertions of one or more, but no more than 5, amino acids relative to the sequence; (ii) an HCDR2, comprising an amino acid sequence selected from SEQ ID NOs: 21, 22, 23, 24, 25, 26, 27, 28, 29, 30 and 70 or a sequence containing one or more amino acid substitutions (such as conservative substitutions), deletions or insertions of one or more, but no more than 5, amino acids relative to the sequence; (iii) an HCDR3, comprising an amino acid sequence selected from SEQ ID NOs: 31, 32, 33, 34 and 35 or a sequence containing amino acid substitutions (such as conservative substitutions), deletions or insertions of one or more, but no more than 5, amino acids relative to the sequence, or consists of the sequences, wherein the anti-CD47 antibodies comprising the modified CDRs can still bind to CD47.

In some embodiments, the anti-CD47 antibodies or the antigen-binding fragments thereof of the present invention comprise one to three light chain complementarity determining regions (LCDRs) selected from (i) a LCDR1, comprising an amino acid sequence selected from SEQ ID NOs: 36, 37, 38 and 71 or a sequence containing amino acid substitutions (such as conservative substitutions), deletions or insertions of one or more, but no more than 5, amino acids relative to the sequence; (ii) a LCDR2, comprising an amino acid sequence selected from SEQ ID NOs: 39, 40 and 72 or a sequence containing amino acid substitutions (such as conservative substitutions), deletions or insertions of one or more, but no more than 5, amino acids relative to the sequence; (iii) a LCDR3, comprising an amino acid sequence selected from SEQ ID NOs: 41, 42, 43 and 44 or a sequence containing amino acid substitutions (such as conservative substitutions), deletions or insertions of one or more, but no more than 5, amino acids relative to the sequence, or consist of the sequences, wherein the anti-CD47 antibodies comprising the modified CDRs can still bind to CD47.

In some embodiments, the anti-CD47 antibodies or the antigen-binding fragments thereof of the present invention comprise (A) one or more heavy chain complementarity determining regions (HCDRs) selected from (i) an HCDR1, comprising an amino acid sequence selected from SEQ ID NOs: 15, 16, 17, 18, 19, 20 and 69 or a sequence containing amino acid substitutions (such as conservative substitutions), deletions or insertions of one or more, but no more than 5, amino acids relative to the sequence; (ii) an HCDR2, comprising an amino acid sequence selected from SEQ ID NOs: 21, 22, 23, 24, 25, 26, 27, 28, 29, 30 and 70 or a sequence containing amino acid substitutions (such as conservative substitutions), deletions or insertions of one or more, but no more than 5, amino acids relative to the sequence; (iii) an HCDR3, comprising an amino acid sequence selected from SEQ ID NOs: 31, 32, 33, 34 and 35 or a sequence containing amino acid substitutions (such as conservative substitutions), deletions or insertions of one or more, but no more than 5, amino acids relative to the sequence; and (B) one to three light chain complementarity determining regions (LCDRs) selected from (i) a LCDR1, comprising an amino acid sequence selected from SEQ ID NOs: 36, 37, 38 and 71 or a sequence containing amino acid substitutions (such as conservative substitutions), deletions or insertions of one or more, but no more than 5, amino acids relative to the sequence; (ii) a LCDR2, comprising an amino acid sequence selected from SEQ ID NOs: 39, 40 and 72 or a sequence containing amino acid substitutions (such as conservative substitutions), deletions or insertions of one or more, but no more than 5, amino acids relative to the sequence; (iii) a LCDR3, comprising an amino acid sequence selected from SEQ ID NOs: 41, 42, 43 and 44 or a sequence containing amino acid substitutions (such as conservative substitutions), deletions or insertions of one or more, but no more than 5, amino acids relative to the sequence, wherein the anti-CD47 antibodies comprising the modified CDRs can still bind to CD47.

In some embodiments, the anti-CD47 antibodies or the antigen-binding fragments thereof of the present invention comprise one to three heavy chain complementarity determining regions (HCDRs) selected from (i) an HCDR1, consisting of an amino acid sequence selected from SEQ ID NOs: 15, 16, 17, 18, 19, 20 and 69; (ii) an HCDR2, consisting of an amino acid sequence selected from SEQ ID NOs: 21, 22, 23, 24, 25, 26, 27, 28, 29, 30 and 70; (iii) an HCDR3, consisting of an amino acid sequence selected from SEQ ID NOs: 31, 32, 33, 34 and 35.

In some embodiments, the anti-CD47 antibodies or the antigen-binding fragments thereof of the present invention comprise one to three light chain complementarity determining regions (LCDRs) selected from (i) a LCDR1, consisting of an amino acid sequence selected from SEQ ID NOs: 36, 37, 38 and 71; (ii) a LCDR2, consisting of an amino acid sequence selected from SEQ ID NOs: 39, 40 and 72; (iii) a LCDR3, consisting of an amino acid sequence selected from SEQ ID NOs: 41, 42, 43 and 44.

In some embodiments, the anti-CD47 antibodies or the antigen-binding fragments thereof of the present invention comprise (A) one or more heavy chain complementarity determining regions (HCDRs) selected from (i) an HCDR1, consisting of a sequence selected from SEQ ID NOs: 15, 16, 17, 18, 19, 20 and 69; (ii) an HCDR2, consisting of an amino acid sequence selected from SEQ ID NOs: 21, 22, 23, 24, 25, 26, 27, 28, 29, 30 and 70; (iii) an HCDR3, consisting of an amino acid sequence selected from SEQ ID NOs: 31, 32, 33, 34 and 35; and (B) one to three light chain complementarity determining regions (LCDRs) selected from (i) a LCDR1, consisting of an amino acid sequence selected from SEQ ID NOs: 36, 37, 38 and 71; (ii) a LCDR2, consisting of an amino acid sequence selected from SEQ ID NOs: 39, 40 and 72; (iii) a LCDR3, consisting of an amino acid sequence selected from SEQ ID NOs: 41, 42, 43 and 44.

In one preferred embodiment, the aforementioned one or more amino acid modifications in the CDRs contain amino acid substitutions (such as conservative substitutions), deletions or insertions of no more than 5, 4, 3, 2, 1 or 0 amino acid.

In some embodiments, the anti-CD47 antibodies or the antigen-binding fragments thereof of the present invention comprise heavy chain complementarity determining regions HCDR1, HCDR2 and HCDR3, wherein the HCDR1 comprises or consists of an amino acid sequence selected from SEQ ID NOs: 15, 16, 17, 18, 19, 20 and 69; the HCDR2 comprises or consists of an amino acid sequence selected from SEQ ID NOs: 21, 22, 23, 24, 25, 26, 27, 28, 29, 30 and 70; and the HCDR3 comprises or consists of an amino acid sequence selected from SEQ ID NOs: 31, 32, 33, 34 and 35.

In some embodiments, the anti-CD47 antibodies or the antigen-binding fragments thereof of the present invention comprise light chain complementarity determining regions LCDR1, LCDR2 and LCDR3, wherein the LCDR1 comprises or consists of an amino acid sequence selected from SEQ ID NOs: 36, 37, 38 and 71; the LCDR2 comprises or consists of an amino acid sequence selected from SEQ ID NOs: 39, 40 and 72; and the LCDR3 comprises or consists of an amino acid sequence selected from SEQ ID NOs: 41, 42, 43 and 44.

In some embodiments, the anti-CD47 antibodies or the antigen-binding fragments thereof of the present invention comprise heavy chain complementarity determining regions HCDR1, HCDR2 and HCDR3 and light chain complementarity determining regions LCDR1, LCDR2 and LCDR3, wherein the HCDR1 comprises or consists of an amino acid sequence selected from SEQ ID NOs: 15, 16, 17, 18, 19, 20 and 69; the HCDR2 comprises or consists of an amino acid sequence selected from SEQ ID NOs: 21, 22, 23, 24, 25, 26, 27, 28, 29, 30 and 70; the HCDR3 comprises or consists of an amino acid sequence selected from SEQ ID NOs: 31, 32, 33, 34 and 35; the LCDR1 comprises or consists of an amino acid sequence selected from SEQ ID NOs: 36, 37, 38 and 71; the LCDR2 comprises or consists of an amino acid sequence selected from SEQ ID NOs: 39, 40 and 72; and the LCDR3 comprises or consists of an amino acid sequence selected from SEQ ID NOs: 41, 42, 43 and 44.

In a preferred embodiment, the present invention provides an anti-CD47 antibody or an antigen-binding fragment thereof, which comprises heavy chain complementarity determining regions HCDR1, HCDR2 and HCDR3 and light chain complementarity determining regions LCDR1, LCDR2 and LCDR3, wherein the HCDR1 comprises or consists of an amino acid sequence set forth in SEQ ID NO: 69, the HCDR2 comprises or consists of an amino acid sequence set forth in SEQ ID NO: 70, and the HCDR3 comprises or consists of an amino acid sequence set forth in SEQ ID NO: 31, 32, 33, 34 or 35; the LCDR1 comprises or consists of an amino acid sequence set forth in SEQ ID NO: 71, the LCDR2 comprises or consists of an amino acid sequence set forth in SEQ ID NO: 72, and the LCDR3 comprises or consists of an amino acid sequence set forth in SEQ ID NO: 41, 42, 43 or 44.

In a preferred embodiment, the present invention provides an anti-CD47 antibody or an antigen-binding fragment thereof, wherein the HCDR1 comprises or consists of an amino acid sequence set forth in SEQ ID NO: 15, the HCDR2 comprises or consists of an amino acid sequence set forth in SEQ ID NO: 21, and the HCDR3 comprises or consists of an amino acid sequence set forth in SEQ ID NO: 31; the LCDR1 comprises or consists of an amino acid sequence set forth in SEQ ID NO: 36, the LCDR2 comprises or consists of an amino acid sequence set forth in SEQ ID NO: 39, and the LCDR3 comprises or consists of an amino acid sequence set forth in SEQ ID NO: 41.

In a preferred embodiment, the present invention provides an anti-CD47 antibody or an antigen-binding fragment thereof, wherein the HCDR1 comprises or consists of an amino acid sequence set forth in SEQ ID NO: 16, the HCDR2 comprises or consists of an amino acid sequence set forth in SEQ ID NO: 22, and the HCDR3 comprises or consists of an amino acid sequence set forth in SEQ ID NO: 31; the LCDR1 comprises or consists of an amino acid sequence set forth in SEQ ID NO: 36, the LCDR2 comprises or consists of an amino acid sequence set forth in SEQ ID NO: 39, and the LCDR3 comprises or consists of an amino acid sequence set forth in SEQ ID NO: 41.

In a preferred embodiment, the present invention provides an anti-CD47 antibody or an antigen-binding fragment thereof, wherein the HCDR1 comprises or consists of an amino acid sequence set forth in SEQ ID NO: 17, the HCDR2 comprises or consists of an amino acid sequence set forth in SEQ ID NO: 23, and the HCDR3 comprises or consists of an amino acid sequence set forth in SEQ ID NO: 31; the LCDR1 comprises or consists of an amino acid sequence set forth in SEQ ID NO: 36, the LCDR2 comprises or consists of an amino acid sequence set forth in SEQ ID NO: 39, and the LCDR3 comprises or consists of an amino acid sequence set forth in SEQ ID NO: 41.

In a preferred embodiment, the present invention provides an anti-CD47 antibody or an antigen-binding fragment thereof, wherein the HCDR1 comprises or consists of an amino acid sequence set forth in SEQ ID NO: 18, the HCDR2 comprises or consists of an amino acid sequence set forth in SEQ ID NO: 24, and the HCDR3 comprises or consists of an amino acid sequence set forth in SEQ ID NO: 32; the LCDR1 comprises or consists of an amino acid sequence set forth in SEQ ID NO: 36, the LCDR2 comprises or consists of an amino acid sequence set forth in SEQ ID NO: 39, and the LCDR3 comprises or consists of an amino acid sequence set forth in SEQ ID NO: 42.

In a preferred embodiment, the present invention provides an anti-CD47 antibody or an antigen-binding fragment thereof, wherein the HCDR1 comprises or consists of an amino acid sequence set forth in SEQ ID NO: 17, the HCDR2 comprises or consists of an amino acid sequence set forth in SEQ ID NO: 25, and the HCDR3 comprises or consists of an amino acid sequence set forth in SEQ ID NO: 33; the LCDR1 comprises or consists of an amino acid sequence set forth in SEQ ID NO: 36, the LCDR2 comprises or consists of an amino acid sequence set forth in SEQ ID NO: 39, and the LCDR3 comprises or consists of an amino acid sequence set forth in SEQ ID NO: 42.

In a preferred embodiment, the present invention provides an anti-CD47 antibody or an antigen-binding fragment thereof, wherein the HCDR1 comprises or consists of an amino acid sequence set forth in SEQ ID NO: 19, the HCDR2 comprises or consists of an amino acid sequence set forth in SEQ ID NO: 26, and the HCDR3 comprises or consists of an amino acid sequence set forth in SEQ ID NO: 32; the LCDR1 comprises or consists of an amino acid sequence set forth in SEQ ID NO: 36, the LCDR2 comprises or consists of an amino acid sequence set forth in SEQ ID NO: 39, and the LCDR3 comprises or consists of an amino acid sequence set forth in SEQ ID NO: 42.

In a preferred embodiment, the present invention provides an anti-CD47 antibody or an antigen-binding fragment thereof, wherein the HCDR1 comprises or consists of an amino acid sequence set forth in SEQ ID NO: 16, the HCDR2 comprises or consists of an amino acid sequence set forth in SEQ ID NO: 27, and the HCDR3 comprises or consists of an amino acid sequence set forth in SEQ ID NO: 34; the LCDR1 comprises or consists of an amino acid sequence set forth in SEQ ID NO: 37, the LCDR2 comprises or consists of an amino acid sequence set forth in SEQ ID NO: 40, and the LCDR3 comprises or consists of an amino acid sequence set forth in SEQ ID NO: 43.

In a preferred embodiment, the present invention provides an anti-CD47 antibody or an antigen-binding fragment thereof, wherein the HCDR1 comprises or consists of an amino acid sequence set forth in SEQ ID NO: 20, the HCDR2 comprises or consists of an amino acid sequence set forth in SEQ ID NO: 28, and the HCDR3 comprises or consists of an amino acid sequence set forth in SEQ ID NO: 34; the LCDR1 comprises or consists of an amino acid sequence set forth in SEQ ID NO: 37, the LCDR2 comprises or consists of an amino acid sequence set forth in SEQ ID NO: 40, and the LCDR3 comprises or consists of an amino acid sequence set forth in SEQ ID NO: 43.

In a preferred embodiment, the present invention provides an anti-CD47 antibody or an antigen-binding fragment thereof, wherein the HCDR1 comprises or consists of an amino acid sequence set forth in SEQ ID NO: 16, the HCDR2 comprises or consists of an amino acid sequence set forth in SEQ ID NO: 29, and the HCDR3 comprises or consists of an amino acid sequence set forth in SEQ ID NO: 35; the LCDR1 comprises or consists of an amino acid sequence set forth in SEQ ID NO: 38, the LCDR2 comprises or consists of an amino acid sequence set forth in SEQ ID NO: 39, and the LCDR3 comprises or consists of an amino acid sequence set forth in SEQ ID NO: 44.

In a preferred embodiment, the present invention provides an anti-CD47 antibody or an antigen-binding fragment thereof, wherein the HCDR1 comprises or consists of an amino acid sequence set forth in SEQ ID NO: 20, the HCDR2 comprises or consists of an amino acid sequence set forth in SEQ ID NO: 30, and the HCDR3 comprises or consists of an amino acid sequence set forth in SEQ ID NO: 35; the LCDR1 comprises or consists of an amino acid sequence set forth in SEQ ID NO: 38, the LCDR2 comprises or consists of an amino acid sequence set forth in SEQ ID NO: 39, and the LCDR3 comprises or consists of an amino acid sequence set forth in SEQ ID NO: 44.

In some embodiments, the anti-CD47 antibodies or the antigen-binding fragments thereof of the present invention comprise a heavy chain variable region (HCVR), which comprises or consists of an amino acid sequence that has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or 100% identity with an amino acid sequence selected from SEQ ID NOs: 45, 46, 47, 48, 49, 50, 51, 52, 53 and 54. In some embodiments, the heavy chain variable region (HCVR) of the anti-CD47 antibodies comprises an amino acid sequence having one or more substitutions (such as conservative substitutions), insertions or deletions relative to the amino acid sequence selected from SEQ ID NOs: 45, 46, 47, 48, 49, 50, 51, 52, 53 and 54, but the anti-CD47 antibodies comprising the HCVR can bind to CD47.

In some embodiments, the anti-CD47 antibodies or the antigen-binding fragments thereof of the present invention comprise a light chain variable region (LCVR), which comprises or consists of an amino acid sequence that has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or 100% identity with an amino acid sequence selected from SEQ ID NOs: 65, 66, 67 and 68. In some embodiments, the light chain variable region (LCVR) of the anti-CD47 antibodies comprises an amino acid sequence having one or more substitutions (such as conservative substitutions), insertions or deletions relative to the amino acid sequence selected from SEQ ID NOs: 65, 66, 67 and 68, but the anti-CD47 antibodies comprising the LCVR can bind to CD47.

In some embodiments, the anti-CD47 antibodies or the antigen-binding fragments thereof of the present invention comprise a heavy chain variable region (HCVR) and a light chain variable region (LCVR), wherein the heavy chain variable region (HCVR) comprises or consists of an amino acid sequence that has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or 100% identity with an amino acid sequence selected from SEQ ID NOs: 45, 46, 47, 48, 49, 50, 51, 52, 53 and 54; and the light chain variable region (LCVR) comprises or consists of an amino acid sequence that has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or 100% identity with an amino acid sequence selected from SEQ ID NOs: 65, 66, 67 and 68.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 45; and a light chain variable region (LCVR) comprises or consists of an amino acid sequence set forth in SEQ ID NO: 65.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 46; and a light chain variable region (LCVR) comprises or consists of an amino acid sequence set forth in SEQ ID NO: 65.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 47; and a light chain variable region (LCVR) comprises or consists of an amino acid sequence set forth in SEQ ID NO: 65.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 48; and a light chain variable region (LCVR) comprises or consists of an amino acid sequence set forth in SEQ ID NO: 66.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 49; and a light chain variable region (LCVR) comprises or consists of an amino acid sequence set forth in SEQ ID NO: 66.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 50; and a light chain variable region (LCVR) comprises or consists of an amino acid sequence set forth in SEQ ID NO: 66.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 51; and a light chain variable region (LCVR) comprises or consists of an amino acid sequence set forth in SEQ ID NO: 67.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 52; and a light chain variable region (LCVR) comprises or consists of an amino acid sequence set forth in SEQ ID NO: 67.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 53; and a light chain variable region (LCVR) comprises or consists of an amino acid sequence set forth in SEQ ID NO: 68.

In a preferred embodiment, the present invention provides an anti-CD47 antibody or an antigen-binding fragment thereof, wherein a heavy chain variable region (HCVR) comprises or consists of an amino acid sequence set forth in SEQ ID NO: 54; and a light chain variable region (LCVR) comprises or consists of an amino acid sequence set forth in SEQ ID NO: 68.

In some embodiments, the anti-CD47 antibodies or the antigen-binding fragments thereof of the present invention comprise heavy chains, wherein each heavy chain comprises or consists of an amino acid sequence that has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or 100% identity with an amino acid sequence selected from SEQ ID NOs: 1, 3, 4, 5, 7, 8, 9, 11, 12 and 14. In some embodiments, each heavy chain of the anti-CD47 antibodies comprises an amino acid sequence having one or more substitutions (such as conservative substitutions), insertions or deletions relative to the amino acid sequence selected from SEQ ID NOs: 1, 3, 4, 5, 7, 8, 9, 11, 12 and 14, but the anti-CD47 antibodies comprising the heavy chains can bind to CD47.

In some embodiments, the anti-CD47 antibodies or the antigen-binding fragments thereof of the present invention comprise light chains, wherein each light chain comprises or consists of an amino acid sequence that has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or 100% identity with an amino acid sequence set forth in SEQ ID NOs: 2, 6, 10 or 13. In some embodiments, the light chain of the anti-CD47 antibodies comprises an amino acid sequence having one or more substitutions (such as conservative substitutions), insertions or deletions relative to an amino acid sequence selected from SEQ ID NOs: 2, 6, 10, and 13, but the anti-CD47 antibodies comprising the light chains can bind to CD47.

In some embodiments, the anti-CD47 antibodies or the antigen-binding fragments thereof of the present invention comprise heavy chains and light chains, wherein the heavy chain comprises or consists of an amino acid sequence that has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or 100% identity with an amino acid sequence selected from SEQ ID NOs: 1, 3, 4, 5, 7, 8, 9, 11, 12 and 14; and the light chain comprises or consists of an amino acid sequence that has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or 100% identity with an amino acid sequence set forth in SEQ ID NOs: 2, 6, 10 or 13.

In a preferred embodiment, the present invention provides an anti-CD47 antibody or an antigen-binding fragment thereof, wherein the heavy chain comprises or consists of an amino acid sequence set forth in SEQ ID NO: 1; and the light chain comprises or consists of an amino acid sequence set forth in SEQ ID NO: 2.

In a preferred embodiment, the present invention provides an anti-CD47 antibody or an antigen-binding fragment thereof, wherein the heavy chain comprises or consists of an amino acid sequence set forth in SEQ ID NO: 3; and the light chain comprises or consists of an amino acid sequence set forth in SEQ ID NO: 2.

In a preferred embodiment, the present invention provides an anti-CD47 antibody or an antigen-binding fragment thereof, wherein the heavy chain comprises or consists of an amino acid sequence set forth in SEQ ID NO: 4; and the light chain comprises or consists of an amino acid sequence set forth in SEQ ID NO: 2.

In a preferred embodiment, the present invention provides an anti-CD47 antibody or an antigen-binding fragment thereof, wherein the heavy chain comprises or consists of an amino acid sequence set forth in SEQ ID NO: 5; and the light chain comprises or consists of an amino acid sequence set forth in SEQ ID NO: 6.

In a preferred embodiment, the present invention provides an anti-CD47 antibody or an antigen-binding fragment thereof, wherein the heavy chain comprises or consists of an amino acid sequence set forth in SEQ ID NO: 7; and the light chain comprises or consists of an amino acid sequence set forth in SEQ ID NO: 6.

In a preferred embodiment, the present invention provides an anti-CD47 antibody or an antigen-binding fragment thereof, wherein the heavy chain comprises or consists of an amino acid sequence set forth in SEQ ID NO: 8; and the light chain comprises or consists of an amino acid sequence set forth in SEQ ID NO: 6.

In a preferred embodiment, the present invention provides an anti-CD47 antibody or an antigen-binding fragment thereof, wherein the heavy chain comprises or consists of an amino acid sequence set forth in SEQ ID NO: 9; and the light chain comprises or consists of an amino acid sequence set forth in SEQ ID NO: 10.

In a preferred embodiment, the present invention provides an anti-CD47 antibody or an antigen-binding fragment thereof, wherein the heavy chain comprises or consists of an amino acid sequence set forth in SEQ ID NO: 11; and the light chain comprises or consists of an amino acid sequence set forth in SEQ ID NO: 10.

In a preferred embodiment, the present invention provides an anti-CD47 antibody or an antigen-binding fragment thereof, wherein the heavy chain comprises or consists of an amino acid sequence set forth in SEQ ID NO: 12; and the light chain comprises or consists of an amino acid sequence set forth in SEQ ID NO: 13.

In a preferred embodiment, the present invention provides an anti-CD47 antibody or an antigen-binding fragment thereof, wherein the heavy chain comprises or consists of an amino acid sequence set forth in SEQ ID NO: 14; and the light chain comprises or consists of an amino acid sequence set forth in SEQ ID NO: 13.

In some embodiments, the antibody of the present invention also encompasses variants of the amino acid sequences of the anti-CD47 antibodies, an antibody capable of competing with any of the aforementioned antibodies to bind to CD47, and an antibody capable of competing with any of the aforementioned antibodies to bind to the same epitope on CD47.

In some embodiments, the anti-CD47 antibody is a monoclonal antibody. In some embodiments, the anti-CD47 antibody is a humanized antibody. In some embodiments, the anti-CD47 antibody is a human antibody. In some embodiments, at least a portion of the framework sequences of the anti-CD47 antibodies is a human consensus framework sequence. In one embodiment, the anti-CD47 antibody of the present invention also encompasses an antibody fragment thereof, preferably an antibody fragment selected from Fab, Fab'-SH, Fv, scFv and (Fab')2 fragment.

In some embodiments, the anti-CD47 antibody of the present invention is a blocking antibody for blocking the binding of CD47 to SIRPα.

In one aspect, the present invention provides a nucleic acid encoding any of the aforementioned anti-CD47 antibodies or fragments thereof. In one embodiment, a vector comprising the nucleic acid is provided. In one embodiment, the vector is an expression vector. In one embodiment, a host cell comprising the vector is provided. In one embodiment, the host cell is eukaryotic. In another embodiment, the host cell is selected from a yeast cell, a mammalian cell and other cells suitable for preparing an antibody or an antigen-binding fragment thereof. In another embodiment, the host cell is prokaryotic.

In one embodiment, the present invention provides a method for preparing an anti-CD47 antibody or a fragment thereof (preferably an antigen-binding fragment), wherein the method comprises culturing the host cell under conditions suitable for the expression of the nucleic acid encoding the antibody or the fragment thereof (preferably the antigen-binding fragment), and optionally isolating the antibody or the fragment thereof (preferably the antigen-binding fragment). In a certain embodiment, the method further comprises isolating the anti-CD47 antibody or the fragment thereof (preferably the antigen-binding fragment) from the host cell.

In one embodiment, the present invention provides an anti-CD47 antibody or a fragment thereof prepared by the method of the present invention.

In some embodiments, the present invention provides a composition comprising any of the anti-CD47 antibodies or the fragments thereof (preferably the antigen-binding fragments thereof) described herein, wherein, preferably, the composition is a pharmaceutical composition. In one embodiment, the composition further comprises pharmaceutically acceptable carriers.

In one aspect, the present invention relates to a method for inhibiting the binding of CD47 to SIRPα in a subject, wherein the method comprises administering to the subject an effective amount of any of the anti-CD47 antibodies or the fragments thereof described herein. The present invention also relates to a use of any of the anti-CD47 antibodies or the fragments thereof disclosed herein in the preparation of a composition or a drug for inhibiting the binding of CD47 to SIRPα in a subject.

In one aspect, the present invention relates to a method for promoting the phagocytosis by macrophages of a subject, wherein the method comprises administering to the subject an effective amount of any of the anti-CD47 antibodies or the fragments thereof described herein. The present invention also relates to a use of any of the anti-CD47 antibodies or the fragments thereof disclosed herein in the preparation of a composition or a drug for promoting the phagocytosis by macrophages of a subject. In one embodiment, compared with controls, the anti-CD47 antibodies of the present invention can increase the phagocytosis of macrophages by at least 10%, 20%, 30%, 40%, 50%, 60%, 70%, 80%, 90% or 100% or more than 100%.

In another aspect, the present invention relates to a method for treating CD47-related disorders of a subject, wherein the method comprises administering to the subject an effective amount of any of the anti-CD47 antibodies or the fragments thereof described herein. The present invention also relates to a use of any of the anti-CD47 antibodies or the fragments thereof disclosed herein in the preparation of a drug for treating CD47-related disorders of a subject.

In some embodiments, the CD47-related disorders may be various blood diseases and solid tumors, including but not limited to, acute myeloid leukemia (AML), chronic myeloid leukemia, acute lymphocytic leukemia (ALL), non-Hodgkin's lymphoma (NHL), multiple myeloma (MM), lymphoma, breast cancer, gastric cancer, lung cancer, esophageal cancer, intestinal cancer, ovarian cancer, cervical cancer, renal cancer, pancreatic cancer, bladder cancer, neuroglioma, melanoma, and other solid tumors.

In one aspect, the present invention relates to a CD47-targeted tumor immunotherapy method, wherein the method comprises administering to a subject an effective amount of any of the anti-CD47 antibodies or the fragments thereof described herein. The present invention also relates to a use of any of the anti-CD47 antibodies or the fragments thereof disclosed herein in the preparation of a drug for treating a tumor.

In one aspect, the present invention relates to a method for treating any disease or disorder capable of being improved, alleviated, inhibited or prevented by eliminating, inhibiting, or reducing the activity of CD47.

In another aspect, the method of the present invention also relates to a method for treating a tumor by a combination therapy, wherein the method comprises administering to a subject an effective amount of any of the anti-CD47 antibodies or the fragments thereof described herein in combination with one or more other drugs. In some embodiments, the method disclosed herein further comprises administering to the subject an effective amount of a second drug in a combination therapy, wherein the anti-CD47 antibody or the fragment disclosed herein is a first drug. In one embodiment, the second drug may be a chemotherapeutic agent, a radiotherapeutic agent or a biomacromolecular drug for treating the related diseases. In one embodiment, the biomacromolecular drug, for example, is one of the various monoclonal antibody drugs attacking tumor cells by T cell recognition, such as rituximab, cetuximab and trastuzumab. The expression "second drug" used herein does not mean that it is the only drug other than the first drug. Therefore, the second drug is not necessarily one drug, but may consist of or comprise more than one such drug.

In some embodiments, the subject or individual is a mammal, preferably a human.

In some embodiments, the anti-CD47 antibodies or the antigen-binding fragments provided herein can effectively promote the phagocytosis by macrophages.

In a preferred embodiment, it has been surprisingly found that the anti-CD47 antibodies or the antigen-binding fragments provided herein can effectively inhibit the growth of tumors compared with control antibodies.

In a more preferred embodiment, the anti-CD47 antibodies or the antigen-binding fragments provided herein can effectively promote the phagocytosis of tumor cells by macrophages in vitro, which is completely unexpected and has never been reported in the prior art.

In one aspect, the present invention relates to a method for detecting CD47 proteins in a sample, wherein the method comprises (a) contacting the sample with any of the anti-CD47 antibodies or the fragments thereof described herein, and (b) detecting the formation of a complex of the antibody CD47 or the fragment thereof with the CD47 proteins. In certain embodiments, the CD47 is a human CD47. In one embodiment, the detection method may be an in vitro or in vivo method. In one embodiment, the anti-CD47 antibody is used to select a subject suitable for treatment with the anti-CD47 antibody. In one embodiment, the anti-CD47 antibody is detectably labeled.

In another aspect, the present invention relates to a method for determining the effectiveness of a cancer therapy, which comprises measuring the numbers of cancer cells expressing CD47 in a sample from a subject before and after a treatment, wherein the reduction of the cancer cells expressing CD47 subsequent to the treatment indicates that the therapy is effective.

The present invention also involves any combination of the embodiments described herein. Any of the embodiments described herein, or any combination thereof, is applicable to any and all of the anti-CD47 antibodies or the fragments thereof, the methods, and the use described herein.

DETAILED DESCRIPTION

1.1. Definitions

Figure 1:
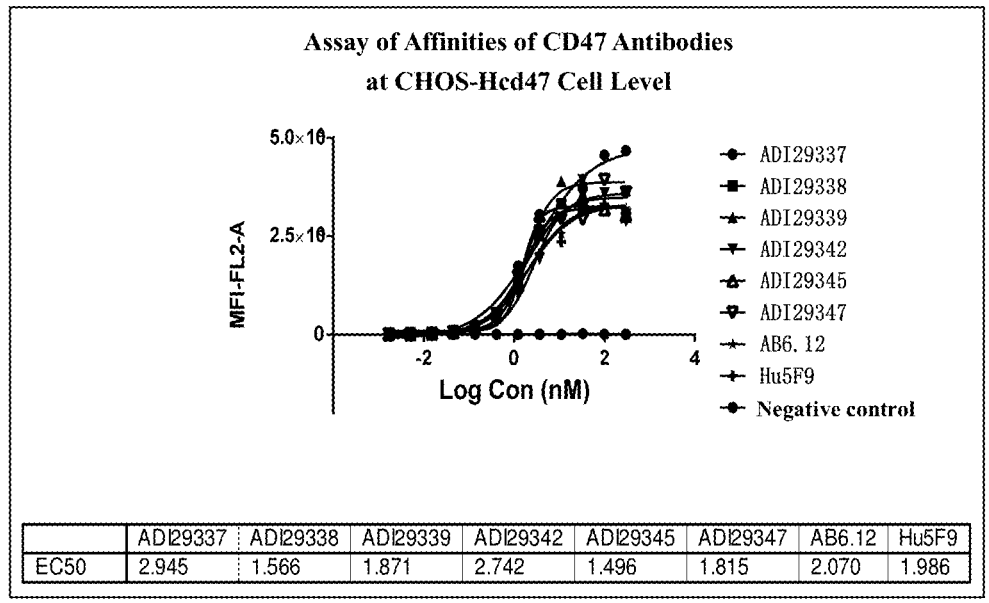
FIG. 1 shows an assay of affinities of anti-CD47 antibodies at cell levels.

Before the present invention is described in detail below, it should be understood that the present invention is not limited to the particular methodology, protocols, and reagents described herein, as these may vary. It should also be understood that the terminology used herein is only intended to describe specific embodiments rather than limit the scope of the present invention, which will be limited only by the appended claims. Unless otherwise defined, all technical and scientific terms used herein have the same meanings as commonly understood by those of ordinary skill in the art to which the present invention belongs.

For the purpose of explaining this specification, the following definitions will be used, and wherever appropriate, terms used in the singular form may also include the plural form, and vice versa. It should be understood that the terminology used herein is for the purpose of describing particular embodiments only, and is not intended to be limiting.

The term "about" used in combination with a numerical value is intended to encompass the numerical values in a range from a lower limit less than the specified numerical value by 5% to an upper limit greater than the specified numerical value by 5%.

The term "conservative substitution" refers to a substitution of an amino acid by another amino acid of the same class, for example, the substitution of an acidic amino acid by another acidic amino acid, the substitution of a basic amino acid by another basic amino acid, or the substitution of a neutral amino acid by another neutral amino acid. Exemplary substitutions are shown in Table 1 below:

TABLE I

| Primitive residue | Exemplary replacement | Preferred replacement |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Wal; Met; Ala; Phe; Nle | Leu |
| Leu (L) | Nle; le; Val; Met; Ala; Val; Phe | Ile |
| Lys (K) | Arg; Gln; Asn | Arg |
| Met (M) | Leu; Phe; Ile | Leu |
| Phe (F) | Trp: Leu; Val; lle; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe: Ala; Nle | Leu |

The term "antibody" is used herein in the broadest sense and encompasses a variety of antibody structures, including but not limited to monoclonal antibody, polyclonal antibody, multispecific antibody (such as bispecific antibody), and antibody fragments, as long as they exhibit the desired antigen-binding activities. An intact antibody will generally comprise at least two full-length heavy chains and two full-length light chains, but may comprise less chains in some cases, for example, natural antibodies in a camel may only comprise heavy chains.

The term "antigen-binding portion" used herein refers to a portion specifically binding to a target antigen. The term includes antibodies and other natural molecules (such as receptors and ligands) or synthetic molecules (such as DARPins) capable of specifically binding to target antigens. In a preferred embodiment, the antigen-binding portion of the antibody of the present invention is an antibody fragment.

The terms "full-length antibody", "complete antibody" and "intact antibody" are used interchangeably herein to refer to an antibody having a substantially similar structure to a natural antibody structure or having a heavy chain that comprises an Fc region as defined herein.

As used herein, the term "monoclonal antibody" or "monoclonal antibody composition" refers to a preparation having an antibody molecule composed of a single amino acid rather than a method for producing it. Monoclonal antibodies or antigen-binding fragments thereof may be produced, for example, by hybridoma technology, recombinant technology, phage display technology, synthetic technology such as CDR grafting, or a combination of such or other technologies known in the art.

As used herein, the terms "binding" and "specific binding" refer to the binding of an antibody or an antigen-binding portion to an epitope in an in vitro assay, preferably in biological optical interferometry (ForteBio) adopting a purified wild-type antigen. In certain embodiments, when the antibodies or the antigen-binding portions preferably recognize target antigens thereof in a complex mixture of proteins and/or macromolecules, the antibodies or the antigen-binding portions are referred to as specific binding antigens.

Depending on the amino acid sequences of a heavy chain constant region of the antibodies, the antibodies are divided into "classes": IgA, IgD, IgE, IgG, and IgM, several of which can be further divided into subclasses, such as IgG1, IgG2, IgG3, IgG4, IgA1 and IgA2. Heavy chain constant regions corresponding to different antibody classes are referred to as α, δ, ε, γ, and μ, respectively. Light chain constant regions (CL) that can be found in all five antibody classes are referred to as κ and λ. In a full-length light chain and heavy chain, the variable region and the constant region are typically connected by a "J" region of about twelve or more amino acids, and the heavy chain further comprises a "D" region of about more than ten amino acids. See, for example, Fundamental Immunology, Ch. 7 (Paul, w. Eds., 2nd edition, Raven Press, N.Y. (1989)) which is incorporated herein by reference in its entirety for all purposes. A variable region of each light chain/heavy chain pair typically forms an antigen-binding site.

The term "variable region" or "variable domain" refers to a domain of a heavy chain or light chain of an antibody involved in the binding of the antibody to an antigen. Variable domains of heavy and light chains of natural antibodies typically have similar structures, wherein each domain comprises four conserved framework regions (FRs) and three complementarity determining regions. (See, for example, Kindt et al., Kuby Immunology, 6th ed., W. H. Freeman and Co., page 91 (2007)). A single VH or VL domain may be sufficient to provide antigen-binding specificity. In addition, a VH or VL domain from an antibody binding to a particular antigen can be used to isolate antibodies that bind to the antigen, so as to screen libraries of complementary VL or VH domains. See, for example, Portolano et al., J. Immunol., 150:880-887 (1993); Clarkson et al., Nature, 352:624-628 (1991).

Variable regions generally exhibit the same general structure of relatively conservative framework regions (FRs) connected by three highly variable regions, and the highly variable region is also referred to as "complementarity determining region" or "CDR region" or "CDR". CDRs from each pair of chains are generally aligned by the framework regions, so that the CDRs can bind to specific epitopes. A light chain variable region and a heavy chain variable region generally comprise domains FR1, CDR1, FR2, CDR2, FR3, CDR3, and 1-R4 from N-terminus to C-terminus.

"Complementarity determining region" or "CDR region" or "CDR" or "highly variable region" (used interchangeably herein with hypervariable region "HVR") is an amino acid region that mainly binds to an antigen epitope in a variable region of an antibody. The CDRs of the heavy and light chains are generally referred to as CDR1, CDR2, and CDR3, which are numbered sequentially from N-terminus. The CDRs located in the heavy chain variable domain of the antibody are referred to as HCDR1, HCDR2 and HCDR3, whereas the CDRs located in the light chain variable domain of the antibody are referred to as LCDR1, LCDR2 and LCDR3.

A variety of schemes for determining CDR sequences of a given VH or VL amino acid sequence are well-known in the art: a Kabat complementarity determining region (CDR) is determined based on sequence variability, and is most commonly used (Kabat et al., Sequences of Proteins of Immunological Interest, 5th edition, Public Health Service, National Institutes of Health, Bethesda, Md. (1991)); a Chothia scheme is based on the positions of structural loops (Chothia et al., (1987) J. Mol. Biol. 196:901-917; Chothia et al. (1989) Nature 342: 877-883); and AbM HVR is a compromise between the Kabat HVR and the Chothia structural loop, and is used by AbM antibody modeling software (Oxford Molecular), and a "contact" HVR is based on the analysis of an obtainable complex crystal structure. According to different CDR determination schemes, the residue of each HVR/CDR among these HVRs is described as follows.

| CDR | Kabat scheme | AbM scheme | Chothia scheme | Contact scheme |
|---|---|---|---|---|
| | (Kabat numbering system) | | | |
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |
| | (Chothia numbering system) | | | |
| HCDR1 | H31-H35 | H26-H35 | H26-H32 | H30-H35 |
| | (Kabat numbering system) | | | |
| HCDR2 | H50-H65 | H50-H58 | H53-H55 | H47-H58 |
| HCDR3 | H95-H102 | H95-H102 | H96-H101 | H93-H101 |

The exact boundary of CDRs of the antibody of the present invention can be determined according to any scheme in the art or a combination thereof, and according to human evaluation.

Antibodies with different specificities (i.e., different binding sites for different antigens) have different CDRs. However, although CDRs differ from antibody to antibody, only a limited number of amino acid positions within the CDRs are directly involved in antigen binding. The smallest overlapping region can be determined using at least two of the Kabat, Chothia, AbM, and Contact schemes, thereby providing a "minimal binding unit" for antigen binding. The minimal binding unit may be a sub-portion of the CDR. As will be clear to those skilled in the art, residues of the rest CDR sequences can be determined via antibody structure and protein folding. Therefore, any variants of the CDRs given herein are also considered in the present invention. For example, in a CDR variant, the amino acid residues in the minimal binding unit may remain unchanged, while the other CDR residues defined by Kabat or Chothia may be substituted by conservative amino acid residues.

In some embodiments, the antibodies of the present invention comprise at least one, two, three, four, five, or six CDRs identical to the corresponding CDRs of any one of the antibodies listed in Table 3, or variants thereof. In some embodiments, the antibodies of the present invention comprise at least one, two, or three HCDRs identical to the corresponding heavy chain CDRs of any one of the antibodies listed in Table 3, or variants thereof. In some embodiments, the antibodies of the present invention comprise at least one, two, or three HCDRs identical to the corresponding light chain CDRs of any one of the antibodies listed in Table 3, or variants thereof. Herein, "corresponding CDRs" refer to CDRs located at substantially similar positions in the amino acid sequence of a variable region. Herein, a CDR variant is a CDR that has been modified by at least one, for example, one or two or three amino acid substitutions, deletions, and/or insertions, wherein an antigen-binding molecule comprising the CDR variant substantially retains the biological properties of the antigen-binding molecule comprising the unmodified CDRs, e.g., retains at least 60%, 70%, 80%, 90%, or 100% of the biological activity (e.g., antigen-binding ability). It is understood that each CDR may be modified independently or in combination. Preferably, an amino acid modification is an amino acid substitution, particularly a conservative amino acid substitution, such as a preferred conservative amino acid replacement listed in the specification.

"Antibody fragment" refers to a molecule different from an intact antibody, which comprises a portion of the intact antibody, and the portion binds to an antigen to which the intact antibody binds.

"Affinity" refers to the strength of the sum of all non-covalent interactions between a single binding site of a molecule (such as an antibody) and its binding partner (such as an antigen). Unless otherwise stated, when used herein, "binding affinity" refers to the intrinsic binding affinity that reflects a 1:1 interaction between members of a bound pair (such as an antibody and an antigen). The affinity of a molecule X for its partner Y can be generally represented by an equilibrium dissociation constant ($K_D$), which is the ratio of a dissociation rate constant to an association rate constant ($k_{dis}$ and $k_{on}$, respectively). Affinity can be measured by common methods known in the art, including those known in the prior art and described herein.

When used in the case of the antigen-binding proteins (such as neutral antigen-binding proteins or neutral antibodies) competing for the same epitope, the term "compete" refers to the competition between the antigen-binding proteins assayed by the assay method in which an antigen-binding protein to be assayed (such as an antibody or an immunologically functional fragment) prevents or inhibits (for example, reduces) the specific binding of a reference antigen-binding protein (such as a ligand or a reference antibody) to a common antigen (such as CD47 or a fragment thereof). Numerous types of competitive binding assays can be used to determine whether an antigen-binding protein competes with another, such as direct or indirect solid-phase radioimmunoassay (RIA), direct or indirect solid-phase enzyme immunoassay (EIA), and sandwich competition assay (see, for example, Stahli et al., 1983, Methods in Enzymology 9: 242-253). Generally, the assay method relates to a use of a purified antigen binding to a solid surface or a cell bearing an unlabeled assayed antigen-binding protein and a labeled reference antigen-binding protein. Competitive inhibition is measured by measuring the amount of label bound with the solid surface or the cell in the presence of the assayed antigen-binding protein. Generally, the assayed antigen-binding protein exists in an excessive amount. Antigen-binding proteins identified by the competitive assay (competitive antigen-binding proteins) include an antigen-binding protein binding to the same epitope as a reference antigen-binding protein, and an antigen-binding protein binding to an adjacent epitope sufficiently close to a binding epitope of the reference antigen-binding protein, and the two epitopes spatially interfere with each other to prevent the binding. Other detailed information regarding the method for assaying competitive binding is provided in the examples herein. Generally, when the competitive antigen-binding protein exists in an excessive amount, the specific binding of the reference antigen-binding protein to the common antigen will be inhibited (such as reduced) by at least 40-45%, 45-50%, 50-55%, 55-60%, 60-65%, 65-70%, 70-75% or 75% or more. In some cases, the binding will be inhibited by at least 80-85%, 85-90%, 90-95%, 95-97% or 97% or more.

"Human antibody" refers to an antibody having an amino acid sequence which corresponds to the amino acid sequence of an antibody generated by a human or human cell or derived from a non-human source that utilizes human antibody libraries or other human antibody coding sequences. This definition of a human antibody explicitly excludes humanized antibodies comprising non-human antigen-binding residues.

"Human consensus framework" refers to a framework which represents the most common amino acid residues in the selection of human immunoglobulin VL or VH framework sequences. Generally, the selection of human immunoglobulin VL or VH sequences is a selection from subtypes of variable domain sequences. Generally, the subtype of the sequence is a subtype disclosed in Kabat et al., *Sequences of Proteins of Immunological Interest,* 5th edition, NIH Publication 91-3242, Bethesda Md. (1991), Volumes 1-3. In one embodiment, for VLs, the subtype is the subtype κI as in Kabat et al. (see above). In one embodiment, for VHs, the subtype is the subtype III as in Kabat et al. (see above).

"Humanized" antibody refers to a chimeric antibody comprising amino acid residues from non-human HVRs and amino acid residues from human FRs. In some embodiments, a humanized antibody will comprise substantially all of at least one, typically two variable domains, wherein all or substantially all HVRs (such as CDRs) correspond to those of a non-human antibody, and all or substantially all FRs correspond to those of a human antibody. A humanized antibody may optionally comprise at least a portion of an antibody constant region derived from a human antibody. The "humanized form" of an antibody (such as a non-human antibody) refers to an antibody that has been humanized.

The term "diabodies" refers to an antibody fragment having two antigen-binding sites, and the fragment comprises a heavy chain variable domain (VH) linked to a light chain variable domain (VL) in one polypeptide chain (VH-VL). By using a linker that is too short for pairing two domains in one chain, the domains are forced to pair with the complementary domains of another chain to form two antigen-binding sites. Diabodies can be bivalent or bispecific. Diabodies are described in greater detail in, e.g., EP 404,097; WO 1993/01161; Hudson et al., Nat. Med. 9:129-134 (2003); and Hollinger et al., Proc. Natl. Acad. Sci. USA, 90:6444-6448 (1993). Tribodies and tetrabodies are also described in Hudson et al., Nat. Med. 9:129-134 (2003).

"Effector function" refers to biological activities which can be attributed to the antibody Fc region and vary with the antibody isotype. Examples of antibody effector functions include: C1q binding and complement-dependent cytotoxicity (CDC), Fc receptor binding, antibody-dependent cell-mediated cytotoxicity (ADCC), phagocytosis, cell surface receptors (such as B cell receptors) down-regulation, and B cell activation.

The term "effective amount" or "therapeutically effective amount" refers to such an amount or dosage of the antibody or antigen-binding fragment of the present invention that generates expected effects in a treated subject after administration to the subject at a single or multiple doses, including improvement of conditions of the subject (such as improvement of one or more symptoms) and/or delay of symptomatic progression. "Effective amount" or "therapeutically effective amount" may also refer to an amount enough to reduce CD47 signals (see, for example, Yamauchi et al., 2013 Blood, January 4; Soto-Pantoja et al., 2013 *Expert Opin Ther Targets*, 17: 89-103; Irandoust et al., 2013 *PLoS One*, Epub January 8; Chao et al., 2012 *Curr Opin Immunol*, 24:225-32; Theocharides et al., 2012 *J Exp Med*, 209 (1 0): 1883-99), such as an antibody amount enough to reduce phagocyte inhibition signals generated by the interaction of CD47/SIRPα on the CD47/SIRPα signaling axis in macrophages, that is, the antibodies of the present invention promote the macrophage-mediated phagocytosis of cells expressing CD47.

In one embodiment, compared with controls, an effective amount of CD47 antibodies of the present invention can promote/increase the phagocytosis of macrophages by 10%, 20%, 30%, 40%, 50%, 60%, 70%, 80%, 90% or 100%.

The effective amount can be easily determined by an attending physician as a person skilled in the art by considering a variety of factors as follows: species such as mammals; its size, age, and general health condition; the specific disease involved; the extent or severity of the disease; response in an individual patient; specific antibody administered; route of administration; bioavailability characteristics of the administered formulation; selected dosage regimen; and use of any concomitant therapy.

As described above, in some cases, the interaction between an antibody and a target antigen thereof will interfere with the function of a target. The amount required for administration further depends on the binding affinity of an antibody to a specific antigen thereof, as well as the clearance rate of the antibody given in a subject receiving administration. As a non-limiting example, the common range of the therapeutically effective amount of the antibodies or antibody fragments of the present invention is from about 0.1 mg/kg body weight to about 100 mg/kg body weight. In some embodiments, the antibodies of the present invention are administered to a subject at 0.1 mg/kg, 0.5 mg/kg, 1 mg/kg, 2 mg/kg, 5 mg/kg, 10 mg/kg, 15 mg/kg, 20 mg/kg, 25 mg/kg, 30 mg/kg, 50 mg/kg, 75 mg/kg, 100 mg/kg, or a higher dose. A common range of dose frequency is, for example, twice every day to once every week, once every two weeks, once every three weeks, once every month, once every two months, once every three months, and once every half a year.

The term "block" used herein means that the CD47 signaling is reduced in the presence of the antibodies of the present invention. CD47-mediated signaling blocking means that the CD47 signaling level in the presence of the CD47 antibodies of the present invention is lower than a control level of CD47 (i.e., a CD47 signaling level in the absence of antibodies), and the decrease is greater than or equal to 5%, 10%, 20%, 25%, 30%, 40%, 50%, 60%, 70%, 75%, 80%, 90%, 95%, 99%, or 100%. A variety of standard techniques can be employed to measure the CD47 signaling level, e.g., as a non-limiting example, a luciferase reporter assay that measures downstream gene activation and/or response to CD47 activation. Those skilled in the art should understand that a variety of assays can be employed to measure the CD47 signaling level, including, for example, a commercially available kit.

The terms "host cell", "host cell line" and "host cell culture" are used interchangeably and refer to cells into which exogenous nucleic acids are introduced, including progenies of such cells. Host cells include "transformants" and "transformed cells", which include primary transformed cells and progenies derived therefrom, regardless of the number of passages. Progenies may not be exactly the same as parent cells in terms of nucleic acid content, and may contain mutations. Mutant progenies having the same function or biological activity that are screened or selected from the initially transformed cells are included herein.

The term "cytotoxic agent" used herein refers to a substance that inhibits or prevents the cell function and/or causes cell death or cell destruction.

The term "vector" used herein refers to a nucleic acid molecule capable of proliferating another nucleic acid to which it is linked. The term includes vectors that serve as self-replicating nucleic acid structures as well as vectors binding to the genome of a host cell into which they have been introduced. Some vectors are capable of directing the expression of a nucleic acid to which they are operably linked. Such vectors are called "expression vectors" herein.

An "immunoconjugate" is an antibody conjugated to one or more heterologous molecules, including but not limited to cytotoxic agents.

"Individual" or "subject" includes mammals. The mammals include, but are not limited to, domestic animals (e.g., cattle, goats, cats, dogs, and horses), primates (e.g., human and non-human primates such as monkeys), rabbits, and rodents (e.g., mice and rats). In some embodiments, the individual or subject is a human.

An "isolated" antibody is an antibody which has been separated from components of its natural environment. In some embodiments, the antibody is purified to a purity greater than 95% or 99% as determined by, e.g., electrophoresis (e.g., SDS-PAGE, isoelectric focusing (IEF), capillary electrophoresis) or chromatography (e.g., ion exchange or reversed phase HPLC). For a review of methods for assessing antibody purity, see, for example, Flatman et al., J. Chromatogr., B848:79-87 (2007).

An "isolated" nucleic acid is a nucleic acid molecule which has been separated from components of its natural environment. The isolated nucleic acid includes a nucleic acid molecule contained in a cell that typically comprises the nucleic acid molecule, but the nucleic acid molecule exists extrachromosomally or at a chromosomal location that is different from its natural chromosomal location.

An "isolated nucleic acid encoding an anti-CD47 antibody or an antigen-binding fragment thereof" refers to one or more nucleic acid molecules encoding the heavy chain or light chain of the antibodies (or antigen-binding fragments thereof), including such a nucleic acid molecule in a single vector or separated vectors and such a nucleic acid molecule existing at one or more positions in a host cell.

The "percent (%) amino acid sequence identity" relative to a reference polypeptide sequence is defined as the percentage of the same amino acid residues in the candidate sequence and the reference polypeptide sequence after aligning the sequences (with gaps introduced if necessary) to achieve maximum percent sequence identity and without considering any conservative substitution as part of sequence identity. Various methods in the art can be employed to perform sequence alignment so as to determine the percent amino acid sequence identity, for example, using computer software available to the public, such as BLAST, BLAST-2, ALIGN or MEGALIGN (DNASTAR) software. Those skilled in the art can determine suitable parameters for measuring alignment, including any algorithm required to obtain maximum alignment for the full length of the aligned sequences.

Unless otherwise stated, percentages of sequence identity are calculated relative to the full length of long sequences when mentioned in the present invention. The calculation relative to the full length of long sequences is applicable to both nucleic acid sequences and polypeptide sequences.

The terms "red blood cell" and "erythrocyte" are synonyms and can be used interchangeably.

The term "agglutination" refers to cell agglomeration, while the term "hemagglutination" refers to a specific cell (i.e., red blood cell) agglomeration. Therefore, the hemagglutination is a type of the agglutination.

1.2 Anti-CD47 Antibodies of the Present Invention

Unless otherwise stated, the terms "integrin-associated protein (IAP)" and "CD47" used herein refer to any natural CD47 from any vertebrate, including mammals, such as primates (e.g., humans), and rodents (e.g., mice and rats). The terms encompass "full-length", unprocessed CD47 and CD47 in any form resulting from intracellular processing or any fragment thereof. The terms also include variants of naturally existing CD47, such as splicing variants or allelic variants.

The term "anti-CD47 antibody", "anti-CD47", "CD47 antibody" or "antibody binding to CD47" refers to an antibody which can bind to a CD47 protein or a fragment thereof with sufficient affinity so as to serve as a diagnostic agent and/or a therapeutic agent in targeting CD47. In one embodiment, the degree of the anti-CD47 antibody binding to an unrelated, non-CD47 protein is about 10% lower than that of the antibody binding to CD47, as measured, for example, by radioimmunoassay (RIA). In some embodiments, the dissociation constant ($K_D$) of the anti-CD47 antibodies provided herein is less than or equal to 1 µM, 100 nM, 10 nM, 1 nM, 0.1 nM, 0.01 nM, or 0.001 nM (e.g., no more than $10^{-8}$ M, $10^{-8}$ M to $10^{-13}$ M, and $10^{-9}$ M to $10^{-13}$ M).

In some embodiments, the anti-CD47 antibodies or the antigen-binding fragments provided herein comprise substitutions, insertions or deletions. In a preferred embodiment, substitutions, insertions or deletions occur in regions outside CDRs (for example, in FRs), and the biological properties of the antibody molecule prior to alteration are substantially retained. In one embodiment, at least 60%, 70%, 80%, 90% or 100% of the biological properties of the antibody molecule prior to alteration are retained. Optionally, the anti-CD47 antibodies of the present invention comprise post-translational modifications of light chain variable regions, heavy chain variable regions, light chains or heavy chains, which do not result in loss of the ability of antibody variants to bind to antigens, and optionally may impart properties such as increased antigen affinity and different effector functions.

The CD47 antibodies provided herein exhibit inhibitory activities, such as inhibiting the expression of CD47 (such as inhibiting the expression of CD47 on the surface of cells), inhibiting the activity and/or signaling, or interfering with the interaction between CD47 and SIRPα. The CD47 antibodies provided herein can completely or partially decrease or regulate the expression or activity of CD47 after binding to or interacting with CD47 (such as human CD47). After the antibodies interact with human CD47 polypeptides and/or peptides, the decrease or regulation of biological functions of CD47 is complete, significant or partial. When the expression or activity level of CD47 in the presence of the antibodies is decreased by at least 95% (such as 96%, 97%, 98%, 99%, or 100%) in comparison with the expression or activity level of CD47 in the absence of interaction (such as binding) with the antibodies described herein, the antibodies are believed to be able to completely inhibit the expression or activity of CD47. When the expression or activity level of CD47 in the presence of the CD47 antibodies is decreased by at least 50% (such as 55%, 60%, 75%, 80%, 85%, or 90%) in comparison with the expression or activity level of CD47 in the absence of binding to the CD47 antibodies described herein, the CD47 antibodies are believed to be able to significantly inhibit the expression or activity of CD47. When the expression or activity level of CD47 in the presence of the antibodies is decreased by less than 95% (such as 10%, 20%, 25%, 30%, 40%, 50%, 60%, 75%, 80%, 85%, or 90%) in comparison with the expression or activity level of CD47 in the absence of interaction (such as binding) with the antibodies described herein, the antibodies are believed to be able to partially inhibit the expression or activity of CD47.

In certain embodiments, one or more amino acid modifications may be introduced into an Fc region of an antibody provided herein, thus producing an Fc region variant. The Fc region variant may comprise human Fc region sequences (such as human IgG1, IgG2, IgG3 or IgG4 Fc regions) comprising amino acid modifications (such as substitutions) at one or more amino acid positions.

In certain embodiments, antibodies modified by cysteine engineering may need to be produced, such as "sulfo-MAb", wherein one or more residues of the antibodies are substituted by cysteine residues.

In certain embodiments, the antibodies provided herein can be further modified to comprise other non-protein portions known in the art and readily available. Suitable portions for antibody derivatization include, but are not limited to, water-soluble polymers. Non-limiting examples of water-soluble polymers include, but are not limited to, polyethylene glycol (PEG), ethylene glycol/propylene glycol copolymers, carboxymethyl cellulose, glucan, polyvinyl alcohol, polyvinylpyrrolidone, poly-1,3-dioxane, poly-1,3,6-trioxane, ethylene/maleic anhydride copolymer, polyamino acid (homopolymer or random copolymer), and glucan or poly(n-vinylpyrrolidone)polyethylene glycol, propylene glycol homopolymer, polypropylene oxide/ethylene oxide copolymer, polyoxyethylated polyol (such as glycerol), polyvinyl alcohol, and mixtures thereof.

In some embodiments, the present invention encompasses fragments of the anti-CD47 antibodies. Examples of the antibody fragments include but are not limited to Fv, Fab, Fab', Fab'-SH, F(ab')$_2$, diabodies, linear antibodies, single-chain antibody molecules (such as scFv), and multispecific antibodies formed by antibody fragments. An antibody is digested by papain to produce two identical antigen-binding fragments called "Fab" fragments, each having a single antigen-binding site, and residual "Fc" fragments, the name of which reflects its ability to crystallize easily. An F(ab')$_2$ fragment having two antigen-binding sites and still being capable of cross-linking with an antigen is produced by treatment of pepsin.

In some embodiments, the anti-CD47 antibody of the present invention is a humanized antibody. Different methods for humanizing antibodies are known to those skilled, as summarized by Almagro & Fransson, the content of which is incorporated in its entirety herein by reference (Almagro J. C. and Fransson J (2008) Frontiers in Bioscience 13:1619-1633). Almagro & Fransson distinguishes between rational approach and empirical approach. The rational approach is characterized by generating a small number of engineered antibody variants and assessing their binding or any other characteristics of interest. If the designed variants do not produce expected results, a new round of design and combined evaluation will be launched. The rational approach includes CDR grafting, resurfacing, superhumanization, and human string content optimization. In contrast, the empirical approach is based on generating large humanized variant libraries, and selects the best clones using enrichment techniques or high-throughput screening. Thus, the empirical approach depends on a reliable selection and/or screening system capable of searching for a large number of antibody variants. In vitro display technologies such as phage display and ribosome display meet these requirements and are well known to those skilled. The empirical approach includes FR library construction, guided selection, framework-shuffling, and humaneering.

In some embodiments, the anti-CD47 antibody of the present invention is a human antibody. The human antibody can be prepared using a variety of techniques known in the art. The human antibody is generally described in van Dijk and van de Winkel, Curr: Opin. Pharmacol 5:368-74(2001) and Lonberg, Curr. Opin. Immunol 20:450-459(2008).

The antibody of the present invention can be isolated by screening antibody having desired activities in a combinatorial library. For example, various methods for generating phage display libraries and screening the antibodies with desired binding characteristics in the libraries are known in the art. These methods are reviewed in, for example, Hoogenboom et al., Methods in Molecular Biology 178:1-37 (edited by O'Brien et al., Humana Press, Totowa, N.J., 2001), and are further described in, for example, McCafferty et al., Nature 348:552-554; Clackso et al., Nature 352:624-628(1991); Marks et al., J. Mol. Biol. 222:581-597(1992); Marks and Bradbury, Methods in Molecular Biology 248: 161-175 (edited by Lo, Humana Press, Totowa, N.J., 2003); Sidhu et al., J. Mol. Biol. 338(2):299-310(2004); Lee et al., J. Mol. Biol. 340(5):1073-1093(2004); Fellouse, Proc. Natl. Acad. Sci. USA 101(34):12467-12472(2004); and Lee et al., J. Immunol. Methods 284(1-2):119-132(2004).

"Antibodies and antigen-binding fragments" applicable to the present invention include but are not limited to polyclonal, monoclonal, monovalent, bispecific, isoconjugate, multispecific, recombinant, heterogenous, heterogeneous hybrid, chimeric, humanized (particularly CDR-grafted), deimmunized or human antibodies, Fab fragments, Fab' fragments, F(ab')$_2$ fragments, fragments produced by a Fab expression library, Fd, Fv, disulphide-linked Fv (dsFv), single-chain antibodies (such as scFv), diabodies or tetrabodies (Holliger P. et al. (1993) Proc. Natl. Acad. Sci. U.S.A. 90(14), 6444-6448), nanobodies (also referred to as single-domain antibodies), anti-idiotype (anti-Id) antibodies (including, for example, anti-Id antibodies against the antibodies of the present invention), and an epitope-binding fragment of any of the above.

In some embodiments, the antibody of the present invention may be monospecific, bispecific or multispecific. The multispecific monoclonal antibody may be specific to different epitopes of a target polypeptide or may comprise antigen-binding domains specific to more than one target polypeptide. See, for example, Tutt et al. (1991) J. Immunol. 147:60-69. The anti-CD47 monoclonal antibody may link to or co-expresses with another functional molecule (such as another peptide or protein). For example, the antibody or the fragment thereof may functionally link to one or more other molecules, such as another antibody or antibody fragment (for example, by chemical coupling, genetic fusion, non-covalent association, or other methods), to produce a bispecific or multispecific antibody having a second or more binding specificities.

In some embodiments, the antibody of the present invention binds to human CD47 protein.

1.3 Nucleic Acid and Host Cell Comprising The Same of The Present Invention

In one aspect, the present invention provides a nucleic acid encoding any of the aforementioned anti-CD47 antibodies or fragments thereof. The nucleic acid can encode an amino acid sequence comprising the light chain variable region and/or the heavy chain variable region of the antibody, or an amino acid sequence comprising the light chain and/or the heavy chain of the antibody.

In one embodiment, one or more vectors comprising the nucleic acid are provided. In one embodiment, the vector is an expression vector.

In one embodiment, a host cell comprising the vector is provided. The suitable host cell for cloning or expressing the vector encoding the antibody includes a prokaryocyte or a eukaryocyte described herein. For example, antibodies may be produced in bacteria, particularly when glycosylation and Fc effector functions are not required. Expression of an antibody fragment and a polypeptide in bacteria is described in, for example, U.S. Pat. Nos. 5,648,237, 5,789,199 and 5,840,523, and also described in Charlton, Methods in Molecular Biology, Vol. 248 (B. K. C. Lo, ed., Humana Press, Totowa, N.J., 2003), pg. 245-254, which describes expression of antibody fragments in *E. coli*. After expression, the antibody can be isolated from bacterial cell paste in soluble fraction and can be further purified.

In one embodiment, the host cell is eukaryotic. In another embodiment, the host cell is selected from a yeast cell, a mammalian cell and other cells suitable for preparing an antibody or an antigen-binding fragment thereof. For example, eukaryotic microorganisms, such as filamentous fungi or yeast, are suitable cloning or expression hosts for vectors encoding antibodies, including fungi and yeast strains, the glycosylation pathway of which has been "humanized", leading to the production of antibodies with partial or complete human glycosylation patterns. See Gerngross, Nat. Biotech. 22:1409-1414 (2004), and Li et al., Nat. Biotech. 24:210-215 (2006). Host cells suitable for expressing a glycosylated antibody are also derived from multicellular organisms (invertebrates and vertebrates). Vertebrate cells may also be used as hosts. For example, a mammalian cell line engineered to be suitable for suspension growth may be used. Other examples of useful mammalian host cell lines are a monkey kidney CV1 line (COS-7) transformed with SV40, a human embryonic kidney line (293 or 293 cells, as described in, for example, Graham et al., J. Gen Virol. 36:59(1977)), and the like. Other useful mammalian host cell lines include Chinese hamster ovary (CHO) cells, including DHFR-CHO cells (Urlaub et al., Proc. Natl. Acad. Sci. USA 77: 216 (1980)), and myeloma cell lines such as Y0, NS0, and Sp2/0. For reviews of certain mammalian host cell lines suitable for antibody production, see, e.g., Yazaki and Wu, Methods in Molecular Biology, Vol. 248 (B. K. C. Lo, ed., Humana Press, Totowa, N.J.), pg. 255-268 (2003).

In one embodiment, a method for preparing the anti-CD47 antibody is provided, wherein the method comprises culturing host cells comprising a nucleic acid encoding the antibody under a condition suitable for expressing antibody, as provided above, and optionally isolating the antibody from the host cells (or host cell media). For recombinant production of the anti-CD47 antibody, the nucleic acid encoding the antibody (such as the antibody described above) is isolated, and one or more vectors are inserted for further cloning and/or expression in the host cells. Such a nucleic acid can be easily isolated and sequenced by using conventional procedures (e.g., by using oligonucleotide probes that are capable of specifically binding to genes encoding heavy and light chains of antibodies).

1.4 Pharmaceutical Composition and Pharmaceutical Preparation

The present invention also provides a pharmaceutical composition comprising one or more monoclonal antibodies binding to CD47 or immunocompetent fragments thereof. It should be understood that the anti-CD47 antibodies or the pharmaceutical composition provided herein can be integrated into a suitable carrier, an excipient and other reagents in a preparation for combined administration, thus providing improved transfer, delivery, tolerability, etc.

The term "pharmaceutical composition" refers to a preparation which exists in a form allowing the biological activity of active ingredients contained therein to be effective, and does not contain additional ingredients that have toxicity unacceptable to a subject to which the composition is administered.

The term "pharmaceutically acceptable carrier" refers to diluents, adjuvants (such as Freund's adjuvants (complete and incomplete)), excipients or vehicles administered along with therapeutic agents.

When used herein, "treatment" refers to slowing, interrupting, blocking, alleviating, stopping, reducing or reversing the progression or severity of an existing symptom, disorder, condition or disease, and preventing the relapse of related disease.

In some embodiments, the present invention also encompasses an anti-CD47 monoclonal antibody (an "immunoconjugate") conjugated to a therapeutic module (such as a cytotoxic agent or an immunosuppressant). The cytotoxic agent includes any agent that is harmful to cells. Examples of the cytotoxic agent (such as a chemotherapeutic agent) suitable for forming the immunoconjugate are known in the art, see, for example, WO 05/103081. For example, the cytotoxic agent includes but is not limited to, radioisotopes (such as $At^{211}$, $I^{131}$, $I^{125}$, $Y^{90}$, $Re^{186}$, $Re^{188}$, $sm^{153}$, $Bi^{212}$, $p^{32}$, $pb^{212}$ and radioisotopes of Lu), chemotherapeutic agents or drugs (such as methotrexate, adriamicin, *vinca* alkaloids (vincristine, vinblastine and etoposide), doxorubicin, melphalan, mitomycin C, chlorambucil, daunorubicin or other intercalators), growth inhibitors, enzymes and fragments thereof (such as nucleic acid hydrolase), antibiotics, toxins (such as micromolecular toxins or enzymatic active toxins derived from bacteria, fungi, plants or animals), including fragments and/or variants thereof, and various known anti-tumor or anti-cancer agents.

The present invention also includes a composition (including a pharmaceutical composition or a pharmaceutical preparation) comprising an anti-CD47 antibody and a composition comprising a polynucleotide encoding the anti-47 antibody. In certain embodiments, the composition comprises one or more antibodies that bind to CD47 or one or more polynucleotides encoding the one or more antibodies that bind to CD47. These compositions may also comprise a suitable pharmaceutically acceptable carrier, such as a pharmaceutical excipient known in the art, including a buffer.

The pharmaceutical compositions of the present invention may comprise the antibody and pharmaceutically acceptable carrier of the present invention. These pharmaceutical compositions may be contained in a kit, such as a diagnostic kit.

The pharmaceutically acceptable carrier applicable to the present invention may be sterile liquid, such as water and oil, including those derived from petroleum, animals, plants or synthesis, such as peanut oil, soybean oil, mineral oil, sesame oil, etc. Water is a preferred carrier when the pharmaceutical composition is administered intravenously. Saline solutions, aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, etc. For use and application of excipients, see "Handbook of Pharmaceutical Excipients", 5th Edition, R. C. Rowe, P. J. Seskey and S. C. Owen, Pharmaceutical Press, London, Chicago. The compositions may further comprise a small quantity of wetting agents or emulsifiers, or pH buffer, if desired. The compositions may take the form of a solution, a suspension, an emulsion, a tablet, a pill, a capsule, a powder, a sustained release preparation, and the like. Oral preparations may comprise standard carriers, such as pharmaceutical grade mannitol, lactose, starch, magnesium stearate, and saccharin.

The pharmaceutical preparation comprising the anti-CD47 antibody described herein can be prepared by mixing the anti-CD47 antibody of the present invention having required purity with one or more optional pharmaceutically acceptable carriers (Remington's Pharmaceutical Sciences, 16th Edition, Osol, A. Ed. (1980)), preferably in the form of a lyophilized preparation or an aqueous solution.

An exemplary lyophilized antibody preparation is described in U.S. Pat. No. 6,267,958. The aqueous antibody preparation includes those described in U.S. Pat. No. 6,171,586 and WO 2006/044908, and the latter preparation comprises a histidine-acetate buffer.

The pharmaceutical composition or preparation of the present invention may also comprise more than one active ingredient which is required for a specific indication treated, and active ingredients having complementary activities that do not adversely affect one another are preferred. For example, it is desirable to further provide statin substances. The active ingredients are suitably combined in an amount effective for an intended purpose.

A sustained release preparation can be prepared. Suitable examples of the sustained release preparation include a semipermeable matrix of a solid hydrophobic polymer comprising an antibody. The matrix is in the form of a shaped article, such as a film or a microcapsule.

1.5 Therapeutic Method and Use of Antibodies

In one aspect, the present invention relates to a method for inhibiting or antagonizing the binding of CD47 to SIRPα in a subject, wherein the method comprises administering to the subject an effective amount of any of the anti-CD47 antibodies or the fragments thereof described herein. In another aspect, the present invention relates to a method for promoting the phagocytosis by phagocytes of a subject, wherein the method comprises administering to the subject an effective amount of any of the anti-CD47 antibodies or the fragments thereof described herein. In one aspect, the present invention relates to a method for treating CD47-targeted diseases, and the method comprises administering to the subject an effective amount of any of the anti-CD47 antibodies or the fragments thereof described herein. In one aspect, the present invention relates to a method for treating any disease or disorder capable of being improved, alleviated, inhibited or prevented by eliminating, inhibiting or reducing the binding of CD47 to SIRPα. In another aspect, the present invention provides a method for treating a cancer or tumor of a subject, a method for alleviating cancer or tumor symptoms of a subject, and a method for preventing a tumor or cancer relapse of a subject by administering the anti-CD47 antibodies or the fragments thereof disclosed herein to the subject in need.

In one aspect, the anti-CD47 antibodies and antigen-binding fragments thereof and the pharmaceutical composition comprising the same provided herein may be used as a therapeutic agent for diagnosis, prognosis, monitoring, treatment, alleviation and/or prevention of diseases and disorders related to abnormal expression, activity and/or signaling of CD47 in a subject. When a disease and a disorder related to abnormal expression, activity and/or signaling of CD47 in a subject are identified by using a standard method, the anti-CD47 antibodies and the antigen-binding fragments thereof and the pharmaceutical composition comprising the same disclosed herein may be administered.

In other aspects, the present invention provides uses of the anti-CD47 antibodies in the production or preparation of a medicament for treating the aforementioned related diseases or disorders.

In certain embodiments, the methods and the uses described herein further include administering to the individual an effective amount of at least one additional therapeutic agent, such as a chemotherapeutic agent, a radiotherapeutic agent or a biomacromolecular drug. In one embodiment, the biomacromolecular drug, for example, is one of the various monoclonal antibody drugs attacking tumor cells by T cell recognition, such as rituximab, cetuximab and trastuzumab.

The aforementioned combination therapy includes combined administration (wherein more than two therapeutic agents are contained in the same or separate preparations) and separate administration, wherein the administration of the anti-CD47 antibody of the present invention may be before, simultaneously with and/or after the administration of additional therapeutic agents and/or adjuvants.

The antibody of the present invention (and any additional therapeutic agent) can be administered by any suitable method, including parenteral administration, intrapulmonary administration, intranasal administration, and intralesional administration if required by local treatment. Parenteral infusion includes intramuscular, intravenous, intra-arterial, intraperitoneal or subcutaneous administration. The medicaments may be administered by any suitable means, such as injection, e.g., intravenous or subcutaneous injection, to some extent depending on short-term or long-term treatment. Various administration schedules are encompassed herein, including but not limited to single administration or multiple administrations at multiple time points, bolus administration and pulse infusion.

In order to prevent or treat diseases, the appropriate dosage of the antibody of the present invention (when used alone or in combination with one or more other additional therapeutic agents) will depend on types of diseases to be treated, types of antibodies, severity and progression of the disease, purpose of administration (prophylactic or therapeutic), previous treatments, clinical histories of patients, responses to the antibody, and the discretion of an attending physician. The antibody is suitably administered to a patient through a single treatment or through a series of treatments.

In another aspect, the antibody of the present invention can be used to assay the progression of treatment of a disease related to CD47 in vivo or in vitro, for example, it can be determined whether a certain specific therapy aiming at treating a disease and alleviating symptoms is effective or not by measuring an increase or decrease in the number of cells (such as cancer cells) expressing CD47.

Most of the CD47 antibodies have been reported to cause hemagglutination of human erythrocytes. Hemagglutination is an example of homotypic interaction in which the treatment of binding bivalent CD47 to an entity causes aggregation or agglutination of two cells expressing CD47. For example, as a full IgG or F(ab')$_2$, the CD47 antibody MABL has been reported to be capable of causing hemagglutination of erythrocytes, and this effect is weakened only when MABL becomes scFv or bivalent scFv (see, for example, Uno S, Kinoshita Y, Azuma Y et al., Antitumor activity of a monoclonal antibody against CD47 in xenograft models of human leukemia, Oncol Rep 2007; 17: 1189-94; Kikuchi Y, Uno S, Yoshimura Y et al., A bivalent single-chain Fv fragment against CD47 induces apoptosis for leukemic cells, Biochem Biophys Res Commun 2004; 315: 912-8). Other known CD47 antibodies (including B6H12, BRC126 and CC2C6) can also cause hemagglutination of RBCs. Therefore, the agglutination of cells is a main limitation for the use of existing full IgG antibodies in therapeutically targeting CD47.

Given that most of the antibodies disclosed in the prior art that block the interaction between CD47 and SIPRα to promote phagocytosis will cause a significant cell agglutination, there is still an urgent need at present to obtain a novel anti-CD 47 antibody that not only can effectively promote the phagocytosis of macrophages but also do not cause the cell agglutination. The antibodies disclosed herein meet the requirements in this aspect, which not only can effectively promote phagocytosis, but also have an excellent effect on inhibiting tumor growth and eliminating tumor, and the anti-CD47 antibodies disclosed herein do not significantly cause cell agglutination during a treatment, thus having significantly reduced side effects.

Those skilled in the art can quantify the level of agglutination through a routine experiment, such as the hemagglutination of RBCs. For example, those skilled in the art can perform a hemagglutination test in the presence of the CD47 antibody of the present invention, and then measure the area of RBC spots to determine the level of the hemagglutination, as described in the following examples. In some cases, the area of RBC spots in the presence of the CD47 antibody of the present invention is compared with the area of RBC spots in the absence of the CD47 antibody of the present invention (i.e., under a zero hemagglutination condition) and the area of RBC spots in the presence of other known CD47 antibodies. In this method, the hemagglutination is quantified relative to a baseline. The larger the area of RBC spots, the higher the level of the hemagglutination. Alternatively, a density analysis of RBC spots may also be employed to quantify the hemagglutination.

1.6 Methods and Compositions for Diagnosis and Detection

In certain embodiments, any of the anti-CD47 antibodies or antigen-binding fragments thereof provided herein can be used to detect the presence of CD47 in a biological sample. The term "detection" includes quantitative or qualitative detection when used herein. In certain embodiments, the biological sample is blood, serum, or other liquid samples of biological origin. In certain embodiments, the biological sample includes cells or tissues.

In certain embodiments, a labeled anti-CD47 antibody is provided. The label includes, but is not limited to, a label or moiety (e.g., a fluorescent label, a chromophoric label, an electron-dense label, a chemiluminescent label, and a radioactive label) that is detected directly, as well as a moiety that is detected indirectly, such as an enzyme or a ligand, for example, by an enzymatic reaction or a molecular interaction. Exemplary labels include, but are not limited to, radioisotopes of $^{32}P$, $^{14}C$, $^{125}I$, $^{3}H$ and $^{131}I$, fluorophores (such as rare earth chelates or fluorescein) and derivatives thereof, rhodamine and derivatives thereof, dansyl, umbelliferone, luceriferase (such as firefly luciferase and bacterial luciferase (U.S. Pat. No. 4,737,456)), fluorescein, 2,3-dihydrophthalazinedione, horseradish peroxidase (HR), alkaline phosphatase, β-galactosidase, glucoamylase, lysozyme, carbohydrate oxidase (such as glucose oxidase, galactose oxidase and glucose-6-phosphate dehydrogenase), heterocyclic oxidase (such as uricase and xanthine oxidase), enzymes oxidizing dye precursors with hydrogen peroxide (such as HR, lactoperoxidase, or microperoxidase), biotin/avidin, spin labels, phage labels, stable free radicals, etc.

The following examples further illustrate the present invention. However, it should be understood that the examples are described by way of illustration rather than limitation, and various modifications may be made by those skilled in the art.

1.7 Sequences of Exemplary Anti-CD47 Antibodies of the Present Invention

TABLE A

Sequences of Heavy Chain and Light Chain CDRs of Exemplary Antibodies of the Present Invention

| Antibody | HCDR1 | HCDR2 | HCDR3 | LCDR1 | LCDR2 | LCDR3 |
|---|---|---|---|---|---|---|
| ADI-29337 | GSINHYYWS (SEQ ID NO: 15) | AIYYSGSTRYNPSLKS (SEQ ID NO: 21) | ARGKSAFDP (SEQ ID NO: 31) | RASQGISRWLA (SEQ ID NO: 36) | AASSLQS (SEQ ID NO: 39) | QQADLHPPLT (SEQ ID NO: 41) |
| ADI-29338 | GSISSYYWS (SEQ ID NO: 16) | TIYYSGSTRYNPSLKS (SEQ ID NO: 22) | | | | |
| ADI-29339 | GSISHYYWS (SEQ ID NO: 17) | VIYYSGSTNYNPSLKS (SEQ ID NO: 23) | | | | |
| ADI-29342 | GSIMHYYWS (SEQ ID NO: 18) | YIYYSGSTNYNPSLKS (SEQ ID NO: 24) | ARGKTGSAA (SEQ ID NO: 32) | | | QQTVSFPIT (SEQ ID NO: 42) |
| ADI-29345 | GSISHYYWS (SEQ ID NO: 17) | YIYYSGVTTYNPSLKS (SEQ ID NO: 25) | ARGKTGSTA (SEQ ID NO: 33) | | | |
| ADI-29347 | GSIANYYWS (SEQ ID NO: 19) | YTYFSGSTNYNPSLKS (SEQ ID NO: 26) | ARGKTGSAA (SEQ ID NO: 32) | | | |
| ADI-26655 | GSISSYYWS (SEQ ID NO: 16) | YIYYSGTTYNPSLKS (SEQ ID NO: 27) | ARKKRFFDL (SEQ ID NO: 34) | RASQSISSWLA (SEQ ID NO: 37) | KASSLES (SEQ ID NO: 40) | QQVKSYSPLT (SEQ ID NO: 43) |
| ADI-29350 | GSIEHYYWS (SEQ ID NO: 20) | YIYYSGFTEYNPSLKS (SEQ ID NO: 28) | | | | |
| ADI-26660 | GSISSYYWS (SEQ ID NO: 16) | SIYYSGSTNYNPSLKS (SEQ ID NO: 29) | ARKQKHFDI (SEQ ID NO: 35) | RASQGISSWLA (SEQ ID NO: 38) | AASSLQS (SEQ ID NO: 39) | QQVNHHPWT (SEQ ID NO: 44) |
| ADI-29362 | GSIEHYYWS (SEQ ID NO: 20) | AIYYSGSTNYNPSLKS (SEQ ID NO: 30) | | | | |
| | GSIX$_1$X$_2$YYWS (wherein X$_1$ is selected from N, S, M, A, and E; and X$_2$ is selected from H, S, and N) (SEQ ID NO: 69) | X$_1$IYX$_2$SGX$_3$TX$_4$YNPSLKS (wherein X$_1$ is selected from A, T, V, Y, and S; X$_2$ is selected from Y and F; X$_3$ is selected from V, F, and S; and X$_4$ is selected from R, T, N, and E) (SEQ ID NO: 70) | | RASQX$_1$ISX$_2$WLA (wherein X$_1$ is selected from S and G; and X$_2$ is selected from S and R) (SEQ ID NO: 71) | X$_1$ASSLX$_2$S (wherein X$_1$ is selected from A and K; and X$_2$ is selected from Q and E) (SEQ ID NO: 72) | |

TABLE B

Sequences of Heavy Chain Variable Regions and Light Chain Variable Regions of Exemplary Antibodies of the Present Invention

| ADI Name | VH DNA | VH Protein | VL DNA | VL Protein |
|---|---|---|---|---|
| ADI-29337 | CAGGTGCAGCTGCAGGAGTCGGGCCCAGGACTGG TGAAGCCTTCGGAGACCCTGTCCCTCACCTGCACT GTCTCTGGTGGCTCCATCAATCATTACTACTGGAG CTGGATCCGGCAGCCCCCAGGGAAGGGACTGGAG TGGATTGGGGCGATCTATTACAGTGGGAGCACCCG GTACAACCCCTCCCTCAAGAGTCGAGTCACCATAT CAGTAGACACGTCCAAGAACCAGTTCTCCCTGAA GCTGAGTTCTGTGACCGCCGCAGACACGGCGGTG TACTACTGCGCCAGGGGTAAGAGTGCATTCGACCC ATGGGGACAGGGTACATTGGTCACCGTCTCCTCA (SEQ ID NO: 55) | QVQLQESGPGLVK PSETLSLTCTVSGG SINHYYWSWIRQP PGKGLEWIGAIYYS GSTRYNPSLKSRVT ISVDTSKNQFSLKL SSVTAADTAVYYC ARGKSAFDPWGQ GTLVTVSS (SEQ ID NO: 45) | GACATCCAGATGACCCAGTCTCC ATCTTCCGTGTCTGCATCTGTAG GAGACAGAGTCACCATCACTTGT CGGGCGAGTCAGGGTATTAGCA GGTGGTTAGCCTGGTATCAGCAG AAACCAGGGAAAGCCCCTAAGC TCCTGATCTATGCTGCATCCAGTT TGCAAAGTGGGGTCCCATCAAG GTTCAGCGGCAGTGGATCTGGG ACAGATTTCACTCTCACCATCAG CAGCCTGCAGCCTGAAGATTTTG CAACTTATTACTGTCAGCAGGCA GACCTCCACCCTCCTCTCACTTT TGGCGGAGGGACCAAGGTTGAG ATCAAG (SEQ ID NO: 73) | DIQMTQSPSS VSASVGDRV TITCRASQGI SRWLAWYQ QKPGKAPKL LIYAASSLQS GVPSRFSGSG SGTDFTLTISS LQPEDFATYY CQQADLHPP LTFGGGTKV EIK (SEQ ID NO: 65) |

TABLE B-continued

Sequences of Heavy Chain Variable Regions and Light Chain Variable Regions of Exemplary Antibodies of the Present Invention

| ADI Name | VH DNA | VH Protein | VL DNA | VL Protein |
|---|---|---|---|---|
| ADI-29338 | CAGGTGCAGCTGCAGGAGTCGGGCCCAGGACTGG TGAAGCCTTCGGAGACCCTGTCCTCACCTGCACT GTCTCTGGTGGCTCCATCAGTAGTTACTACTGGAG CTGGATCCGGCAGCCCCCAGGGAAGGGACTGGAG TGGATTGGGACGATCTATTACAGTGGGAGCACCCG GTACAACCCCTCCCTCAAGAGTCGAGTCACCATAT CAGTAGACACGTCCAAGAACCAGTTCTCCCTGAA GCTGAGTTCTGTGACCGCCGCAGACACGGCGGTG TACTACTGCGCCAGGGGTAAGAGTGCATTCGACCC ATGGGGACAGGGTACATTGGTCACCGTCTCCTCA (SEQ ID NO: 56) | QVQLQESGPGLVK PSETLSLTCTVSGG SISSYYWSWIRQPP GKGLEWIGTIYYS GSTRYNPSLKSRVT ISVDTSKNQFSLKL SSVTAADTAVYYC ARGKSAFDPWGQ GTLVTVSS (SEQ ID NO: 46) | GACATCCAGATGACCCAGTCTCC ATCTTCCGTGTCTGCATCTGTAG GAGACAGAGTCACCATCACTTGT CGGGCGAGTCAGGGTATTAGCA GGTGGTTAGCCTGGTATCAGCAG AAACCAGGGAAAGCCCCTAAGC TCCTGATCTATGCTGCATCCAGTT TGCAAAGTGGGGTCCCATCAAG GTTCAGCGGCAGTGGATCTGGG ACAGATTTCACTCTCACCATCAG CAGCCTGCAGCCTGAAGATTTTG CAACTTATTACTGTCAGCAGGCA GACCTCCACCCTCCTCTCACTTT TGGCGGAGGGACCAAGGTTGAG ATCAAA (SEQ ID NO: 74) | |
| ADI-29339 | CAGGTGCAGCTGCAGGAGTCGGGCCCAGGACTGG TGAAGCCTTCGGAGACCCTGTCCTCACCTGCACT GTCTCTGGTGGCTCCATCAGTCATTACTACTGGAG CTGGATCCGGCAGCCCCCAGGGAAGGGACTGGAG TGGATTGGGGTGATCTATTATAGTGGGAGCACCAA CTACAACCCCTCCCTCAAGAGTCGAGTCACCATAT CAGTAGACACGTCCAAGAACCAGTTCTCCCTGAA GCTGAGTTCTGTGACCGCCGCAGACACGGCGGTG TACTACTGCGCCAGGGGTAAGAGTGCATTCGACCC ATGGGGACAGGGTACATTGGTCACCGTCTCCTCA (SEQ ID NO: 57) | QVQLQESGPGLVK PSETLSLTCTVSGG SISHYYWSWIRQPP GKGLEWIGVIYYS GSTNYNPSLKSRVT ISVDTSKNQFSLKL SSVTAADTAVYYC ARGKSAFDPWGQ GTLVTVSS (SEQ ID NO: 47) | | |
| ADI-29342 | CAGGTGCAGCTGCAGGAGTCGGGCCCAGGACTGG TGAAGCCTTCGGAGACCCTGTCCTCACCTGCACT GTCTCTGGTGGCTCCATCATGCATTACTACTGGAG CTGGATCCGGCAGCCCCCAGGGAAGGGACTGGAG TGGATTGGGTATATCTATTACAGTGGGAGCACCAA CTACAACCCCTCCCTCAAGAGTCGAGTCACCATAT CAGTAGACACGTCCAAGAACCAGTTCTCCCTGAA GCTGAGTTCTGTGACCGCCGCAGACACGGCTGCCC TACTACTGCGCCAGGGGTAAGACGGGATCTGCCG CATGGGGACAGGGTACATTGGTCACCGTCTCCTCA (SEQ ID NO: 58) | QVQLQESGPGLVK PSETLSLTCTVSGG SIMHYYWSWIRQP PGKGLEWIGYIYYS GSTNYNPSLKSRVT ISVDTSKNQFSLKL SSVTAADTAVYYC ARGKTGSAAWGQ GTLVTVSS (SEQ ID NO: 48) | | |
| ADI-29345 | CAGGTGCAGCTGCAGGAGTCGGGCCCAGGACTGG TGAAGCCTTCGGAGACCCTGTCCTCACCTGCACT GTCTCTGGTGGCTCCATCAGTCATTACTACTGGAG CTGGATCCGGCAGCCCCCAGGGAAGGGACTGGAG TGGATTGGGTATATCTATTACAGTGGGGTTACCACT TACAACCCCTCCCTCAAGAGTCGAGTCACCATATC AGTAGACACGTCCAAGAACCAGTTCTCCCTGAAG CTGAGTTCTGTGACCGCCGCAGACACGGCGGTGT ACTACTGCGCCAGGGGTAAGACGGGATCTACCGC ATGGGGACAGGGTACATTGGTCACCGTCTCCTCA (SEQ ID NO: 59) | QVQLQESGPGLVK PSETLSLTCTVSGG SISHYYWSWIRQPP GKGLEWIGYIYYS GVTTYNPSLKSRV TISVDTSKNQFSLK LSSVTAADTAVYY CARGKTGSTAWGQ GTLVTVSS (SEQ ID NO: 49) | GACATCCAGATGACCCAGTCTCC ATCTTCCGTGTCTGCATCTGTAG GAGACAGAGTCACCATCACTTGT CGGGCGAGTCAGGGTATTAGCA GGTGGTTAGCCTGGTATCAGCAG AAACCAGGGAAAGCCCCTAAGC TCCTGATCTATGCTGCATCCAGTT TGCAAAGTGGGGTCCCATCAAG GTTCAGCGGCAGTGGATCTGGG ACAGATTTCACTCTCACCATCAG CAGCCTGCAGCCTGAAGATTTTG CAACTTATTACTGTCAGCAGACA GTCTCCTTCCCTATCACTTTTGGC GGAGGGACCAAGGTTGAGATCA AA(SEQ ID NO: 75) | DIQMTQSPSS VSASVGDRV TITCRASQGI SRWLAWYQ QKPGKAPKL LIYAASSLQS GVPSRFSGSG SGTDFTLTISS LQPEDFATYY CQQTVSFPIT FGGGTKVEI K (SEQ ID NO: 66) |
| ADI-29347 | CAGGTGCAGCTGCAGGAGTCGGGCCCAGGACTGG TGAAGCCTTCGGAGACCCTGTCCTCACCTGCACT GTCTCTGGTGGCTCCATCGCTAATTACTACTGGAG CTGGATCCGGCAGCCCCCAGGGAAGGGACTGGAG TGGATTGGGTATACCTATTTTAGTGGGAGTACCAAC TACAACCCCTCCCTCAAGAGTCGAGTCACCATATC AGTAGACACGTCCAAGAACCAGTTCTCCCTGAAG CTGAGTTCTGTGACCGCCGCAGACACGGCGGTGT ACTACTGCGCCAGGGGTAAGACGGGATCTGCCGC ATGGGGACAGGGTACATTGGTCACCGTCTCCTCA (SEQ ID NO: 60 ) | QVQLQESGPGLVK PSETLSLTCTVSGG SIANYYWSWIRQP PGKGLEWIGYTYF SGSTNYNPSLKSRV TISVDTSKNQFSLK LSSVTAADTAVYY CARGKTGSAAWG QGTLVTVSS(SEQ ID NO: 50) | | |
| ADI-26655 | CAGGTGCAGCTGCAGGAGTCGGGCCCAGGACTGG TGAAGCCTTCGGAGACCCTGTCCTCACCTGCACT GTCTCTGGTGGCTCCATCAGTAGTTACTACTGGAG CTGGATCCGGCAGCCCCCAGGGAAGGGACTGGAG TGGATTGGGTATATCTATTACAGTGGGAGCACCAC GTACAACCCCTCCCTCAAGAGTCGAGTCACCATAT CAGTAGACACGTCCAAGAACCAGTTCTCCCTGAA GCTGAGTTCTGTGACCGCCGCAGACACGGCGGTG TACTACTGCGCCAGAAAGAAAAGATTCTTCGACCT ATGGGGCAGGGAACAACTGTCACCGTCTCCTCA (SEQ ID NO: 61) | QVQLQESGPGLVK PSETLSLTCTVSGG SISSYYWSWIRQPP GKGLEWIGYIYYS GSTTYNPSLKSRVT ISVDTSKNQFSLKL SSVTAADTAVYYC ARKKRFFDLWGQ TTVTVSS (SEQ ID NO: 51) | GACATCCAGATGACCCAGTCTCC TTCCACCCTGTCTGCATCTGTAG GAGACAGAGTCACCATCACTTG CCCGGGCCAGTCAGAGTATTAGTA GCTGGTTGGCCTGGTATCAGCAG AAACCAGGGAAAGCCCCTAAGC TCCTGATCTATAAAGCTCCAGT TTGGAAAGTGGGGTCCCATCAA GGTTCAGCGGCAGTGGATCTGG GACAGAATTCACTCTCACCATCA GCAGCCTGCAGCCTGATGATTTT GCAACTTATTACTGCCAGCAGGT CAAAGTTACTCCTCTCACTT TTGGCGGAGGGACCAAGGTTGA GATCAAA (SEQ ID NO: 76) | DIQMTQSPST LSASVGDRV TITCRASQSIS SWLAWYQQ KPGKAPKLLI YKASSLESG VPSRFSGSGS GTEFTLTISSL QPDDFATYY CQQVKSYSP LTFGGGTKV EIK (SEQ ID NO: 67) |
| ADI-29350 | CAGGTGCAGCTGCAGGAGTCGGGCCCAGGACTGG TGAAGCCTTCGGAGACCCTGTCCTCACCTGCACT GTCTCTGGTGGCTCCATCGAGCATTACTACTGGAG CTGGATCCGGCAGCCCCCAGGGAAGGGACTGGAG TGGATTGGGTATATCTATTACAGTGGGTTTACCGAG | QVQLQESGPGLVK PSETLSLTCTVSGG SIEHYYWSWIRQPP GKGLEWIGYIYYS GFTEYNPSLKSRVT | | |

TABLE B-continued

Sequences of Heavy Chain Variable Regions and Light Chain Variable Regions of
Exemplary Antibodies of the Present Invention

| ADI Name | VH DNA | VH Protein | VL DNA | VL Protein |
|---|---|---|---|---|
|  | TACAACCCCTCCCTCAAGAGTCGAGTCACCATATC AGTAGACACGTCCAAGAACCAGTTCTCCCTGAAG CTGAGTTCTGTGACCGCCGCAGACACGGCGGTGT ACTACTGCGCCAGAAAGAAAAGATTCTTCGACCTA TGGGGCCAGGGAACAACTGTCACCGTCTCCTCA (SEQ ID NO: 62) | ISVDTSKNQFSLKL SSVTAADTAVYYC ARKKRFFDLWGQG TTVTVSS (SEQ ID NO: 52) |  |  |
| ADI-26660 | CAGGTGCAGCTGCAGGAGTCGGGCCCAGGACTGG TGAAGCCTTCGGAGACCCTGTCCCTCACCTGCACT GTCTCTGGTGGCTCCATCAGTAGTTACTACTGGAG CTGGATCCGGCAGCCCCCAGGGAAGGGACTGGAG TGGATTGGGTCAATCTATTACAGTGGGAGCACCAA CTACAACCCCTCCCTCAAGAGTCGAGTCACCATAT CAGTAGACACGTCCAAGAACCAGTTCTCCCTGAA GCTGAGTTCTGTGACCGCCGCAGACACGGCGGTG TACTACTGCGCCAGAAAGCAAAAACACTTCGACA TATGGGGTCAGGGTACAATGGTCACCGTCTCCTCA (SEQ ID NO: 63) | QVQLQESGPGLVK PSETLSLTCTVSGG SISSYYWSWIRQPP GKGLEWIGSIYYSG STNYNPSLKSRVTI SVDTSKNQFSLKLS SVTAADTAVYYCA RKQKHFDIWGQGT MVTVSS (SEQ ID NO: 53) | GACATCCAGATGACCCAGTCTCC ATCTTCCGTGTCTGCATCTGTAG GAGACAGAGTCACCATCACTTGT CGGGCGAGTCAGGGTATTAGCA GCTGGTTAGCCTGGTATCAGCAG AAACCAGGGAAAGCCCCTAAGC TCCTGATCTATGCTGCATCCAGTT TGCAAAGTGGGGTCCCATCAAG GTTCAGCGGCAGTGGATCTGGG ACAGATTTCACTCTCACCATCAG CAGCCTGCAGCCTGAAGATTTTG CAACTTATTACTGTCAGCAGGTA AATCACCACCCTTGGACTTTTGG CGGAGGGACCAAGGTTGAGATC AAA (SEQ ID NO: 77) | DIQMTQSPSS VSASVGDRV TITCRASQGI SSWLAWYQ QKPGKAPKL LIYAASSLQS GVPSRFSGSG SGTDFTLTISS LQPEDFATYY CQQVNHHP WTFGGGTKV EIK (SEQ ID NO: 68) |
| ADI-29362 | CAGGTGCAGCTGCAGGAGTCGGGCCCAGGACTGG TGAAGCCTTCGGAGACCCTGTCCCTCACCTGCACT GTCTCTGGTGGCTCCATCGAGCATTACTACTGGAG CTGGATCCGGCAGCCCCCAGGGAAGGGACTGGAG TGGATTGGGCGATCTATTACTCGGGGAGCACCAA CTACAACCCCTCCCTCAAGAGTCGAGTCACCATAT CAGTAGACACGTCCAAGAACCAGTTCTCCCTGAA GCTGAGTTCTGTGACCGCCGCAGACACGGCGGTG TACTACTGCGCCAGAAAGCAAAAACACTTCGACA TATGGGGTCAGGGTACAATGGTCACCGTCTCCTCA (SEQ ID NO: 64) | QVQLQESGPGLVK PSETLSLTCTVSGG SIEHYYWSWIRQPP GKGLEWIGAIYYS GSTNYNPSLKSRVT ISVDTSKNQFSLKL SSVTAADTAVYYC ARKQKHFDIWGQG TMVTVSS (SEQ ID NO: 54) |  |  |

TABLE C

Numbers Corresponding to Part of Sequences in Sequence Listing of the Present Invention

| ADI Name | Heavy Chain / Heavy Chain Variable Region(VH) | | | | | Light Chain / Light Chain Variable Region(VL) | | | | | Heavy Chain (HC) | Light Chain (LC) |
|---|---|---|---|---|---|---|---|---|---|---|---|---|
|  | VH CDR1 (SEQ ID NO) | VH CDR2 (SEQ ID NO) | VH CDR3 (SEQ ID NO) | VH DNA (SEQ ID NO) | VH Pro. (SEQ ID NO) | VL CDR1 (SEQ ID NO) | VL CDR2 (SEQ ID NO) | VL CDR3 (SEQ ID NO) | VL DNA (SEQ ID NO) | VL Pro. (SEQ ID NO) | | |
| ADI-29337 | 15 | 21 | 31 | 55 | 45 | 36 | 39 | 41 | 73 | 65 | 1 | 2 |
| ADI-29338 | 16 | 22 |  | 56 | 46 |  |  |  | 74 |  | 3 |  |
| ADI-29339 | 17 | 23 |  | 57 | 47 |  |  |  |  |  | 4 |  |
| ADI-29342 | 18 | 24 | 32 | 58 | 48 |  |  | 42 | 75 | 66 | 5 | 6 |
| ADI-29345 | 17 | 25 | 33 | 59 | 49 |  |  |  |  |  | 7 |  |
| ADI-29347 | 19 | 26 | 32 | 60 | 50 |  |  |  |  |  | 8 |  |
| ADI-26655 | 16 | 27 | 34 | 61 | 51 | 37 | 40 | 43 | 76 | 67 | 9 | 10 |
| ADI-29350 | 20 | 28 |  | 62 | 52 |  |  |  |  |  | 11 |  |
| ADI-26660 | 16 | 29 | 35 | 63 | 53 | 38 | 39 | 44 | 77 | 68 | 12 | 13 |
| ADI-29362 | 20 | 30 |  | 64 | 54 |  |  |  |  |  | 14 |  |

Full-length Amino Acid Sequences of Heavy Chains and
Light Chains of Antibodies of the Present Invention ADI29337
HC amino acid sequence
(SEQ ID NO: 1)
QVQLQESGPGLVKPSETLSLTCTVSGGSINHYYWSWIRQPPGKGLEWIGAIYYSGSTRYNPS

LKSRVTISVDTSKNQFSLKLSSVTAADTAVYYCARGKSAFDPWGQGTLVTVSSASTKGPSVF

PLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGGPSVFLFPPKPKDT

```
-continued
LMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEAL

HNHYTQKSLSLSPG

LC amino acid sequence
                                                      (SEQ ID NO: 2)
DIQMTQSPSSVSASVGDRVTITCRASQGISRWLAWYQQKPGKAPKLLIYAASSLQSGVPSRF

SGSGSGTDFTLTISSLQPEDFATYYCQQADLHPPLTFGGGTKVEIKRTVAAPSVFIFPPSDEQL

KSGTASVVCLLNNFYPREAKVQWKVDNALQSGNSQESVTEQDSKDSTYSLSSTLTLSKAD

YEKHKVYACEVTHQGLSSPVTKSFNRGEC

ADI29338
HC amino acid sequence
                                                      (SEQ ID NO: 3)
QVQLQESGPGLVKPSETLSLTCTVSGGSISSYYWSWIRQPPGKGLEWIGTIYYSGSTRYNPSL

KSRVTISVDTSKNQFSLKLSSVTAADTAVYYCARGKSAFDPWGQGTLVTVSSASTKGPSVFP

LAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALH

NHYTQKSLSLSPG

ADI29339
HC amino acid sequence
                                                      (SEQ ID NO: 4)
QVQLQESGPGLVKPSETLSLTCTVSGGSISHYYWSWIRQPPGKGLEWIGVIYYSGSTNYNPS

LKSRVTISVDTSKNQFSLKLSSVTAADTAVYYCARGKSAFDPWGQGTLVTVSSASTKGPSVF

PLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEAL

HNHYTQKSLSLSPG

ADI29342
HC amino acid sequence
                                                      (SEQ ID NO: 5)
QVQLQESGPGLVKPSETLSLTCTVSGGSIMHYYWSWIRQPPGKGLEWIGYIYYSGSTNYNPS

LKSRVTISVDTSKNQFSLKLSSVTAADTAVYYCARGKTGSAAWGQGTLVTVSSASTKGPSV

FPLAPSSKSTSGGTAALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEA

LHNHYTQKSLSLSPG

LC amino acid sequence
                                                      (SEQ ID NO: 6)
DIQMTQSPSSVSASVGDRVTITCRASQGISRWLAWYQQKPGKAPKLLIYAASSLQSGVPSRF

SGSGSGTDFTLTISSLQPEDFATYYCQQTVSFPITFGGGTKVEIKRTVAAPSVFIFPPSDEQLKS
```

-continued

GTASVVCLLNNFYPREAKVQWKVDNALQSGNSQESVTEQDSKDSTYSLSSTLTLSKADYE

KHKVYACEVTHQGLSSPVTKSFNRGEC

ADI 29345
HC amino acid sequence
(SEQ ID NO: 7)
QVQLQESGPGLVKPSETLSLTCTVSGGSISHYYWSWIRQPPGKGLEWIGYIYYSGVTTYNPS

LKSRVTISVDTSKNQFSLKLSSVTAADTAVYYCARGKTGSTAWGQGTLVTVSSASTKGPSVF

PLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEAL

HNHYTQKSLSLSPG

ADI 29347
HC amino acid sequence
(SEQ ID NO: 8)
QVQLQESGPGLVKPSETLSLTCTVSGGSIANYYWSWIRQPPGKGLEWIGYTYFSGSTNYNPS

LKSRVTISVDTSKNQFSLKLSSVTAADTAVYYCARGKTGSAAWGQGTLVTVSSASTKGPSV

FPLAPSSKSTSGGTAALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEA

LHNHYTQKSLSLSPG

ADI 26655
HC amino acid sequence
(SEQ ID NO: 9)
QVQLQESGPGLVKPSETLSLTCTVSGGSISSYYWSWIRQPPGKGLEWIGYIYYSGSTTYNPSL

KSRVTISVDTSKNQFSLKLSSVTAADTAVYYCARKKRFFDLWGQGTTVTVSSASTKGPSVFP

LAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVFSCSVMHEALH

NHYTQKSLSLSPG

LC amino acid sequence
(SEQ ID NO: 10)
DIQMTQSPSTLSASVGDRVTITCRASQSISSWLAWYQQKPGKAPKLLIYKASSLESGVPSRFS

GSGSGTEFTLTISSLQPDDFATYYCQQVKSYSPLTFGGGTKVEIKRTVAAPSVFIFPPSDEQLK

SGTASVVCLLNNFYPREAKVQWKVDNALQSGNSQESVTEQDSKDSTYSLSSTLTLSKADY

EKHKVYACEVTHQGLSSPVTKSFNRGEC

ADI 29350
HC amino acid sequence
(SEQ ID NO: 11)
QVQLQESGPGLVKPSETLSLTCTVSGGSIEHYYWSWIRQPPGKGLEWIGYIYYSGFTEYNPS

LKSRVTISVDTSKNQFSLKLSSVTAADTAVYYCARKKRFFDLWGQGTTVTVSSASTKGPSVF

PLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGGPSVFLFPPKPKDT

-continued

LMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEAL

HNHYTQKSLSLSPG

ADI 26660
HC amino acid sequence
(SEQ ID NO: 12)
QVQLQESGPGLVKPSETLSLTCTVSGGSISSYYWSWIRQPPGKGLEWIGSIYYSGSTNYNPSL

KSRVTISVDTSKNQFSLKLSSVTAADTAVYYCARKQKHFDIWGQGTMVTVSSASTKGPSVF

PLAPSSKSTSGGTAALGCLVKDYFPEPVTVSWNSGALTSGVHTFPAVLQSSGLYSLSSVVTV

PSSSLGTQTYICNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEAL

HNHYTQKSLSLSPG

LC amino acid sequence
(SEQ ID NO: 13)
DIQMTQSPSSVSASVGDRVTITCRASQGISSWLAWYQQKPGKAPKLLIYAASSLQSGVPSRF

SGSGSGTDFTLTISSLQPEDFATYYCQQVNHHPWTFGGGTKVEIKRTVAAPSVFIFPPSDEQL

KSGTASVVCLLNNFYPREAKVQWKVDNALQSGNSQESVTEQDSKDSTYSLSSTLTLSKAD

YEKHKVYACEVTHQGLSSPVTKSFNRGEC

ADI 29362
HC amino acid sequence
(SEQ ID NO: 14)
QVQLQESGPGLVKPSETLSLTCTVSGGSIEHYYWSWIRQPPGKGLEWIGAIYYSGSTNYNPS

LKSRVTISVDTSKNQFSLKLSSVTAADTAVYYCARKQKHFDIWGQGTMVTVSSASTKGPSV

FPLAPSSKSTSGGTAALGCLVKDYFPEPVTVSWNSGALTSGVHTFPAVLQSSGLYSLSSVVT

VPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEA

LHNHYTQKSLSLSPG

Amino acid sequence of CD47 protein
(SEQ ID NO: 78)
MWPLVAALLLGSACCGSAQLLFNKTKSVEFTFCNDTVVIPCFVTNMEAQNTTEVYVKWKF

KGRDIYTFDGALNKSTVPTDFSSAKIEVSQLLKGDASLKMDKSDAVSHTGNYTCEVTELTR

EGETIIELKYRVVSWFSPNENILIVIFPIFAILLFWGQFGIKTLKYRSGGMDEKTIALLVAGLVI

TVIVIVGAILFVPGEYSLKNATGLGLIVTSTGILILLHYYVFSTAIGLTSFVIAIL-
VIQVIAYILAV

VGLSLCIAACIPMHGPLLISGLSILALAQLLGLVYMKFVE

The sequences of negative controls appearing in the drawings are as follows:

IgG1 HC:
(SEQ ID NO: 79)
MGWSLILLFLVAVATRVLSEVRLLESGGGLVQPGGSLRLSCAASG

FTFSNYAMGWVRQAPGKGLEWVSAISGSGGSTYYADSVKGRFTTS

-continued

RDDSKNALYLQMNSLRAEDTAVYYCARGGPGWYAADVWGQGTTVT

VSSASTKGPSVFPLAPSSKSTSGGTAALGCLVKDYFPEPVTVSWN

SGALTSGVHTFPAVLQSSGLYSLSSVVTVPSSSLGTQTYICNVNH

KPSNTKVDKKVEPKSCDKTHTCPPCPAPELLGGPSVFLFPPKPKD

-continued
TLMISRTPEVTCVVVDVSHEDPEVKFNWYVDGVEVHNAKTKPREE

QYNSTYRVVSVLTVLHQDWLNGKEYKCKVSNKALPAPIEKTISKA

KGQPREPQVYTLPPSRDELTKNQVSLTCLVKGFYPSDIAVEWESN

GQPENNYKTTPPVLDSDGSFFLYSKLTVDKSRWQQGNVFSCSVMH

EALHNHYTQKSLSLSPG

IgG1 LC
(SEQ ID NO: 80)
MDFQVQIISFLLISASVIMSRGDIQMTQSPSSLSASVGDRVTITCR

ASQSISSYLNWYQQKPGKAPKLLIYAASSLQSGVPSRFSGSGSGTD

FTLTISSLQPEDFATYYCQQADLPAFAFGGGTKVEIKRTVAAPSVF

IFPPSDEQLKSGTASVVCLLNNFYPREAKVQWKVDNALQSGNSQES

VTEQDSKDSTYSLSSTLTLSKADYEKHKVYACEVTHQGLSSPVTKS

FNRGEC

EXAMPLES

Example 1. Production and Purification of Anti-CD47 Antibodies and Control Antibodies The amino acid sequences of the CDR regions, light chain variable regions, heavy chain variable regions, light chains and heavy chains of the 10 exemplary antibodies (ADI-29337, ADI-29338, ADI-29339, ADI-29342, ADI-29345, ADI-29347, ADI-26655, ADI-29350, ADI-26660, ADI-29362) disclosed herein, as well as the corresponding nucleotide sequences, are listed in the specification of the present invention and the "sequence listing". In addition, the sequence numbers of the light chains, heavy chains, light chain variable regions and heavy chain variable regions of the aforementioned exemplary antibodies of the present invention are shown in Table 5. The antibody of the present invention was expressed and purified in yeast cells.

Expression and Purification in Yeast Cells

Yeast-based antibody presentation libraries (Adimab) were amplified according to prior art (described in WO 2009036379; WO 2010105256; WO 2012009568), with a diversity of $1 \times 10^9$ in each library. Briefly, the first two rounds of screening employed magnetic-activated cell sorting using the MACS system available from Miltenyi. First, yeast cells (about $1 \times 10^{10}$ cells/library) from the libraries were respectively incubated in FACS buffer (phosphate buffer, containing 0.1% bovine serum albumin) at room temperature for 15 min, and the buffer contained 100 nM biotin-labeled CD47 antigens (AcroBiosystems, catalog No.: CD7-H5227-1 mg). The cells were washed once with 50 mL of pre-cooled FACS buffer, and resuspended with 40 mL of the same buffer, followed by addition of 500 μL of streptomycin microbeads (Miltenyi LS) and incubation at 4° C. for 15 min. The mixture was centrifuged at 1000 rpm for 5 min. After discarding the supernatant, the cells were resuspended with 5 mL of FACS buffer. The resulting cell suspension was loaded on a Miltenyi LS column. After loading, the column was washed three times, with 3 mL of FACS buffer each time. The Miltenyi LS column was removed from the magnetic field and eluted with 5 mL of growth medium. The eluted yeast cells were collected and incubated overnight at 37° C.

The next round of sorting was performed using a flow cytometer, wherein approximately $1 \times 10^8$ yeast cells screened by an MACS system were washed three times with FACS buffer and cultivated in CD47 antigens labeled by a low concentration of biotin (100-1 nM) at room temperature. The supernatant was discarded. The cells were washed twice with FACS buffer, and mixed with LC-FITC (FITC-labeled goat anti-human immunoglobulin F(ab') kappa chain antibody, Southern Biotech) (1:100 dilution) and SA-633 (streptavidin-633, Molecular Probes) (1:500 dilution) or SA-PE (streptavidin-phycoerythrin, Sigma) (1:50 dilution) reagents, and the mixture was cultivated at 4° C. for 15 min. The cells were eluted twice with pre-cooled FACS buffer, resuspended in 0.4 mL of buffer and transferred into a separator tube with a filter. The cells were sorted using FACS ARIA (BD Biosciences).

The yeast cells expressing the anti-CD47 antibody obtained by screening were induced by shaking at 30° C. for 48 h to express the anti-CD47 antibody. After the induction, the yeast cells were removed by centrifugation at 1300 rpm for 10 min, and the supernatant was collected. The anti-CD47 antibodies in the supernatant were purified by Protein A and eluted with acetic acid buffer at pH2.0 prior to harvest. The purity of the antibodies was more than 95%. The antibodies were digested by papin and purified by KappaSelect (GE Healthcare) to produce the corresponding Fab fragments.

TABLE 1

Amino Acid Sequence Numbers of Light Chains, Heavy Chains, Light Chain Variable Regions and Heavy Chain Variable Regions of Exemplary Antibodies of the Present Invention

| Antibody | VH | VL | HC | LC |
|---|---|---|---|---|
| ADI-29337 | 45 | 65 | 1 | 2 |
| ADI-29338 | 46 | 65 | 3 | 2 |
| ADI-29339 | 47 | 65 | 4 | 2 |
| ADI-29342 | 48 | 66 | 5 | 6 |
| ADI-29345 | 49 | 66 | 7 | 6 |
| ADI-29347 | 50 | 66 | 8 | 6 |
| ADI-26655 | 51 | 67 | 9 | 10 |
| ADI-29350 | 52 | 67 | 11 | 10 |
| ADI-26660 | 53 | 68 | 12 | 13 |
| ADI-29362 | 54 | 68 | 14 | 13 |

The following control antibodies are used in the examples of expression and purification in HEK293 cells:

| Control Antibody |
|---|
| Hu5F9 |
| AB6.12 |

Hu5F9 is a human CD47 antibody transiently expressed in HEK293 cells, and its sequence is the same as that of antibody "5F9" in U.S. Patent No. US2015/0183874 A1. AB6.12 is a humanized CD47 antibody transiently expressed in HEK293 cells, and its sequence is the same as that of the antibody "AB6.12" in U.S. Pat. No. 9,045,541.

For a transient expression of an antibody in HEK293 cells, the vector pTT5 was used. The heavy and light chains of the antibody were first cloned into separate pTT5 vectors. The pTT5 vectors carrying the heavy chains and light chains of the antibody molecule were transferred into the HEK293 cells using a chemical transfection method. The cultivated HEK293 cells were transiently transfected using a chemical transfection reagent PEI (purchased from Polysciences) according to a scheme provided by the manufacturer. Plasmid DNAs and transfection reagent were prepared in a laminar flow hood, and then F17 medium (Gibco) (the volume was ⅕ of transfection volume) was aliquoted into two 50-mL centrifuge tubes. The filtered plasmids (130 µg/100 mL) were added to one tube, and the filtered PEI (1 g/L, Polysciences) (mass ratio (plasmid:PEI)=1:3) was added to another. The two mixtures were each mixed well for 5 min, and then the two were mixed well and gently together for 20 times, followed by letting stand for 15-30 min (no more than 30 min). The DNA/PEI mixture was gently poured into the HEK293 cells and mixed well. The cells were cultivated at 37° C., 8% $CO_2$ for 7 days, with fresh medium fed every 48 h. Seven days later, or when the cells were continuously cultivated to cell viability was <60%, the mixture was centrifuged at 13000 rpm for 20 min. The supernatant was taken and purified with Protein A to achieve an antibody purity of greater than 95%.

Example 2: Affinity Assay of Anti-CD47 Antibodies of the Present Invention

The equilibrium dissociation constant ($K_D$) of the aforementioned 10 exemplary antibodies of the present invention (the Fab fragments were used in a monovalent experiment in order to eliminate the possible influence of the Fc fragments) binding to human CD47 (hCD47) was measured by biological optical interferometry (ForteBio).

An ForteBio affinity assay was performed according to the prior art (Estep, P, et al., High throughput solution Based measurement of antibody-antigen affinity and epitope binning MAbs, 2013.5(2): p. 270-8). Briefly, the sensor was equilibrated offline in an assay buffer for 30 min, and on-line detection was then conducted for 60 s to establish a baseline. The purified antibodies obtained as described above were loaded on-line onto an AHQ sensor (ForteBio) for the ForteBio affinity assay. The sensor with the loaded antibodies was then exposed to 100 nM CD47 antigens for 5 min before transferring the sensor to the assay buffer for dissociation for 5 min for dissociation rate measurement. Kinetic analysis was performed using a 1:1 binding model.

In the assay described above, the affinities of ADI-29337, ADI-29338, ADI-29339, ADI-29342, ADI-29345, ADI-29347, ADI-26655, ADI-29350, ADI-26660 and ADI-29362 are shown in Table 6.

TABLE 2

Binding of the Antibodies of the Present Invention as Determined by Biological Optical Interferometry

| Antibody | ForteBio image: human CD47-Fc on AHQ tip/antibodies of Fab form in solution (100 nM) [monovalent] | ForteBio image: antibodies on AHQ tip/human CD47-Fc in solution (100 nM) [bivalent] | ForteBio image: antibodies on AHQ tip/cynomolgus monkey CD47-Fc in solution (100 nM) [bivalent] | ForteBio image: antibodies on AHQ tip/mouse CD47-Fc in solution (100 nM) [bivalent] |
|---|---|---|---|---|
| ADI-29337 | 2.204E−09 | 4.04E−10 | 5.54E−10 | 1.866E−08 |
| ADI-29338 | 6.07E−09 | 6.21E−10 | 5.87E−10 | N.B. |
| ADI-29339 | 7.24E−09 | 6.28E−10 | 6.38E−10 | 1.55E−08 |
| ADI-29342 | 1.17E−08 | 4.86E−10 | 5.14E−10 | N.B. |
| ADI-29345 | 2.89E−09 | 4.03E−10 | 5.47E−10 | N.B. |
| ADI-29347 | 1.13E−08 | 7.10E−10 | 5.62E−10 | N.B. |
| ADI-26655 | 4.63E−08 | 8.49E−10 | 9.63E−10 | N.B. |
| ADI-29350 | 5.04E−09 | 4.51E−10 | 5.69E−10 | N.B. |
| ADI-26660 | 1.30E−07 | 1.35E−09 | 1.52E−09 | N.B. |
| ADI-29362 | 8.97E−09 | 7.00E−10 | 6.55E−10 | N.B. |
| Hu5F9 | 1.66E−08 | 4.20E−10 | 6.41E−10 | 1.266E−08 |

Note: N.B. represents non-bound.

It can be seen that all of the aforementioned 10 exemplary antibodies of the present invention exhibit extremely high affinities, wherein the monovalent affinities of ADI-29337, ADI-29338, ADI-29339, ADI-29345 and ADI-29350 are respectively 2.204E-09, 6.07E-09, 7.24E-09, 2.89E-09 and 5.04E-09, which are significantly higher than that of the excellent CD47 antibody Hu5F9 (1.66E-08) known and recognized in the art, and the affinities of the other several antibodies of the present invention are comparable to that of Hu5F9.

Example 3. Binding of Anti-CD47 Antibodies of the Present Invention to Human CD47

The binding of the 10 exemplary antibodies of the present invention described above to human CD47 was measured in a flow cytometry-based assay.

The pCHO1.0 vector (Invitrogen) carrying human CD47 cDNA (Sino Biological) cloned to a multiple cloning site (MCS) was transfected to produce CHO cells (CHO-hCD47 cells) overexpressing human CD47. The CHO-hCD47 cells ($0.2 \times 10^6$ cells) and test antibodies with different concentrations (the aforementioned 10 exemplary antibodies of the present invention, Hu5F9 and AB6.12 were serially three-fold diluted from a concentration of 300 nM to the 11th concentration) were co-incubated in PBS containing 0.1% of bovine serum albumin (BSA) on ice for 30 min. The cells were then washed at least twice, and were incubated with a secondary antibody (a PE-labeled goat anti-human IgG antibody (SouthernBiotech) with a final concentration of 5 µg/mL) in PBS containing 0.1% of BSA on ice (in the dark) for 30 min. The cells were washed at least twice and analyzed by flow cytometry. The flow cytometry assay was performed on the Accuri C6 system (BD Biosciences), and a concentration-dependent curve was fitted according to the MFI.

Figure 2:
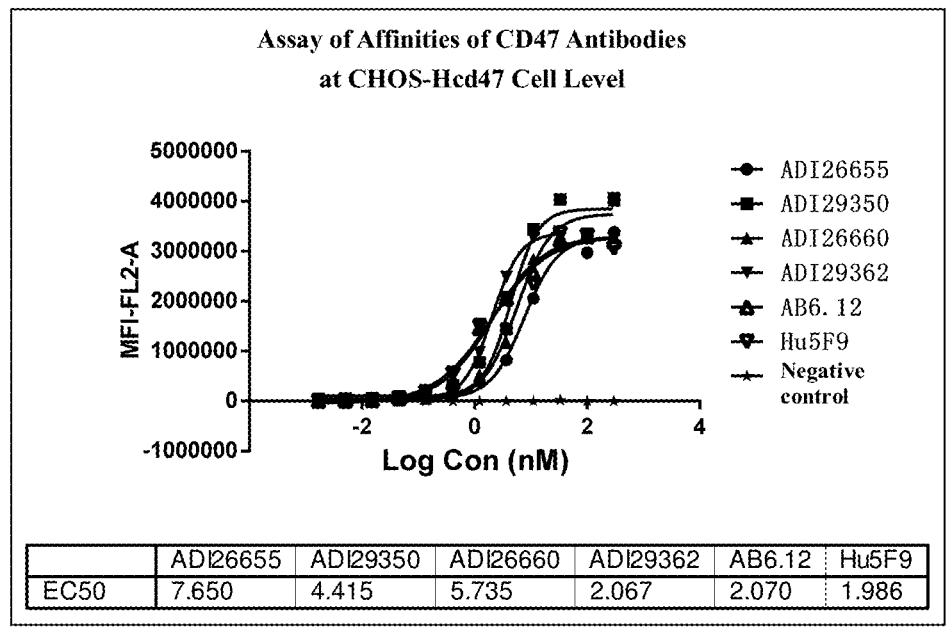
FIG. 2 shows an assay of affinities of anti-CD47 antibodies at cell levels.

In the assay described above, ADI-29338, ADI-29339, ADI-29345 and ADI-29347 bind to hCD47 overexpressed on CHO cells, with $EC_{50}$ being respectively 1.566 nM, 1.871 nM, 1.496 nM and 1.815 nM, and all of their affinities with hCD47 at a cell level are higher than those of the control antibodies Hu5F9 ($EC_{50}$: 1.986 nM) and AB6.12 ($EC_{50}$: 2.07 nM). ADI-29337, ADI-29342, ADI-26655, ADI-29350, ADI-26660 and ADI-29362 bind to hCD47 overexpressed on CHO cells, with $EC_{50}$ being respectively 2.945 nM, 2.742 nM, 7.65 nM, 4.415 nM, 5.735 nM and 2.067 nM, and their binding abilities are substantially comparable with the binding abilities of control antibodies Hu5F9 and AB6.12 (EC50 values: 1.986 nM and 2.07 nM) to CD47 overexpressed on CHO cells (see FIG. 1 and FIG. 2).

Example 4. Blockade of Interaction Between Human CD47 Ligand SIRPα and CD47 by Anti-CD47 Antibodies of the Present Invention The abilities of the aforementioned 10 exemplary antibodies of the present invention in blocking the binding of human CD47 to SIRPα were measured by the flow cytometry.

$0.2 \times 10^6$ CHO cells expressing human CD47 prepared in Example 3 described above were co-incubated along with the test antibodies (the aforementioned 10 exemplary antibodies of the present invention and Hu5F9 were serially three-fold diluted from a concentration of 300 nM to the 11th concentration) and 200 nM mouse Fc-labeled SIRPα proteins (AcroBiosystems) in PBS containing 0.1% of BSA on ice for 30 min. The cells were then washed three times, and were incubated with a secondary antibody (Biolegend) goat anti-mouse IgG-APC (allophycocyanin) in PBS containing 0.1% of BSA on ice (in the dark) for 30 min. The cells were washed three times. A flow cytometry assay was performed on the Accuri C6 system (BD Biosciences), and the MFI was calculated using C6 software.

The abilities of ADI-29337, ADI-29338, ADI-29339, ADI-29342, ADI-29345 and ADI-29347 in blocking the binding of human SIRPα-APC to CD47 are all higher than that of the control antibody Hu5F9. The abilities of ADI-26655, ADI-29350, ADI-26660 and ADI-29362 in blocking the binding of human SIRPα-APC to CD47 are comparable to that of the control antibody Hu5F9.

Figure 3:
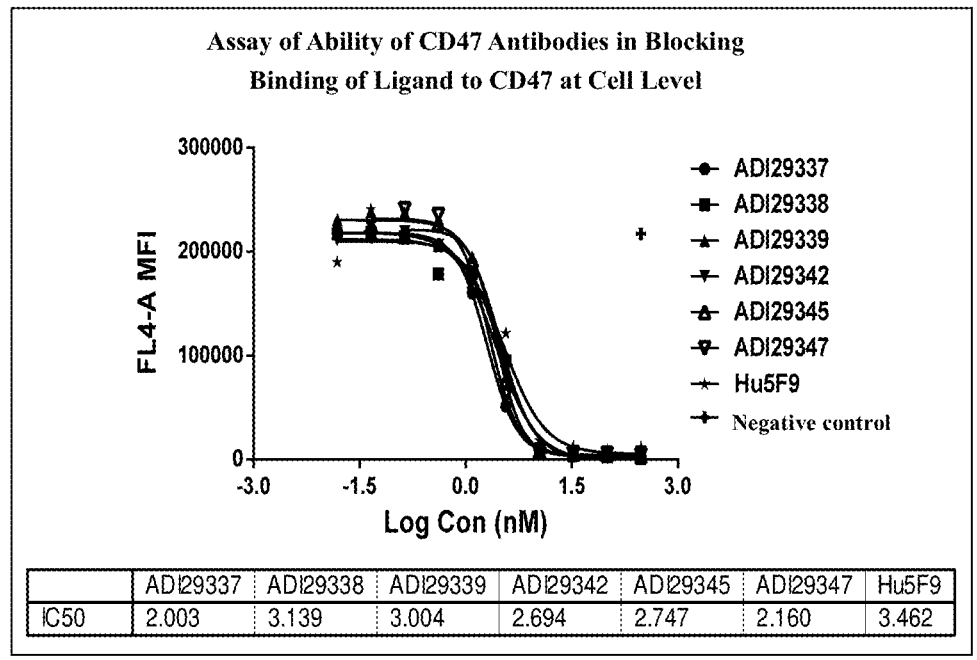
FIG. 3 shows an assay of blocking effect of the antibodies of the present invention on the binding of SIRPα to CD47 expressed on CHO cells by flow cytometry.

Specifically, the $IC_{50}$ of ADI-29337, ADI-29338, ADI-29339, ADI-29342, ADI-29345 and ADI-29347 in blocking the binding of human SIRPα-APC to CD47 are respectively 2.003 nM, 3.139 nM, 3.004 nM, 2.694 nM, 2.747 nM and 2.16 nM. The $IC_{50}$ of the control antibody Hu5F9 in blocking the binding of human SIRPα-APC to CD47 is 3.462 nM. (See FIG. 3)

Figure 4:
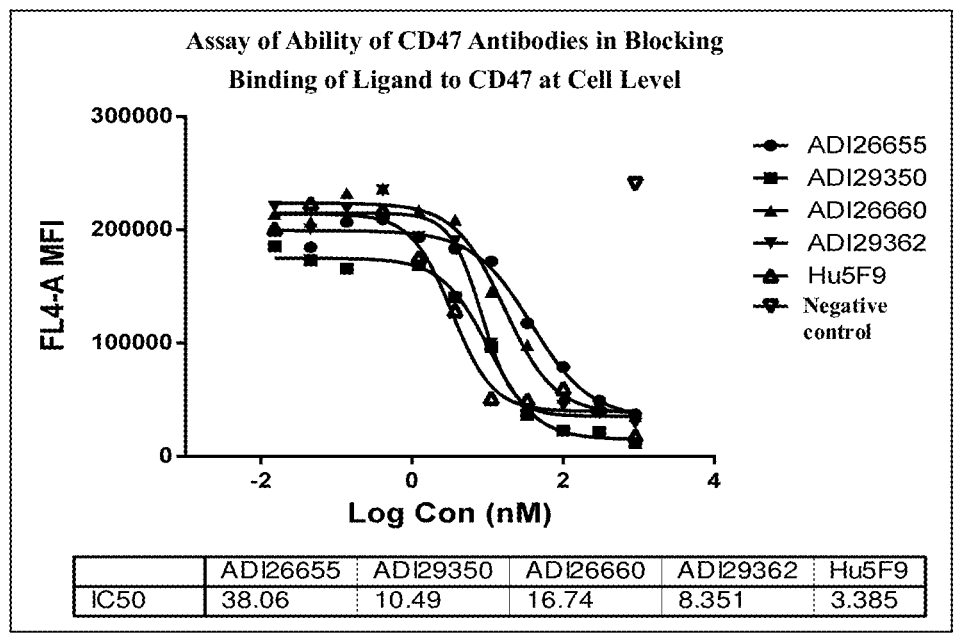
FIG. 4 shows an assay of blocking effect of the antibodies of the present invention on the binding of SIRPα to CD47 expressed on CHO cells by flow cytometry.

The $IC_{50}$ of ADI-26655, ADI-29350, ADI-26660 and ADI-29362 in blocking the binding of human SIRPα-APC to CD47 are respectively 38.06 nM, 10.49 nM, 16.74 nM and 8.351 nM. The $IC_{50}$ of the control antibody Hu5F9 in blocking the binding of human SIRPα-APC to CD47 is 3.385 nM. (See FIG. 4).

Example 5: Assay of Ability of Anti-CD47 Antibodies of the Present Invention in Promoting the Phagocytosis of Tumor Cells by Macrophages The abilities of the antibodies (ADI-29337, ADI-29338, ADI-29339, ADI-29342, ADI-29345, ADI-29347, ADI-26655, ADI-29350, ADI-26660 and ADI-29362) in promoting the phagocytosis of tumor cells by macrophages were measured by a flow cytometry-based assay.

Density gradient centrifugation was carried out for fresh blood taken from a donor to obtain peripheral blood mononuclear cells (PBMCs). The isolated PBMCs were purified according to the instructions of the kit (EasySep™ Human CD14 Positive Selection Kit, Steam cell) to give CD14-positive monocytes, and 10 ng/mL of granulocyte-macrophage colony-stimulating factors (GM-CSF, R&D Systems) were added, and the cells were cultivated adherently for 7 days; wherein, on day 5, 20 ng/mL of interferon-γ (IFN-γ, AcroBiosystem) was added for 1 h of stimulation, 100 ng/mL of lipopolysaccharide (LPS, Sigma) was then added for 48 h of stimulation, and thereby the monocytes were induced into macrophages. Target tumor cells CCRF-CEM (purchased from ATCC) were fluorescently labeled according to the instructions of a CellTrace™ CFSE kit. The labeled tumor cells were co-incubated at a ratio of 4:1 along with the aforementioned macrophages which had completed differentiation, and meanwhile. test antibodies with different concentrations were added. The cells were incubated at 37° C. for 3 h. The cells were then washed at least twice, added with CD14 antibody (purchased from BD) labeled by allophycocyanin (APC), and incubated in PBS containing 0.1% BSA on the ice (in the dark) for 30 min. The cells were washed at least twice and analyzed by flow cytometry. The phagocytized cell colony was a cell colony which was CD14-positive and fluorescent dye CFSE (carboxyfluorescein diacetate, succinimidyl ester) positive among living cells.

Figure 5:
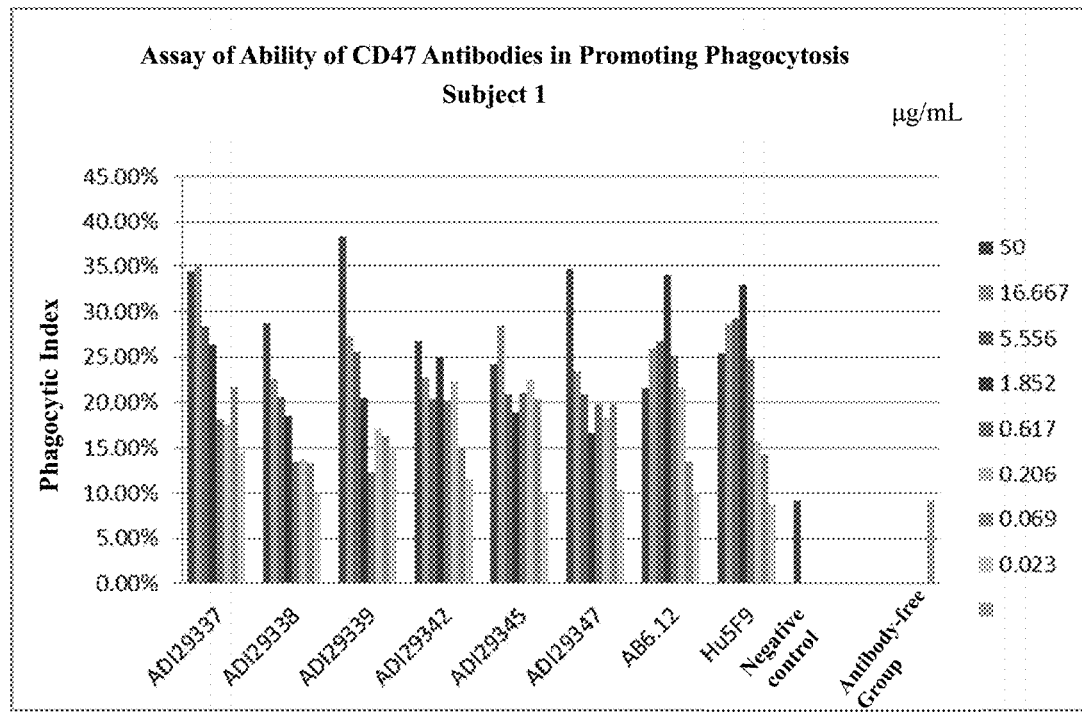
FIG. 5 shows an assay of ability of the antibodies of the present invention to promote the phagocytosis of tumor cells by macrophages.
Figure 6:
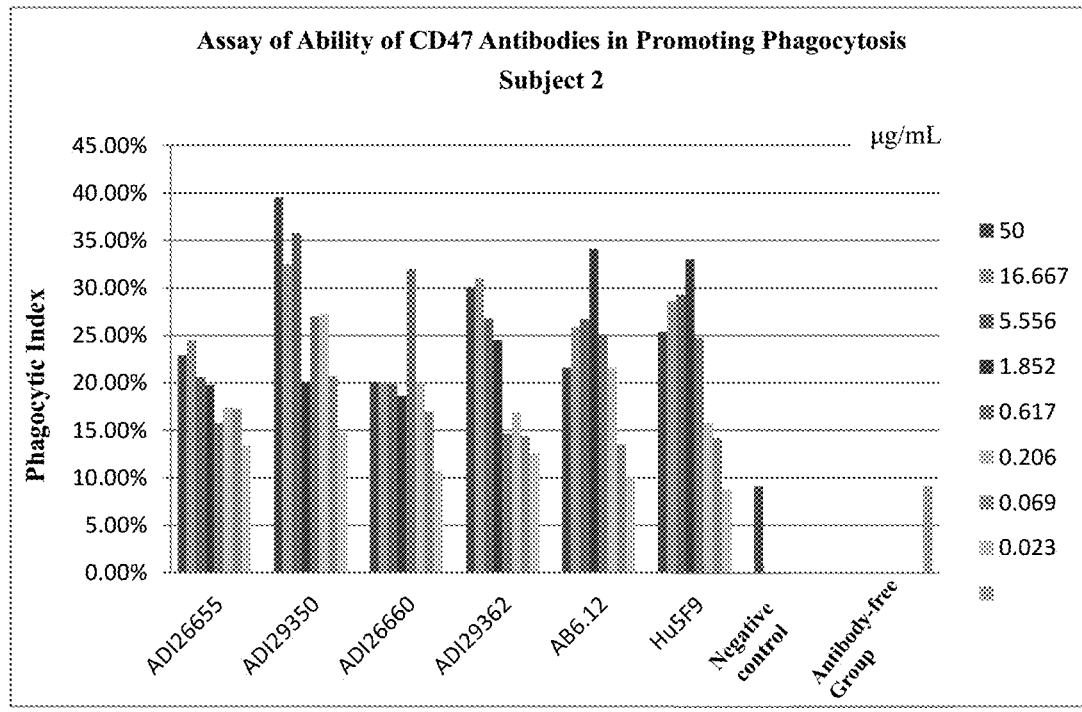
FIG. 6 shows an assay of ability of the antibodies of the present invention to promote the phagocytosis of tumor cells by macrophages.

ADI-29337, ADI-29338, ADI-29339, ADI-29342, ADI-29345 and ADI-29347 all have strong abilities in promoting the phagocytosis of tumor cells by macrophages, wherein the abilities of ADI-29337, ADI-29339 and ADI-29347 in promoting the phagocytosis of tumor cells by macrophages are higher than those of the control antibodies Hu5F9 and AB6.12; the abilities of ADI-29342, ADI-29345, ADI-29350 and ADI-29362 in promoting the phagocytosis of tumor cells by macrophages are comparable to those of the control antibodies Hu5F9 and AB6.12; and ADI-26655 and ADI-26660 have certain abilities in promoting the phagocytosis of tumor cells by macrophages (see FIG. 5 and FIG. 6).

Example 6: Assay of Activities of Anti-CD47 Antibodies of the Present Invention in Promoting Erythrocyte Agglutination Most of the anti-CD47 antibodies known in the prior art have the side effect of promoting erythrocyte agglutination, resulting in limited therapeutical use thereof. Therefore, the inventor further studied the influence of the antibodies disclosed in the present application on erythrocyte agglutination.

The Assay Method is as Follows:

Fresh human blood was collected, washed with PBS three times and then prepared into 10% human red blood cell suspension. The human red blood cells and the test antibodies (serially 3-fold diluted from a concentration of 60 ug/mL to the 11th concentration) were incubated at 37° C. for 2 to 6 h in a 96-well round-bottom plate. After the reaction was completed, pictures were taken, and results were judged. The criteria are as follows: if the red blood cells sunk at the well bottom and spread out like a net, then erythrocyte agglutination occurred (see the result of Hu5F9 in FIG. 7); and if the red blood cells sunk at the well bottom as dots, then erythrocyte agglutination did not occur (see the control in FIG. 7).

Figure 7:
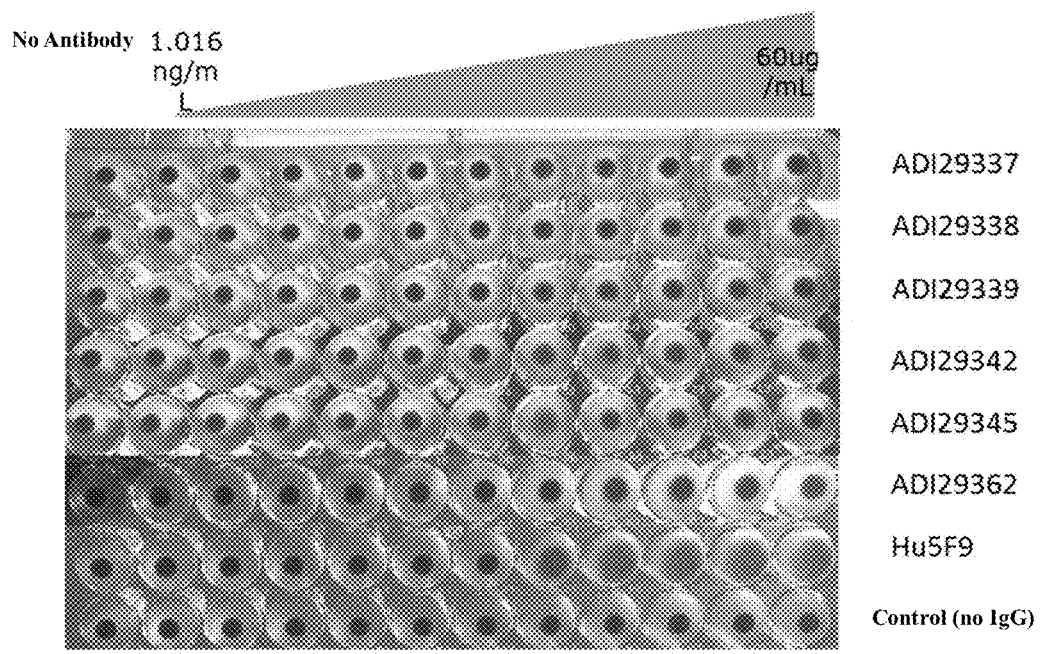
FIG. 7 shows assay results of activities of the anti-CD47 antibodies of the present invention in promoting erythrocyte agglutination.

In the assay described above, the erythrocyte agglutination results are shown in FIG. 7. It can be seen from FIG. 7 that the activities of ADI29337, ADI29338, ADI29339, ADI29342, ADI29345 and ADI29362 in promoting erythrocyte agglutination are very low, and are significantly lower than that of the control antibody Hu5F9. It can be seen that the antibodies disclosed herein have a significantly reduced effect in hemoagglutination, resulting in significantly reduced side effects in clinical treatment, and therefore can be widely used in the treatment of a variety of cancers.

The invention claimed is:

1. An isolated anti-CD47 monoclonal antibody or an antigen-binding fragment thereof, comprising: 3 heavy chain complementarity determining regions (CDRs) of a heavy chain variable region (HCDR1, HCDR2, HCDR3) and 3 light chain CDRs of a light chain variable region (LCDR1, LCDR2, LCDR3), wherein:

(i) HCDR1 comprises the amino acid sequence set forth in SEQ ID NO: 15, HCDR2 comprises the amino acid sequence set forth in SEQ ID NO: 21, HCDR3 comprises the amino acid sequence set forth in SEQ ID NO: 31, LCDR1 comprises the amino acid sequence set forth in SEQ ID NO: 36, LCDR2 comprises the amino acid sequence set forth in SEQ ID NO: 39, and LCDR3 comprises the amino acid sequence set forth in SEQ ID NO: 41;

(ii) HCDR1 comprises the amino acid sequence set forth in SEQ ID NO: 16, HCDR2 comprises the amino acid sequence set forth in SEQ ID NO: 22, HCDR3 comprises the amino acid sequence set forth in SEQ ID NO: 31, LCDR1 comprises the amino acid sequence set forth in SEQ ID NO: 36, LCDR2 comprises the amino acid sequence set forth in SEQ ID NO: 39, and LCDR3 comprises the amino acid sequence set forth in SEQ ID NO: 41;

(iii) HCDR1 comprises the amino acid sequence set forth in SEQ ID NO: 17, HCDR2 comprises the amino acid sequence set forth in SEQ ID NO: 23, HCDR3 comprises the amino acid sequence set forth in SEQ ID NO: 31, LCDR1 comprises the amino acid sequence set forth in SEQ ID NO: 36, LCDR2 comprises the amino acid sequence set forth in SEQ ID NO: 39, and LCDR3 comprises the amino acid sequence set forth in SEQ ID NO: 41;

(iv) HCDR1 comprises the amino acid sequence set forth in SEQ ID NO: 18, HCDR2 comprises the amino acid sequence set forth in SEQ ID NO: 24, HCDR3 comprises the amino acid sequence set forth in SEQ ID NO: 32, LCDR1 comprises the amino acid sequence set forth in SEQ ID NO: 36, LCDR2 comprises the amino acid sequence set forth in SEQ ID NO: 39, and LCDR3 comprises the amino acid sequence set forth in SEQ ID NO: 42;

(v) HCDR1 comprises the amino acid sequence set forth in SEQ ID NO: 17, HCDR2 comprises the amino acid sequence set forth in SEQ ID NO: 25, HCDR3 comprises the amino acid sequence set forth in SEQ ID NO: 33, LCDR1 comprises the amino acid sequence set forth in SEQ ID NO: 36, LCDR2 comprises the amino acid sequence set forth in SEQ ID NO: 39, and LCDR3 comprises the amino acid sequence set forth in SEQ ID NO: 42;

(vi) HCDR1 comprises the amino acid sequence set forth in SEQ ID NO: 19, HCDR2 comprises the amino acid sequence set forth in SEQ ID NO: 26, HCDR3 comprises the amino acid sequence set forth in SEQ ID NO: 32, LCDR1 comprises the amino acid sequence set forth in SEQ ID NO: 36, LCDR2 comprises the amino acid sequence set forth in SEQ ID NO: 39, and LCDR3 comprises the amino acid sequence set forth in SEQ ID NO: 42;

(vii) HCDR1 comprises the amino acid sequence set forth in SEQ ID NO: 16, HCDR2 comprises the amino acid sequence set forth in SEQ ID NO: 27, HCDR3 comprises the amino acid sequence set forth in SEQ ID NO: 34, LCDR1 comprises the amino acid sequence set forth in SEQ ID NO: 37, LCDR2 comprises the amino acid sequence set forth in SEQ ID NO: 40, and LCDR3 comprises the amino acid sequence set forth in SEQ ID NO: 43;

(viii) HCDR1 comprises the amino acid sequence v SEQ ID NO: 20, HCDR2 comprises the amino acid sequence set forth in SEQ ID NO: 28, HCDR3 comprises the amino acid sequence set forth in SEQ ID NO: 34, LCDR1 comprises the amino acid sequence set forth in SEQ ID NO: 37, LCDR2 comprises the amino acid sequence set forth in SEQ ID NO: 40, and LCDR3 comprises the amino acid sequence set forth in SEQ ID NO: 43;

(ix) HCDR1 comprises the amino acid sequence set forth in SEQ ID NO: 16, HCDR2 comprises the amino acid sequence set forth in SEQ ID NO: 29, HCDR3 comprises the amino acid sequence set forth in SEQ ID NO: 35, LCDR1 comprises the amino acid sequence set forth in SEQ ID NO: 38, LCDR2 comprises the amino acid sequence set forth in SEQ ID NO: 39, and LCDR3 comprises the amino acid sequence set forth in SEQ ID NO: 44; or (x) HCDR1 comprises the amino acid sequence set forth in SEQ ID NO: 20, HCDR2 comprises the amino acid sequence set forth in SEQ ID NO: 30, HCDR3 comprises the amino acid sequence set forth in SEQ ID NO: 35, LCDR1 comprises the amino acid sequence set forth in SEQ ID NO: 38, LCDR2 comprises the amino acid sequence set forth in SEQ ID NO: 39, and LCDR3 comprises the amino acid sequence set forth in SEQ ID NO: 44.

2. The isolated monoclonal antibody or the antigen-binding fragment thereof according to claim 1, comprising:
   (i) a heavy chain variable region having at least 90% identity to the amino acid sequence set forth in SEQ ID NOs: 45, 46 or 47, and/or a light chain variable region having at least 90% sequence identity to the amino acid sequence set forth in SEQ ID NO: 65,
   (ii) a heavy chain variable region having at least 90% identity to the amino acid sequence set forth in SEQ ID NOs: 48, 49 or 50, and/or a light chain variable region having at least 90% sequence identity to the amino acid sequence set forth in SEQ ID NO: 66,
   (iii) a heavy chain variable region having at least 90% identity to the amino acid sequence set forth in SEQ ID NOs: 51 or 52, and/or a light chain variable region having at least 90% sequence identity to the amino acid sequence set forth in SEQ ID NO: 67, or
   (iv) a heavy chain variable region having at least 90% identity to the amino acid sequence set forth in SEQ ID NOs: 53 or 54, and/or a light chain variable region having at least 90% sequence identity to the amino acid sequence set forth in SEQ ID NO: 68.

3. The isolated monoclonal antibody or the antigen-binding fragment thereof according to claim 1, comprising:
   (i) a heavy chain comprising an amino acid sequence having at least 90% sequence identity to the amino acid sequence set forth in SEQ ID NOs: 1, 3 and 4, and/or a light chain comprising an amino acid sequence having at least 90% sequence identity to the amino acid sequence set forth in SEQ ID NO: 2,
   (ii) a heavy chain comprising an amino acid sequence having at least 90% sequence identity to the amino acid sequence set forth in SEQ ID NOs: 5, 7 and 8, and/or a light chain comprising an amino acid sequence having at least 90% sequence identity to the amino acid sequence set forth in SEQ ID NO: 6,
   (iii) a heavy chain comprising an amino acid sequence having at least 90% sequence identity to the amino acid sequence set forth in SEQ ID NOs: 9 and 11, and/or a light chain comprising an amino acid sequence having at least 90% sequence identity to the amino acid sequence set forth in SEQ ID NO: 10, or
   (iv) a heavy chain comprising an amino acid sequence having at least 90% sequence identity to the amino acid sequence set forth in SEQ ID NOs: 12 and 14, and/or a light chain comprising an amino acid sequence having at least 90% sequence identity to the amino acid sequence set forth in SEQ ID NO: 13.

4. The isolated monoclonal antibody or the antigen-binding fragment thereof according to claim 1, wherein the antibody is a humanized antibody or a human antibody.

5. The isolated monoclonal antibody or the antigen-binding fragment thereof according to claim 1, wherein the antigen-binding fragment is selected from Fab, Fab'-SH, Fv, scFv and (Fab')$_2$ fragment.

6. The isolated monoclonal antibody or the antigen-binding fragment thereof according to claim 1, comprising framework sequences, wherein at least a portion of the framework sequences is consensus framework sequence in human.

7. An isolated nucleic acid, encoding the isolated anti-CD47 monoclonal antibody or the antigen-binding fragment thereof according to claim 1.

8. A vector comprising the nucleic acid according to claim 7.

9. A host cell comprising the vector according to claim 8, wherein the host cell is a prokaryocyte or a eukaryocyte.

10. A method for preparing anti-CD47 monoclonal antibodies or antigen-binding fragments thereof, comprising: cultivating the host cell according to claim 9 under conditions suitable for expressing and encoding the anti-CD47 monoclonal antibody or the antigen-binding fragment thereof.

11. An isolated anti-CD47 monoclonal antibody or an antigen-binding fragment thereof prepared by the method according to claim 10.

12. A pharmaceutical composition, comprising the anti-CD47 antibody or the antigen-binding fragment thereof according to claim 1, and a pharmaceutically acceptable carrier.

13. A method for treating a cancer or tumor, or for alleviating the symptoms of the cancer or tumor, in a human subject, comprising administering the pharmaceutical composition according to claim 12 at an effective dose to the human subject.

14. The method according to claim 13, wherein the cancer or the tumor is a hematologic tumor and solid tumor, selected from: acute myeloid leukemia (AML), chronic myeloid leukemia (CML), acute lymphocytic leukemia (ALL), chronic lymphocytic leukemia (CLL), non-Hodgkin's lymphoma (NHL), multiple myeloma (MM), lymphoma, breast cancer, head and neck cancer, gastric cancer, lung cancer, esophageal cancer, intestinal cancer, ovarian cancer, cervical cancer, liver cancer, renal cancer, pancreatic cancer, bladder cancer, colorectal cancer, neuroglioma, melanoma and other solid tumors.

15. The method according to claim 13, further comprising administering to the human subject one or more additional medicaments at an effective dose.

16. A method for detecting the presence of CD47 protein in a sample, comprising:
    (a) contacting the sample with the antibody or the antigen-binding fragment thereof according to claim 1; and
    (b) detecting formation of a complex between the antibody or the antigen-binding fragment thereof and CD47 protein.

17. A method for determining the efficacy of a cancer treatment, comprising: measuring the numbers of cancer cells expressing CD47 in a sample from a subject before and after the cancer treatment using the antibody or the antigen-binding fragment thereof according to claim 1, wherein a reduction in the cancer cells expressing CD47 subsequent to the treatment suggests that the cancer treatment is effective.

18. A pharmaceutical composition, comprising the anti-CD47 antibodies or antigen-binding fragments thereof according to claim 11, and a pharmaceutical carrier.

19. A method for detecting presence of CD47 protein in a sample, comprising:
    (a) contacting the sample with the antibody or antigen-binding fragment thereof according to claim 11; and
    (b) detecting formation of a complex between the antibody or the antigen-binding fragment thereof and the CD47 protein.

* * * * *

SEQUENCE LISTING

```
<160> NUMBER OF SEQ ID NOS: 80

<210> SEQ ID NO 1
<211> LENGTH: 444
<212> TYPE: PRT
<213> ORGANISM: Artificial Sequence
<220> FEATURE:
<223> OTHER INFORMATION: ADI29337 HC

<400> SEQUENCE: 1
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn His Tyr
            20                  25                  30

Tyr Trp Ser Trp Ile Arg Gln Pro Pro Gly Lys Gly Leu Glu Trp Ile
        35                  40                  45

Gly Ala Ile Tyr Tyr Ser Gly Ser Thr Arg Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asp Pro Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
```

```
                    325                 330                 335
Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

<210> SEQ ID NO 2
<211> LENGTH: 215
<212> TYPE: PRT
<213> ORGANISM: Artificial Sequence
<220> FEATURE:
<223> OTHER INFORMATION: LC

<400> SEQUENCE: 2

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Leu His Pro Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 3
<211> LENGTH: 444
<212> TYPE: PRT

<210> ORGANISM: Artificial Sequence
<220> FEATURE:
<223> OTHER INFORMATION: ADI29338 HC

<400> SEQUENCE: 3

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Thr Ile Tyr Tyr Ser Gly Ser Thr Arg Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asp Pro Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
```

```
                385                 390                 395                 400
Ser Phe Phe Leu Tyr Ser Lys Leu Thr Val Asp Lys Ser Arg Trp Gln
                    405                 410                 415

Gln Gly Asn Val Phe Ser Cys Ser Val Met His Glu Ala Leu His Asn
                    420                 425                 430

His Tyr Thr Gln Lys Ser Leu Ser Leu Ser Pro Gly
                    435                 440

<210> SEQ ID NO 4
<211> LENGTH: 444
<212> TYPE: PRT
<213> ORGANISM: Artificial Sequence
<220> FEATURE:
<223> OTHER INFORMATION: ADI29339 HC

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser His Tyr
                20                  25                  30

Tyr Trp Ser Trp Ile Arg Gln Pro Pro Gly Lys Gly Leu Glu Trp Ile
            35                  40                  45

Gly Val Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asp Pro Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
            305                 310                 315                 320
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
            435                 440

<210> SEQ ID NO 5
<211> LENGTH: 444
<212> TYPE: PRT
<213> ORGANISM: Artificial Sequence
<220> FEATURE:
<223> OTHER INFORMATION: ADI29342 HC

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Met His Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Thr Gly Ser Ala Ala Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
```

```
                225                 230                 235                 240
Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 6
<211> LENGTH: 214
<212> TYPE: PRT
<213> ORGANISM: Artificial Sequence
<220> FEATURE:
<223> OTHER INFORMATION: LC

<400> SEQUENCE: 6

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Ser Phe Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
            145                 150                 155                 160
        Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Glu Cys
                        210

<210> SEQ ID NO 7
<211> LENGTH: 444
<212> TYPE: PRT
<213> ORGANISM: Artificial Sequence
<220> FEATURE:
<223> OTHER INFORMATION: ADI 29345 HC

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser His Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Val Thr Thr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Thr Gly Ser Thr Ala Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
```

```
            290                 295                 300
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 8
<211> LENGTH: 444
<212> TYPE: PRT
<213> ORGANISM: Artificial Sequence
<220> FEATURE:
<223> OTHER INFORMATION: ADI 29347 HC

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ala Asn Tyr
            20                  25                  30

Tyr Trp Ser Trp Ile Arg Gln Pro Pro Gly Lys Gly Leu Glu Trp Ile
        35                  40                  45

Gly Tyr Thr Tyr Phe Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Thr Gly Ser Ala Ala Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
```

```
                210                 215                 220
Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
                290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
                435                 440

<210> SEQ ID NO 9
<211> LENGTH: 444
<212> TYPE: PRT
<213> ORGANISM: Artificial Sequence
<220> FEATURE:
<223> OTHER INFORMATION: ADI 26655 HC

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
                35                  40                  45

Gly Tyr Ile Tyr Tyr Ser Gly Ser Thr Thr Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Lys Lys Arg Phe Phe Asp Leu Trp Gly Gln Gly Thr Thr Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
```

```
            130                 135                 140
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
        210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 10
<211> LENGTH: 215
<212> TYPE: PRT
<213> ORGANISM: Artificial Sequence
<220> FEATURE:
<223> OTHER INFORMATION: LC

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
```

```
                50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Val Lys Ser Tyr Ser Pro
                 85                  90                  95

Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 11
<211> LENGTH: 444
<212> TYPE: PRT
<213> ORGANISM: Artificial Sequence
<220> FEATURE:
<223> OTHER INFORMATION: ADI 29350 HC

<400> SEQUENCE: 11

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Glu His Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Phe Thr Glu Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Lys Lys Arg Phe Phe Asp Leu Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
```

```
                195                 200                 205
Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 12
<211> LENGTH: 444
<212> TYPE: PRT
<213> ORGANISM: Artificial Sequence
<220> FEATURE:
<223> OTHER INFORMATION: ADI 26660 HC

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Ser Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Lys Gln Lys His Phe Asp Ile Trp Gly Gln Gly Thr Met Val Thr
            100                 105                 110

Val Ser Ser Ala Ser Thr Lys Gly Pro Ser Val Phe Pro Leu Ala Pro
```

```
            115                 120                 125
Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 13
<211> LENGTH: 214
<212> TYPE: PRT
<213> ORGANISM: Artificial Sequence
<220> FEATURE:
<223> OTHER INFORMATION: LC

<400> SEQUENCE: 13

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
```

```
            35                  40                  45
Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Asn His His Pro Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 444
<212> TYPE: PRT
<213> ORGANISM: Artificial Sequence
<220> FEATURE:
<223> OTHER INFORMATION: ADI 29362 HC

<400> SEQUENCE: 14

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Glu His Tyr
             20                  25                  30

Tyr Trp Ser Trp Ile Arg Gln Pro Pro Gly Lys Gly Leu Glu Trp Ile
         35                  40                  45

Gly Ala Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Lys Gln Lys His Phe Asp Ile Trp Gly Gln Gly Thr Met Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
```

```
                180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
            245                 250                 255
Val Thr Cys Val Val Val Asp Val Ser His Glu Asp Pro Glu Val Lys
        260                 265                 270
Phe Asn Trp Tyr Val Asp Gly Val Glu Val His Asn Ala Lys Thr Lys
    275                 280                 285
Pro Arg Glu Glu Gln Tyr Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
            325                 330                 335
Ala Lys Gly Gln Pro Arg Glu Pro Gln Val Tyr Thr Leu Pro Pro Ser
        340                 345                 350
Arg Asp Glu Leu Thr Lys Asn Gln Val Ser Leu Thr Cys Leu Val Lys
    355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
            405                 410                 415
Gln Gly Asn Val Phe Ser Cys Ser Val Met His Glu Ala Leu His Asn
        420                 425                 430
His Tyr Thr Gln Lys Ser Leu Ser Leu Ser Pro Gly
    435                 440

<210> SEQ ID NO 15
<211> LENGTH: 9
<212> TYPE: PRT
<213> ORGANISM: Artificial Sequence
<220> FEATURE:
<223> OTHER INFORMATION: HCDR1

<400> SEQUENCE: 15

Gly Ser Ile Asn His Tyr Tyr Trp Ser
1               5

<210> SEQ ID NO 16
<211> LENGTH: 9
<212> TYPE: PRT
<213> ORGANISM: Artificial Sequence
<220> FEATURE:
<223> OTHER INFORMATION: HCDR1

<400> SEQUENCE: 16

Gly Ser Ile Ser Ser Tyr Tyr Trp Ser
1               5

<210> SEQ ID NO 17
<211> LENGTH: 9
```

```
<212> TYPE: PRT
<213> ORGANISM: Artificial Sequence
<220> FEATURE:
<223> OTHER INFORMATION: HCDR1

<400> SEQUENCE: 17

Gly Ser Ile Ser His Tyr Tyr Trp Ser
1               5

<210> SEQ ID NO 18
<211> LENGTH: 9
<212> TYPE: PRT
<213> ORGANISM: Artificial Sequence
<220> FEATURE:
<223> OTHER INFORMATION: HCDR1

<400> SEQUENCE: 18

Gly Ser Ile Met His Tyr Tyr Trp Ser
1               5

<210> SEQ ID NO 19
<211> LENGTH: 9
<212> TYPE: PRT
<213> ORGANISM: Artificial Sequence
<220> FEATURE:
<223> OTHER INFORMATION: HCDR1

<400> SEQUENCE: 19

Gly Ser Ile Ala Asn Tyr Tyr Trp Ser
1               5

<210> SEQ ID NO 20
<211> LENGTH: 9
<212> TYPE: PRT
<213> ORGANISM: Artificial Sequence
<220> FEATURE:
<223> OTHER INFORMATION: HCDR1

<400> SEQUENCE: 20

Gly Ser Ile Glu His Tyr Tyr Trp Ser
1               5

<210> SEQ ID NO 21
<211> LENGTH: 16
<212> TYPE: PRT
<213> ORGANISM: Artificial Sequence
<220> FEATURE:
<223> OTHER INFORMATION: HCDR2

<400> SEQUENCE: 21

Ala Ile Tyr Tyr Ser Gly Ser Thr Arg Tyr Asn Pro Ser Leu Lys Ser
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: HCDR2

<400> SEQUENCE: 22

Thr Ile Tyr Tyr Ser Gly Ser Thr Arg Tyr Asn Pro Ser Leu Lys Ser
1               5                   10                  15

<210> SEQ ID NO 23
<211> LENGTH: 16
<212> TYPE: PRT
```

```
<213> ORGANISM: Artificial Sequence
<220> FEATURE:
<223> OTHER INFORMATION: HCDR2

<400> SEQUENCE: 23

Val Ile Tyr Tyr Ser Gly Ser Thr Asn Tyr Asn Pro Ser Leu Lys Ser
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: HCDR2

<400> SEQUENCE: 24

Tyr Ile Tyr Tyr Ser Gly Ser Thr Asn Tyr Asn Pro Ser Leu Lys Ser
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: HCDR2

<400> SEQUENCE: 25

Tyr Ile Tyr Tyr Ser Gly Val Thr Thr Tyr Asn Pro Ser Leu Lys Ser
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: HCDR2

<400> SEQUENCE: 26

Tyr Thr Tyr Phe Ser Gly Ser Thr Asn Tyr Asn Pro Ser Leu Lys Ser
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: HCDR2

<400> SEQUENCE: 27

Tyr Ile Tyr Tyr Ser Gly Ser Thr Thr Tyr Asn Pro Ser Leu Lys Ser
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: HCDR2

<400> SEQUENCE: 28

Tyr Ile Tyr Tyr Ser Gly Phe Thr Glu Tyr Asn Pro Ser Leu Lys Ser
1               5                   10                  15

<210> SEQ ID NO 29
<211> LENGTH: 16
<212> TYPE: PRT
<213> ORGANISM: Artificial Sequence
```

```
<220> FEATURE:
<223> OTHER INFORMATION: HCDR2

<400> SEQUENCE: 29

Ser Ile Tyr Tyr Ser Gly Ser Thr Asn Tyr Asn Pro Ser Leu Lys Ser
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: HCDR2

<400> SEQUENCE: 30

Ala Ile Tyr Tyr Ser Gly Ser Thr Asn Tyr Asn Pro Ser Leu Lys Ser
1               5                   10                  15

<210> SEQ ID NO 31
<211> LENGTH: 9
<212> TYPE: PRT
<213> ORGANISM: Artificial Sequence
<220> FEATURE:
<223> OTHER INFORMATION: HCDR3

<400> SEQUENCE: 31

Ala Arg Gly Lys Ser Ala Phe Asp Pro
1               5

<210> SEQ ID NO 32
<211> LENGTH: 9
<212> TYPE: PRT
<213> ORGANISM: Artificial Sequence
<220> FEATURE:
<223> OTHER INFORMATION: HCDR3

<400> SEQUENCE: 32

Ala Arg Gly Lys Thr Gly Ser Ala Ala
1               5

<210> SEQ ID NO 33
<211> LENGTH: 9
<212> TYPE: PRT
<213> ORGANISM: Artificial Sequence
<220> FEATURE:
<223> OTHER INFORMATION: HCDR3

<400> SEQUENCE: 33

Ala Arg Gly Lys Thr Gly Ser Thr Ala
1               5

<210> SEQ ID NO 34
<211> LENGTH: 9
<212> TYPE: PRT
<213> ORGANISM: Artificial Sequence
<220> FEATURE:
<223> OTHER INFORMATION: HCDR3

<400> SEQUENCE: 34

Ala Arg Lys Lys Arg Phe Phe Asp Leu
1               5

<210> SEQ ID NO 35
<211> LENGTH: 9
<212> TYPE: PRT
<213> ORGANISM: Artificial Sequence
<220> FEATURE:
```

```
<223> OTHER INFORMATION: HCDR3

<400> SEQUENCE: 35

Ala Arg Lys Gln Lys His Phe Asp Ile
1               5

<210> SEQ ID NO 36
<211> LENGTH: 11
<212> TYPE: PRT
<213> ORGANISM: Artificial Sequence
<220> FEATURE:
<223> OTHER INFORMATION: LCDR1

<400> SEQUENCE: 36

Arg Ala Ser Gln Gly Ile Ser Arg Trp Leu Ala
1               5                   10

<210> SEQ ID NO 37
<211> LENGTH: 11
<212> TYPE: PRT
<213> ORGANISM: Artificial Sequence
<220> FEATURE:
<223> OTHER INFORMATION: LCDR1

<400> SEQUENCE: 37

Arg Ala Ser Gln Ser Ile Ser Ser Trp Leu Ala
1               5                   10

<210> SEQ ID NO 38
<211> LENGTH: 11
<212> TYPE: PRT
<213> ORGANISM: Artificial Sequence
<220> FEATURE:
<223> OTHER INFORMATION: LCDR1

<400> SEQUENCE: 38

Arg Ala Ser Gln Gly Ile Ser Ser Trp Leu Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: LCDR2

<400> SEQUENCE: 39

Ala Ala Ser Ser Leu Gln Ser
1               5

<210> SEQ ID NO 40
<211> LENGTH: 7
<212> TYPE: PRT
<213> ORGANISM: Artificial Sequence
<220> FEATURE:
<223> OTHER INFORMATION: LCDR2

<400> SEQUENCE: 40

Lys Ala Ser Ser Leu Glu Ser
1               5

<210> SEQ ID NO 41
<211> LENGTH: 10
<212> TYPE: PRT
<213> ORGANISM: Artificial Sequence
<220> FEATURE:
<223> OTHER INFORMATION: LCDR3
```

```
<400> SEQUENCE: 41

Gln Gln Ala Asp Leu His Pro Pro Leu Thr
1               5                   10

<210> SEQ ID NO 42
<211> LENGTH: 9
<212> TYPE: PRT
<213> ORGANISM: Artificial Sequence
<220> FEATURE:
<223> OTHER INFORMATION: LCDR3

<400> SEQUENCE: 42

Gln Gln Thr Val Ser Phe Pro Ile Thr
1               5

<210> SEQ ID NO 43
<211> LENGTH: 10
<212> TYPE: PRT
<213> ORGANISM: Artificial Sequence
<220> FEATURE:
<223> OTHER INFORMATION: LCDR3

<400> SEQUENCE: 43

Gln Gln Val Lys Ser Tyr Ser Pro Leu Thr
1               5                   10

<210> SEQ ID NO 44
<211> LENGTH: 9
<212> TYPE: PRT
<213> ORGANISM: Artificial Sequence
<220> FEATURE:
<223> OTHER INFORMATION: LCDR3

<400> SEQUENCE: 44

Gln Gln Val Asn His His Pro Trp Thr
1               5

<210> SEQ ID NO 45
<211> LENGTH: 115
<212> TYPE: PRT
<213> ORGANISM: Artificial Sequence
<220> FEATURE:
<223> OTHER INFORMATION: VH protein

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn His Tyr
            20                  25                  30

Tyr Trp Ser Trp Ile Arg Gln Pro Pro Gly Lys Gly Leu Glu Trp Ile
        35                  40                  45

Gly Ala Ile Tyr Tyr Ser Gly Ser Thr Arg Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asp Pro Trp Gly Gln Gly Thr Leu Val Thr
            100                 105                 110

Val Ser Ser
        115
```

```
<210> SEQ ID NO 46
<211> LENGTH: 115
<212> TYPE: PRT
<213> ORGANISM: Artificial Sequence
<220> FEATURE:
<223> OTHER INFORMATION: VH protein

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Thr Ile Tyr Tyr Ser Gly Ser Thr Arg Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asp Pro Trp Gly Gln Gly Thr Leu Val Thr
            100                 105                 110

Val Ser Ser
        115

<210> SEQ ID NO 47
<211> LENGTH: 115
<212> TYPE: PRT
<213> ORGANISM: Artificial Sequence
<220> FEATURE:
<223> OTHER INFORMATION: VH protein

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser His Tyr
            20                  25                  30

Tyr Trp Ser Trp Ile Arg Gln Pro Pro Gly Lys Gly Leu Glu Trp Ile
        35                  40                  45

Gly Val Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Ser Ala Phe Asp Pro Trp Gly Gln Gly Thr Leu Val Thr
            100                 105                 110

Val Ser Ser
        115

<210> SEQ ID NO 48
<211> LENGTH: 115
<212> TYPE: PRT
<213> ORGANISM: Artificial Sequence
<220> FEATURE:
<223> OTHER INFORMATION: VH protein

<400> SEQUENCE: 48

Gln Val Gln Leu Gln Glu Ser Gly Pro Gly Leu Val Lys Pro Ser Glu
```

-continued

```
              1               5                  10                 15
            Thr Leu Ser Leu Thr Cys Thr Val Ser Gly Gly Ser Ile Met His Tyr
                        20                  25                 30

Tyr Trp Ser Trp Ile Arg Gln Pro Pro Gly Lys Gly Leu Glu Trp Ile
                        35                  40                 45

Gly Tyr Ile Tyr Tyr Ser Gly Ser Thr Asn Tyr Asn Pro Ser Leu Lys
                        50                  55                 60

Ser Arg Val Thr Ile Ser Val Asp Thr Ser Lys Asn Gln Phe Ser Leu
             65                 70                  75                 80

Lys Leu Ser Ser Val Thr Ala Ala Asp Thr Ala Val Tyr Tyr Cys Ala
                        85                  90                 95

Arg Gly Lys Thr Gly Ser Ala Ala Trp Gly Gln Gly Thr Leu Val Thr
                        100                 105                110

Val Ser Ser
                        115

<210> SEQ ID NO 49
<211> LENGTH: 115
<212> TYPE: PRT
<213> ORGANISM: Artificial Sequence
<220> FEATURE:
<223> OTHER INFORMATION: VH protein

<400> SEQUENCE: 49

Gln Val Gln Leu Gln Glu Ser Gly Pro Gly Leu Val Lys Pro Ser Glu
             1               5                  10                 15

Thr Leu Ser Leu Thr Cys Thr Val Ser Gly Gly Ser Ile Ser His Tyr
                        20                  25                 30

Tyr Trp Ser Trp Ile Arg Gln Pro Pro Gly Lys Gly Leu Glu Trp Ile
                        35                  40                 45

Gly Tyr Ile Tyr Tyr Ser Gly Val Thr Thr Tyr Asn Pro Ser Leu Lys
                        50                  55                 60

Ser Arg Val Thr Ile Ser Val Asp Thr Ser Lys Asn Gln Phe Ser Leu
             65                 70                  75                 80

Lys Leu Ser Ser Val Thr Ala Ala Asp Thr Ala Val Tyr Tyr Cys Ala
                        85                  90                 95

Arg Gly Lys Thr Gly Ser Thr Ala Trp Gly Gln Gly Thr Leu Val Thr
                        100                 105                110

Val Ser Ser
                        115

<210> SEQ ID NO 50
<211> LENGTH: 115
<212> TYPE: PRT
<213> ORGANISM: Artificial Sequence
<220> FEATURE:
<223> OTHER INFORMATION: VH protein

<400> SEQUENCE: 50

Gln Val Gln Leu Gln Glu Ser Gly Pro Gly Leu Val Lys Pro Ser Glu
             1               5                  10                 15

Thr Leu Ser Leu Thr Cys Thr Val Ser Gly Gly Ser Ile Ala Asn Tyr
                        20                  25                 30

Tyr Trp Ser Trp Ile Arg Gln Pro Pro Gly Lys Gly Leu Glu Trp Ile
                        35                  40                 45

Gly Tyr Thr Tyr Tyr Phe Ser Gly Ser Thr Asn Tyr Asn Pro Ser Leu Lys
                        50                  55                 60
```

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Lys Thr Gly Ser Ala Ala Trp Gly Gln Gly Thr Leu Val Thr
            100                 105                 110

Val Ser Ser
        115

<210> SEQ ID NO 51
<211> LENGTH: 115
<212> TYPE: PRT
<213> ORGANISM: Artificial Sequence
<220> FEATURE:
<223> OTHER INFORMATION: VH protein

<400> SEQUENCE: 51

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
                 20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Lys Lys Arg Phe Phe Asp Leu Trp Gly Gln Gly Thr Thr Val Thr
            100                 105                 110

Val Ser Ser
        115

<210> SEQ ID NO 52
<211> LENGTH: 115
<212> TYPE: PRT
<213> ORGANISM: Artificial Sequence
<220> FEATURE:
<223> OTHER INFORMATION: VH protein

<400> SEQUENCE: 52

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Glu His Tyr
                 20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Phe Thr Glu Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Lys Lys Arg Phe Phe Asp Leu Trp Gly Gln Gly Thr Thr Val Thr
            100                 105                 110

Val Ser Ser
        115
```

<210> SEQ ID NO 53
<211> LENGTH: 115
<212> TYPE: PRT
<213> ORGANISM: Artificial Sequence
<220> FEATURE:
<223> OTHER INFORMATION: VH protein

<400> SEQUENCE: 53

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Ser Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Lys Gln Lys His Phe Asp Ile Trp Gly Gln Gly Thr Met Val Thr
            100                 105                 110

Val Ser Ser
        115
```

<210> SEQ ID NO 54
<211> LENGTH: 115
<212> TYPE: PRT
<213> ORGANISM: Artificial Sequence
<220> FEATURE:
<223> OTHER INFORMATION: VH protein

<400> SEQUENCE: 54

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu His Tyr
            20                  25                  30

Tyr Trp Ser Trp Ile Arg Gln Pro Pro Gly Lys Gly Leu Glu Trp Ile
        35                  40                  45

Gly Ala Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Lys Gln Lys His Phe Asp Ile Trp Gly Gln Gly Thr Met Val Thr
            100                 105                 110

Val Ser Ser
        115
```

<210> SEQ ID NO 55
<211> LENGTH: 345
<212> TYPE: DNA
<213> ORGANISM: Artificial Sequence
<220> FEATURE:
<223> OTHER INFORMATION: VH DNA

<400> SEQUENCE: 55

| caggtgcagc tgcaggagtc gggcccagga ctggtgaagc cttcggagac cctgtccctc | 60 |
| acctgcactg tctctggtgg ctccatcaat cattactact ggagctggat ccggcagccc | 120 |
| ccagggaagg gactggagtg gattggggcg atctattaca gtgggagcac ccggtacaac | 180 |
| ccctccctca agagtcgagt caccatatca gtagacacgt ccaagaacca gttctccctg | 240 |
| aagctgagtt ctgtgaccgc cgcagacacg gcggtgtact actgcgccag gggtaagagt | 300 |
| gcattcgacc catggggaca gggtacattg gtcaccgtct cctca | 345 |

<210> SEQ ID NO 56
<211> LENGTH: 345
<212> TYPE: DNA
<213> ORGANISM: Artificial Sequence
<220> FEATURE:
<223> OTHER INFORMATION: VH DNA

<400> SEQUENCE: 56

| caggtgcagc tgcaggagtc gggcccagga ctggtgaagc cttcggagac cctgtccctc | 60 |
| acctgcactg tctctggtgg ctccatcagt agttactact ggagctggat ccggcagccc | 120 |
| ccagggaagg gactggagtg gattgggacg atctattaca gtgggagcac ccggtacaac | 180 |
| ccctccctca agagtcgagt caccatatca gtagacacgt ccaagaacca gttctccctg | 240 |
| aagctgagtt ctgtgaccgc cgcagacacg gcggtgtact actgcgccag gggtaagagt | 300 |
| gcattcgacc catggggaca gggtacattg gtcaccgtct cctca | 345 |

<210> SEQ ID NO 57
<211> LENGTH: 345
<212> TYPE: DNA
<213> ORGANISM: Artificial Sequence
<220> FEATURE:
<223> OTHER INFORMATION: VH DNA

<400> SEQUENCE: 57

| caggtgcagc tgcaggagtc gggcccagga ctggtgaagc cttcggagac cctgtccctc | 60 |
| acctgcactg tctctggtgg ctccatcagt cattactact ggagctggat ccggcagccc | 120 |
| ccagggaagg gactggagtg gattggggtg atctattata gtgggagcac caactacaac | 180 |
| ccctccctca agagtcgagt caccatatca gtagacacgt ccaagaacca gttctccctg | 240 |
| aagctgagtt ctgtgaccgc cgcagacacg gcggtgtact actgcgccag gggtaagagt | 300 |
| gcattcgacc catggggaca gggtacattg gtcaccgtct cctca | 345 |

<210> SEQ ID NO 58
<211> LENGTH: 345
<212> TYPE: DNA
<213> ORGANISM: Artificial Sequence
<220> FEATURE:
<223> OTHER INFORMATION: VH DNA

<400> SEQUENCE: 58

| caggtgcagc tgcaggagtc gggcccagga ctggtgaagc cttcggagac cctgtccctc | 60 |
| acctgcactg tctctggtgg ctccatcatg cattactact ggagctggat ccggcagccc | 120 |
| ccagggaagg gactggagtg gattgggtat atctattaca gtgggagcac caactacaac | 180 |
| ccctccctca agagtcgagt caccatatca gtagacacgt ccaagaacca gttctccctg | 240 |
| aagctgagtt ctgtgaccgc cgcagacacg gcggtgtact actgcgccag gggtaagacg | 300 |
| ggatctgccg catggggaca gggtacattg gtcaccgtct cctca | 345 |

<210> SEQ ID NO 59
<211> LENGTH: 345
<212> TYPE: DNA
<213> ORGANISM: Artificial Sequence
<220> FEATURE:
<223> OTHER INFORMATION: VH DNA

<400> SEQUENCE: 59

```
caggtgcagc tgcaggagtc gggcccagga ctggtgaagc cttcggagac cctgtccctc      60
acctgcactg tctctggtgg ctccatcagt cattactact ggagctggat ccggcagccc     120
ccagggaagg gactggagtg gattgggtat atctattaca gtggggttac acttacaac      180
ccctccctca agagtcgagt caccatatca gtagacacg ccaagaacca gttctccctg      240
aagctgagtt ctgtgaccgc cgcagacacg gcggtgtact actgcgccag ggtaagacg      300
ggatctaccg catggggaca gggtacattg gtcaccgtct cctca                     345
```

<210> SEQ ID NO 60
<211> LENGTH: 345
<212> TYPE: DNA
<213> ORGANISM: Artificial Sequence
<220> FEATURE:
<223> OTHER INFORMATION: VH DNA

<400> SEQUENCE: 60

```
caggtgcagc tgcaggagtc gggcccagga ctggtgaagc cttcggagac cctgtccctc      60
acctgcactg tctctggtgg ctccatcgct aattactact ggagctggat ccggcagccc     120
ccagggaagg gactggagtg gattgggtat acctatttta gtgggagtac caactacaac    180
ccctccctca agagtcgagt caccatatca gtagacacg ccaagaacca gttctccctg      240
aagctgagtt ctgtgaccgc cgcagacacg gcggtgtact actgcgccag ggtaagacg      300
ggatctgccg catggggaca gggtacattg gtcaccgtct cctca                     345
```

<210> SEQ ID NO 61
<211> LENGTH: 345
<212> TYPE: DNA
<213> ORGANISM: Artificial Sequence
<220> FEATURE:
<223> OTHER INFORMATION: VH DNA

<400> SEQUENCE: 61

```
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac cacgtacaac    180
ccctccctca agagtcgagt caccatatca gtagacacgt ccaagaacca gttctccctg    240
aagctgagtt ctgtgaccgc cgcagacacg gcggtgtact actgcgccag aaagaaaaga   300
ttcttcgacc tatggggcca gggaacaact gtcaccgtct cctca                    345
```

<210> SEQ ID NO 62
<211> LENGTH: 345
<212> TYPE: DNA
<213> ORGANISM: Artificial Sequence
<220> FEATURE:
<223> OTHER INFORMATION: VH DNA

<400> SEQUENCE: 62

```
caggtgcagc tgcaggagtc gggcccagga ctggtgaagc cttcggagac cctgtccctc      60
acctgcactg tctctggtgg ctccatcgag cattactact ggagctggat ccggcagccc    120
```

```
ccagggaagg gactggagtg gattgggtat atctattaca gtgggtttac cgagtacaac    180
ccctccctca agagtcgagt caccatatca gtagacacgt ccaagaacca gttctccctg    240
aagctgagtt ctgtgaccgc cgcagacacg gcggtgtact actgcgccag aaagaaaaga    300
ttcttcgacc tatggggcca gggaacaact gtcaccgtct cctca                    345

<210> SEQ ID NO 63
<211> LENGTH: 345
<212> TYPE: DNA
<213> ORGANISM: Artificial Sequence
<220> FEATURE:
<223> OTHER INFORMATION: VH DNA

<400> SEQUENCE: 63
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattgggtca atctattaca gtgggagcac caactacaac    180
ccctccctca agagtcgagt caccatatca gtagacacgt ccaagaacca gttctccctg    240
aagctgagtt ctgtgaccgc cgcagacacg gcggtgtact actgcgccag aaagcaaaaa    300
cacttcgaca tatggggtca gggtacaatg gtcaccgtct cctca                    345

<210> SEQ ID NO 64
<211> LENGTH: 345
<212> TYPE: DNA
<213> ORGANISM: Artificial Sequence
<220> FEATURE:
<223> OTHER INFORMATION: VH DNA

<400> SEQUENCE: 64
caggtgcagc tgcaggagtc gggcccagga ctggtgaagc cttcggagac cctgtccctc     60
acctgcactg tctctggtgg ctccatcgag cattactact ggagctggat ccggcagccc    120
ccagggaagg gactggagtg gattggggcg atctattact cggggagcac caactacaac    180
ccctccctca agagtcgagt caccatatca gtagacacgt ccaagaacca gttctccctg    240
aagctgagtt ctgtgaccgc cgcagacacg gcggtgtact actgcgccag aaagcaaaaa    300
cacttcgaca tatggggtca gggtacaatg gtcaccgtct cctca                    345

<210> SEQ ID NO 65
<211> LENGTH: 108
<212> TYPE: PRT
<213> ORGANISM: Artificial Sequence
<220> FEATURE:
<223> OTHER INFORMATION: VL protein

<400> SEQUENCE: 65

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Leu His Pro Pro
                85                  90                  95
```

```
Leu Thr Phe Gly Gly Gly Thr Lys Val Glu Ile Lys
            100                 105
```

<210> SEQ ID NO 66
<211> LENGTH: 107
<212> TYPE: PRT
<213> ORGANISM: Artificial Sequence
<220> FEATURE:
<223> OTHER INFORMATION: VL protein

<400> SEQUENCE: 66

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Ser Phe Pro Ile
                85                  90                  95

Thr Phe Gly Gly Gly Thr Lys Val Glu Ile Lys
            100                 105
```

<210> SEQ ID NO 67
<211> LENGTH: 108
<212> TYPE: PRT
<213> ORGANISM: Artificial Sequence
<220> FEATURE:
<223> OTHER INFORMATION: VL protein

<400> SEQUENCE: 67

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Val Lys Ser Tyr Ser Pro
                85                  90                  95

Leu Thr Phe Gly Gly Gly Thr Lys Val Glu Ile Lys
            100                 105
```

<210> SEQ ID NO 68
<211> LENGTH: 107
<212> TYPE: PRT
<213> ORGANISM: Artificial Sequence
<220> FEATURE:
<223> OTHER INFORMATION: VL protein

<400> SEQUENCE: 68

```
Asp Ile Gln Met Thr Gln Ser Pro Ser Ser Val Ser Ala Ser Val Gly
1               5                   10                  15
```

```
Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Asn His His Pro Trp
                85                  90                  95

Thr Phe Gly Gly Gly Thr Lys Val Glu Ile Lys
            100                 105

<210> SEQ ID NO 69
<211> LENGTH: 9
<212> TYPE: PRT
<213> ORGANISM: Artificial Sequence
<220> FEATURE:
<223> OTHER INFORMATION: HCDR1
<220> FEATURE:
<221> NAME/KEY: misc_feature
<222> LOCATION: (4)..(4)
<223> OTHER INFORMATION: Xaa selected from N, S, M, A or E
<220> FEATURE:
<221> NAME/KEY: misc_feature
<222> LOCATION: (5)..(5)
<223> OTHER INFORMATION: Xaa selected from H, S or N

<400> SEQUENCE: 69

Gly Ser Ile Xaa Xaa Tyr Tyr Trp Ser
1               5

<210> SEQ ID NO 70
<211> LENGTH: 16
<212> TYPE: PRT
<213> ORGANISM: Artificial Sequence
<220> FEATURE:
<223> OTHER INFORMATION: HCDR2
<220> FEATURE:
<221> NAME/KEY: misc_feature
<222> LOCATION: (1)..(1)
<223> OTHER INFORMATION: Xaa selected from A, T, V, Y or S
<220> FEATURE:
<221> NAME/KEY: misc_feature
<222> LOCATION: (4)..(4)
<223> OTHER INFORMATION: Xaa selected from Y or F
<220> FEATURE:
<221> NAME/KEY: misc_feature
<222> LOCATION: (7)..(7)
<223> OTHER INFORMATION: Xaa selected from V, F or S
<220> FEATURE:
<221> NAME/KEY: misc_feature
<222> LOCATION: (9)..(9)
<223> OTHER INFORMATION: Xaa selected from R, T, N or E

<400> SEQUENCE: 70

Xaa Ile Tyr Xaa Ser Gly Xaa Thr Xaa Tyr Asn Pro Ser Leu Lys Ser
1               5                   10                  15

<210> SEQ ID NO 71
<211> LENGTH: 11
<212> TYPE: PRT
<213> ORGANISM: Artificial Sequence
<220> FEATURE:
<223> OTHER INFORMATION: LCDR1
<220> FEATURE:
<221> NAME/KEY: misc_feature
<222> LOCATION: (5)..(5)
<223> OTHER INFORMATION: Xaa selected from S or G
```

```
<220> FEATURE:
<221> NAME/KEY: misc_feature
<222> LOCATION: (8)..(8)
<223> OTHER INFORMATION: Xaa selected from S or R

<400> SEQUENCE: 71

Arg Ala Ser Gln Xaa Ile Ser Xaa Trp Leu Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: LCDR2
<220> FEATURE:
<221> NAME/KEY: misc_feature
<222> LOCATION: (1)..(1)
<223> OTHER INFORMATION: Xaa selected from A or K
<220> FEATURE:
<221> NAME/KEY: misc_feature
<222> LOCATION: (6)..(6)
<223> OTHER INFORMATION: Xaa selected from Q or E

<400> SEQUENCE: 72

Xaa Ala Ser Ser Leu Xaa Ser
1               5

<210> SEQ ID NO 73
<211> LENGTH: 324
<212> TYPE: DNA
<213> ORGANISM: Artificial Sequence
<220> FEATURE:
<223> OTHER INFORMATION: VL DNA

<400> SEQUENCE: 73
gacatccaga tgacccagtc tccatcttcc gtgtctgcat ctgtaggaga cagagtcacc      60
atcacttgtc gggcgagtca gggtattagc aggtggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgtcagcag gcagacctcc accctcctct cacttttggc     300
ggagggacca aggttgagat caag                                            324

<210> SEQ ID NO 74
<211> LENGTH: 324
<212> TYPE: DNA
<213> ORGANISM: Artificial Sequence
<220> FEATURE:
<223> OTHER INFORMATION: VL DNA

<400> SEQUENCE: 74
gacatccaga tgacccagtc tccatcttcc gtgtctgcat ctgtaggaga cagagtcacc      60
atcacttgtc gggcgagtca gggtattagc aggtggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgtcagcag gcagacctcc accctcctct cacttttggc     300
ggagggacca aggttgagat caaa                                            324

<210> SEQ ID NO 75
<211> LENGTH: 321
<212> TYPE: DNA
```

<213> ORGANISM: Artificial Sequence
<220> FEATURE:
<223> OTHER INFORMATION: VL DNA

<400> SEQUENCE: 75

```
gacatccaga tgacccagtc tccatcttcc gtgtctgcat ctgtaggaga cagagtcacc    60
atcacttgtc gggcgagtca gggtattagc aggtggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgtcagcag acagtctcct ccctatcac ttttggcgga    300
gggaccaagg ttgagatcaa a                                             321
```

<210> SEQ ID NO 76
<211> LENGTH: 324
<212> TYPE: DNA
<213> ORGANISM: Artificial Sequence
<220> FEATURE:
<223> OTHER INFORMATION: VL DNA

<400> SEQUENCE: 76

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataaa gcctccagtt tggaaagtgg ggtcccatca   180
aggttcagcg gcagtggatc tgggacagaa ttcactctca ccatcagcag cctgcagcct   240
gatgattttg caacttatta ctgccagcag gtcaaaagtt actctcctct cacttttggc   300
ggagggacca aggttgagat caaa                                          324
```

<210> SEQ ID NO 77
<211> LENGTH: 321
<212> TYPE: DNA
<213> ORGANISM: Artificial Sequence
<220> FEATURE:
<223> OTHER INFORMATION: VL DNA

<400> SEQUENCE: 77

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgtcagcag gtaaatcacc acccttggac ttttggcgga   300
gggaccaagg ttgagatcaa a                                             321
```

<210> SEQ ID NO 78
<211> LENGTH: 293
<212> TYPE: PRT
<213> ORGANISM: Artificial Sequence
<220> FEATURE:
<223> OTHER INFORMATION: CD47 protein

<400> SEQUENCE: 78

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala

```
            35                  40                  45
Gln Asn Thr Thr Glu Val Tyr Val Lys Trp Lys Phe Lys Gly Arg Asp
 50                  55                  60

Ile Tyr Thr Phe Asp Gly Ala Leu Asn Lys Ser Thr Val Pro Thr Asp
 65                  70                  75                  80

Phe Ser Ser Ala Lys Ile Glu Val Ser Gln Leu Leu Lys Gly Asp Ala
                 85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
        210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
            275                 280                 285

Met Lys Phe Val Glu
    290

<210> SEQ ID NO 79
<211> LENGTH: 467
<212> TYPE: PRT
<213> ORGANISM: Artificial Sequence
<220> FEATURE:
<223> OTHER INFORMATION: control antibody HC

<400> SEQUENCE: 79

Met Gly Trp Ser Leu Ile Leu Leu Phe Leu Val Ala Val Ala Thr Arg
  1               5                  10                  15

Val Leu Ser Glu Val Arg Leu Leu Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Asn Tyr Ala Met Gly Trp Val Arg Gln Ala Pro Gly Lys Gly Leu
     50                  55                  60

Glu Trp Val Ser Ala Ile Ser Gly Ser Gly Gly Ser Thr Tyr Tyr Ala
 65                  70                  75                  80

Asp Ser Val Lys Gly Arg Phe Thr Thr Ser Arg Asp Asp Ser Lys Asn
                 85                  90                  95

Ala Leu Tyr Leu Gln Met Asn Ser Leu Arg Ala Glu Asp Thr Ala Val
```

```
                100             105             110
Tyr Tyr Cys Ala Arg Gly Gly Pro Gly Trp Tyr Ala Ala Asp Val Trp
            115             120             125

Gly Gln Gly Thr Thr Val Thr Val Ser Ser Ala Ser Thr Lys Gly Pro
        130             135             140

Ser Val Phe Pro Leu Ala Pro Ser Ser Lys Ser Thr Ser Gly Gly Thr
145             150             155             160

Ala Ala Leu Gly Cys Leu Val Lys Asp Tyr Phe Pro Glu Pro Val Thr
            165             170             175

Val Ser Trp Asn Ser Gly Ala Leu Thr Ser Gly Val His Thr Phe Pro
            180             185             190

Ala Val Leu Gln Ser Ser Gly Leu Tyr Ser Leu Ser Ser Val Val Thr
            195             200             205

Val Pro Ser Ser Ser Leu Gly Thr Gln Thr Tyr Ile Cys Asn Val Asn
        210             215             220

His Lys Pro Ser Asn Thr Lys Val Asp Lys Lys Val Glu Pro Lys Ser
225             230             235             240

Cys Asp Lys Thr His Thr Cys Pro Pro Cys Pro Ala Pro Glu Leu Leu
            245             250             255

Gly Gly Pro Ser Val Phe Leu Phe Pro Pro Lys Pro Lys Asp Thr Leu
            260             265             270

Met Ile Ser Arg Thr Pro Glu Val Thr Cys Val Val Val Asp Val Ser
        275             280             285

His Glu Asp Pro Glu Val Lys Phe Asn Trp Tyr Val Asp Gly Val Glu
        290             295             300

Val His Asn Ala Lys Thr Lys Pro Arg Glu Glu Gln Tyr Asn Ser Thr
305             310             315             320

Tyr Arg Val Val Ser Val Leu Thr Val Leu His Gln Asp Trp Leu Asn
            325             330             335

Gly Lys Glu Tyr Lys Cys Lys Val Ser Asn Lys Ala Leu Pro Ala Pro
            340             345             350

Ile Glu Lys Thr Ile Ser Lys Ala Lys Gly Gln Pro Arg Glu Pro Gln
            355             360             365

Val Tyr Thr Leu Pro Pro Ser Arg Asp Glu Leu Thr Lys Asn Gln Val
            370             375             380

Ser Leu Thr Cys Leu Val Lys Gly Phe Tyr Pro Ser Asp Ile Ala Val
385             390             395             400

Glu Trp Glu Ser Asn Gly Gln Pro Glu Asn Asn Tyr Lys Thr Thr Pro
            405             410             415

Pro Val Leu Asp Ser Asp Gly Ser Phe Phe Leu Tyr Ser Lys Leu Thr
            420             425             430

Val Asp Lys Ser Arg Trp Gln Gln Gly Asn Val Phe Ser Cys Ser Val
            435             440             445

Met His Glu Ala Leu His Asn His Tyr Thr Gln Lys Ser Leu Ser Leu
            450             455             460

Ser Pro Gly
465

<210> SEQ ID NO 80
<211> LENGTH: 236
<212> TYPE: PRT
<213> ORGANISM: Artificial Sequence
<220> FEATURE:
<223> OTHER INFORMATION: control antibody LC
```

```
<400> SEQUENCE: 80

Met Asp Phe Gln Val Gln Ile Ile Ser Phe Leu Leu Ile Ser Ala Ser
1               5                   10                  15

Val Ile Met Ser Arg Gly Asp Ile Gln Met Thr Gln Ser Pro Ser Ser
            20                  25                  30

Leu Ser Ala Ser Val Gly Asp Arg Val Thr Ile Thr Cys Arg Ala Ser
            35                  40                  45

Gln Ser Ile Ser Ser Tyr Leu Asn Trp Tyr Gln Gln Lys Pro Gly Lys
        50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Ala Asp Leu Pro Ala Phe Ala Phe Gly Gly Gly Thr Lys Val Glu Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```